United States Patent
Peyman

(10) Patent No.: US 11,090,385 B2
(45) Date of Patent: *Aug. 17, 2021

(54) EARLY CANCER DETECTION AND ENHANCED IMMUNOTHERAPY

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 359 days.

This patent is subject to a terminal disclaimer.

(21) Appl. No.: 16/004,401

(22) Filed: Jun. 10, 2018

(65) Prior Publication Data

US 2018/0289805 A1 Oct. 11, 2018

Related U.S. Application Data

(63) Continuation-in-part of application No. 15/853,821, filed on Dec. 24, 2017, now Pat. No. 10,300,121, which is a continuation-in-part of application No. 15/143,981, filed on May 2, 2016, now Pat. No. 9,849,092, which is a continuation-in-part of application No. 14/976,321, filed on Dec. 21, 2015, now Pat. No. 10,136,820.

(60) Provisional application No. 62/614,456, filed on Jan. 7, 2018, provisional application No. 62/577,485, filed on Oct. 26, 2017, provisional application No. 62/569,592, filed on Oct. 8, 2017.

(51) Int. Cl.

| | |
|---|---|
| A61K 9/50 | (2006.01) |
| A61K 41/00 | (2020.01) |
| A61K 48/00 | (2006.01) |
| A61K 47/69 | (2017.01) |
| A61K 9/16 | (2006.01) |
| A61K 9/51 | (2006.01) |
| A61K 45/06 | (2006.01) |
| A61K 9/00 | (2006.01) |
| A61P 35/00 | (2006.01) |
| A61K 9/14 | (2006.01) |
| A61K 38/17 | (2006.01) |
| A61K 38/20 | (2006.01) |
| A61K 38/21 | (2006.01) |
| A61K 38/19 | (2006.01) |
| C07K 16/30 | (2006.01) |
| A61M 37/00 | (2006.01) |
| B82Y 5/00 | (2011.01) |
| A61K 39/395 | (2006.01) |

(52) U.S. Cl.
CPC ........ *A61K 41/0028* (2013.01); *A61K 9/0019* (2013.01); *A61K 9/145* (2013.01); *A61K 9/16* (2013.01); *A61K 9/51* (2013.01); *A61K 38/177* (2013.01); *A61K 38/191* (2013.01); *A61K 38/20* (2013.01); *A61K 38/204* (2013.01); *A61K 38/2006* (2013.01); *A61K 38/212* (2013.01); *A61K 41/0052* (2013.01); *A61K 45/06* (2013.01); *A61K 47/6929* (2017.08); *A61K 48/0075* (2013.01); *A61M 37/0092* (2013.01); *A61P 35/00* (2018.01); *C07K 16/30* (2013.01); *A61K 39/39558* (2013.01); *A61M 37/00* (2013.01); *B82Y 5/00* (2013.01)

(58) Field of Classification Search
None
See application file for complete search history.

(56) References Cited

U.S. PATENT DOCUMENTS

| | | |
|---|---|---|
| 3,993,754 A | 11/1976 | Rahman et al. |
| 4,235,871 A | 11/1980 | Papahadjopoulos et al. |
| 4,522,803 A | 6/1985 | Lenk et al. |
| 4,586,512 A | 5/1986 | Do-huu et al. |
| 4,620,546 A | 11/1986 | Aida et al. |
| 4,658,828 A | 4/1987 | Dory |
| 4,891,043 A | 1/1990 | Zeimer et al. |
| 5,094,854 A | 3/1992 | Ogawa et al. |
| 5,118,666 A | 6/1992 | Habener |
| 5,149,319 A | 9/1992 | Unger |
| 5,203,782 A | 4/1993 | Gudov et al. |
| 5,220,181 A | 6/1993 | Kanal et al. |
| 5,545,618 A | 8/1996 | Buckley et al. |
| 5,935,942 A | 8/1999 | Zeimer |
| 5,976,502 A | 11/1999 | Khoobehi et al. |
| 6,179,767 B1 | 1/2001 | Ziegler et al. |

(Continued)

OTHER PUBLICATIONS

Gao et al., Autologous tumor lysate-pulsed dendritic cell immunotherapy with cytokine-induced killer cells improves survival in gastric and colorectal cancer patients. PLoS One, vol. 9, issue 4 (2014), pp. 1-9.
Min et al. Lentivirus-Mediated sFlt-1 Gene Fragment Transfer Suppresses Retinal Neovascularization. Current Eye Research 34 (2009) 401-410.
Mulder et al. Quantum dots for multimodal molecular imaging of angiogenesis. Angiogenesis 13 (2010) 131-134.
Singerman. Combination therapy using the small interfering RNA bevasiranib. Retina 2009, Abstract Only.
Smith et al., Bioconjugated Quantum Dots for in Vivo Molecular and Cellular Imaging. Adv. Drug Deliv. Rev. 60 (2008) 1226-1240.
You et al. Incorporation of quantum dots on virus in polycationic solution. Int. J. Nanomedicine 1 (2006) 59-64.
Wang et al. Nucleic Acid Conjugated Nanomaterials for Enhanced Molecular Recognition. ACS Nano 3 (2009) 2451-2460.

(Continued)

*Primary Examiner* — Michael D Burkhart
(74) *Attorney, Agent, or Firm* — The Law Office of Patrick F. O'Reilly III, LLC

(57) ABSTRACT

A method of therapy for a tumor or other pathology by administering a combination of thermotherapy and immunotherapy optionally combined with gene delivery. The combination therapy beneficially treats the tumor and prevents tumor recurrence, either locally or at a different site, by boosting the patient's immune response both at the time of original therapy and/or for later therapy. With respect to gene delivery, the inventive method may be used in cancer therapy, but is not limited to such use; it will be appreciated that the inventive method may be used for gene delivery in general. The controlled and precise application of thermal energy enhances gene transfer to any cell, whether the cell is a neoplastic cell, a pre-neoplastic cell, or a normal cell.

22 Claims, 7 Drawing Sheets

(56) References Cited

U.S. PATENT DOCUMENTS

| | | |
|---|---|---|
| 6,197,022 B1 | 3/2001 | Baker |
| 6,248,727 B1 | 6/2001 | Zeimer |
| 6,552,053 B2 | 4/2003 | Sun et al. |
| 6,566,595 B2 | 5/2003 | Suzuki et al. |
| 6,583,111 B1 | 6/2003 | DiMarchi et al. |
| 6,641,553 B1 | 11/2003 | Chee et al. |
| 6,984,655 B1 | 1/2006 | Mod et al. |
| 7,638,139 B2 | 12/2009 | Peyman |
| 8,324,344 B2 | 12/2012 | Kisiel |
| 2002/0174743 A1 | 11/2002 | Mukherjee et al. |
| 2003/0014089 A1 | 1/2003 | Chow et al. |
| 2003/0022374 A1 | 1/2003 | Greenbaum et al. |
| 2004/0003839 A1 | 1/2004 | Curtain |
| 2005/0004625 A1 | 1/2005 | Chow |
| 2006/0173362 A1 | 8/2006 | Toms et al. |
| 2010/0185260 A1 | 7/2010 | Olson |
| 2010/0211146 A1 | 8/2010 | Strowbridge et al. |
| 2011/0270153 A1 | 11/2011 | Olson |
| 2011/0287035 A1 | 11/2011 | Peyman |
| 2012/0226139 A1 | 9/2012 | Peyman |
| 2015/0202466 A1 | 7/2015 | Gertner |
| 2016/0022976 A1 | 1/2016 | Peyman |
| 2018/0133298 A1 | 5/2018 | Peyman |
| 2018/0289805 A1* | 10/2018 | Peyman ............... A61K 9/145 |

OTHER PUBLICATIONS

Lee et al. The retinoblastoma susceptibility gene encodes a nuclear phosphoprotein associated with DNA binding activity. Nature, 329 (1987) 642-645.

Tomczak et al. Designer polymer-quantum dot architectures. Progress in Polymer Science, 34 (2009) 393-430.

Duan and Nle. Cell-penetrating quantum dots based on multivalent and endosome-disrupting surface coatings. J. Am. Chem. Soc. 129 (2007) 3333-3338.

Kim and Taton. Multicomponent nanoparticles via self-assembly with cross-linked block copolymer surfactants. Langmuir, 23 (2007) 2198-2202.

Pan et al. Silica Cross-linked Micelles Loading with Silicon Nanoparticles: Preparation and Characterization. ACS Appl. Mater. Interfaces 5 (2013) 7042-7049.

Lv et al., Surface modification of quantum dots and magnetic nanoparticles with PEG-conjugated chitosan derivatives for biological applications. Chemical Papers 67 (2013) 1404-1413.

Suzuki et al. Quantum Dot FRET Biosensors that Respond to pH, to Proteolytic or Nucleolytic Cleavage, to DNA Synthesis, or to a Multiplexing Combination. J. Am. Chem. Soc. 130 (2008) 5720-5725.

Huang et al. Intermolecular and Intramolecular Quencher Based Quantum Dot Nanoprobes for Multiplexed Detection of Endonuclease Activity and Inhibition, Anal. Chem. 83 (2011) 8913-8918.

Akbarzadeh et al. Liposome: classification, preparation, and applications. Nanoscale Research Letters 8:102 (2013) 1-9.

Sander et al. CRISPR-Cas systems for editing, regulating and targeting genomes. Nature Biotechnology 32:4 (2014) 347-355.

Peyman et al. A High-Resolution 3D Ultrasonic System for Rapid Evaluation of the Anterior and Posterior Segment. Ophthalmic Surgery, Lasers & Imaging 43 (2012) 143-151.

Taylor et al., "Glycogen Synthase Kinase 3 Inactivation Drives T-bet-Mediated Downregulation of Co-receptor PD-1 to Enhance CD8+ Cytolytic T Cell Responses," Immunity, Feb. 16, 2016, vol. 44, No. 2, pp. 274-286.

Husseini el al., "Ultrasonic-Activated Micellar Drug Delivery for Cancer Treatment," J Pharm Sci, May 27, 2008, vol. 98, No. 3, pp. 795-811.

Kong et al., "Efficacy of Liposomes and Hyperthermia in a Human Tumor Xenograft Model: Importance of Triggered Drug Release," Cancer Research, Dec. 15, 2000, vol. 60, pp. 6950-6957.

Phenix et al., "High Intensity Focused Ultrasound Technology, Its Scope and Applications in Therapy and Drug Delivery," Journal of Pharmacy & Pharmaceutical Sciences, Mar. 31, 2014, vol. 17, No. 1, pp. 136-153.

PCT Form 210, International Search Report for PCT/US2018/054880, dated Jan. 9, 2019.

PCT Form 237, Written Opinion of the International Searching Authority for PCT/US2018/054880, dated Jan. 9, 2019.

Mossman "Quantum dots track who gets into cell nucleus" Physorg.com, Sep. 2, 2010, available at http://www.physorg.com/news202628740.html.

You et al. "Incorporation of quantum dots on virus in polycationic solution" Int. J. Nanomedicine, vol. 1, No. 1 (2006), pp. 59-64.

Anscombe "Quantum Dots: Small Structures Poised to Break Big" Photonics Spectra, Jul. 2005, pp. 94-96.

Mali et al. "Intravitreous Injection of a Membrane Depolarization Agent Causes Retinal Degeneration via Matrix Metalloproteinase-9" Investigative Ophthalmology and Visual Science, vol. 46, No. 6 (2005), pp. 2125-2132.

Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.

Aylott "Optical nanosensors-an enabling technology for intracellular measurements" Analyst, vol. 128 (2003), pp. 309-312.

Buck et al. "Optochemical nanosensor PEBBLEs: photonic explorers for bioanalysis with biologically localized embedding" Current Opinion in Chemical Biology, vol. 8 (2004), pp. 540-546.

Fehr et al. "Development and use of fluorescent nanosensors for metabolite imaging in living cells" Biochemical Society Transactions, vol. 23, part 1 (2005), pp. 287-290.

Ferreira et al. "Downstream processing of plasmid DNA for gene therapy and DNA vaccine applications," Tibtech, vol. 18 (2000), pp. 380-387.

Fei et al. "Glucose nanosensors based on redox polymer/glucose oxidase modified carbon fiber nanoelectrodes" Talanta, vol. 65 (2005), pp. 918-924.

Haes et al. "A unified view of propagating and localized surface plasmon resonance biosensors" Anal. Bioanal. Chem, vol. 379 (2004), pp. 920-930.

Cullum et al. "The development of optical nanosensors for biological measurements" Tibtech, vol. 18 (2000), pp. 388-393.

Hauser and Zhang, "Peptides as biological semiconductors," Nature, vol. 468 (2010), p. 516.

Audero et al. Sporadic Autonomic Dysregulation and Death Associated with Excessive Serotonin Autoinhibition. Science, vol. 321 (2008), pp. 130-133.

De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.

Hohne et al. Acetazolamide prevents hypoxic pulmonary vasoconstriction in conscious dogs. J. Appl. Physiol. vol. 97 (2004), pp. 515-521.

Rio-Portilla et al. REM Sleep Post-Eye Movement Activation. International Journal of Bioelectromagnetism, vol. 10, No. 4 (2008), pp. 192-208.

IBM Press Release, Made in IBM Labs: IBM Scientists Demonstrate World's Fastest Graphene Transistor, Feb. 5, 2010, 1 page.

Kurzwiel Al, Engineers envision 2-dimensional graphene metamaterials and 1-atom-thick optical devices. Jun. 10, 2011, 1 page; internet address: http://www.kurzweilai.net/engineers-envision-2-dimensional-graphene-metamaterials-and-1-atom-thick-optical-devices.

Erogbogbo et al. Plasmonic gold and luminescent silicon nanoplafforms for multimode imaging of cancer cells. Integr. Biol. 5 (2013) 144-150.

Yezhelyev et al., Proton-Sponge-Coated Quantum Dots for siRNA Delivery and Intracellular Imaging. JAm. Chem. Soc. 130 (2008) 9006-9012.

Rajan and Raj. Potential Drug Delivery Applications of Chitosan Based Nanomaterials. I.Re.CH.E. 5 (2013) 145-155.

Song et al., Tumor Cell Targeting Using Folate-Conjugated Fluorescent Quantum Dots and Receptor-Mediated Endocytosis. Clinical Chemistry 55 (2009) 955-963.

(56) References Cited

OTHER PUBLICATIONS

Liu et al. Bioconjugated Pluronic Triblock-Copolymer Micelle-Encapsulated Quantum Dots for Targeted Imaging of Cancer: In Vitro and in Vivo Studies. Theranostics 2 (2012) 705-713.
Jin et al. Preparation and Characterization of Highly Fluorescent, Glutathione-coated Infrared Quantum Dots for in Vivo Fluorescence Imaging. Int. J. Mol. Sci. 9 (2008) 20440-2061.
Liu et al., Endocytic Trafficking of Nanoparticles Delivered by Cell-penetrating Peptides Comprised of Nona-arginine and a Penetration Accelerating Sequence, PLOS One 8 (2013) e67100, 12 pages.
Liu et al., Intracellular Delivery of Nanoparticles and DNAs by IR9 Cell-penetrating Peptides, PLOS One 8 (2013) e64205 (13 pages).
Liu et al., Cell-Penetrating Peptide-Functionalized Quantum Dots for Intracellular Delivery. J. Nanosci. Nanotechnol. 10 (2010) 7897-7905.
Liu et al., Cellular Internalization of Quantum Dots Noncovalentiy Conjugated with Arginine-Rich Cell-Penetrating Peptides. J. Nanosci. Nanotechnol. 10 (2010) 6534-6543.
Xu et al., Nona-Arginine Facilitates Delivery of Quantum Dots into Cells via Multiple Pathways. J. Biomedicine and Biotechnology 2010, Article ID 948543, 11 pages.
Delehanty et al., Self-Assembled Quantum Dot-Peptide Bioconjugates for Selective Intracellular Delivery. Bioconjug Chem 17 (2006) 920-927.
Narayanan et al., Mimicking cellular transport mechanism in stem cells through endosomal escape of new peptide-coated quantum dots. Scientific Reports 3, article No. 2184, 6 pages.
Ho et al., Combining QD-FRET and Microfluidics to Monitor DNA Nanocomplex Self-Assembly in Real-Time. J. Vis Exp. 30 (2009) 1432, 3 pages.
Biju et al., Delivering quantum dots to cells: bioconjugated quantum dots for targeted and nonspecific extracellular and intracellular imaging. Chem. Soc. Rev. 39 (2010) 3031-3056.
Algar and Krull. Toward a Multiplexed Solid-Phase Nucleic Acid Hybridization Assay Using Quantum Dots as Donors in Fluorescence Resonance Energy Transfer. Anal Chem. 81 (2009) 4113-4120.
Gao et al. In vivo cancer targeting and imaging with semiconductor quantum dots. Nature Biotechnology 22 (2004) 969-976.
Gussin et al. Binding of Muscimol-Conjugated Quantum Dots to GabaC Receptors. J. Am Chem. Soc. 128 (2006) 15701-15713.
He et al. Highly Luminescent Water-Dispersible Silicon Nanowires for Long Term Immunofluorescent Cellular Imaging. Angew. Chem. Int. Ed. 50 (2011) 3080-3083.
Heiss et al. Image-guided convection-enhanced delivery of muscimol to the primate brain. J Neurosurg. 112 (2010) 790-795.
Lugo et al. Remote switching of cellular activity and cell signaling using light in conjunction with quantum dots. Biomedical Optics Express 3. (2012) 447-454.
Pappas et al. Nanoscale Engineering of a Cellular Interface with Semiconductor Nanoparticle Films for Photoelectric Stimulation of Neurons. Nano Letters 7 (2007) 513-519.
Rosenthal et al. Biocompatible Quantum Dots for Biological Applications. Chem Biol. 18 (2011) 10-24.
Templeton. Tiny Q-dots may enable more precise brain surgery. Pittsburgh Post-Gazette, Apr. 10, 2007, 4 pages.
van Rooy et al. Comparison of five different targeting ligands to enhance accumulation of liposomes into be brain. Journal of Controlled Release 150 (2011) 30-36.
Wen et al. Theranostic liposomes loaded with quantum dots and apomorphine for brain targeting and boimaging. International Journal of Nanomedicine 7 (2012) 1599-1611.
Zhong et al. Modular design of an ultrahigh-intensity nanoparticle probe for cancer cell imaging and rapid visual detection of nucleic acids. Chem Commun., 48 (2012) 6277-6279.
Baker and Baker. Luminescent Carbon Nanodots: Emergent Nanolights. Angew. Chem. Int. Ed. 49 (2010) 6726-6744.

Hofmann-Amtenbrink et al. Superparamagnetic nanoparticles for biomedical applications, Nanostructured Materials for Biomedical Applications, (ed. M.C. Tan.) 2009, chap. 5, 119-149.
Joeres et al. Quantitative Comparison of Optical Coherence Tomography after Pegaptanib or Bevacizumab in Neovascular Age-Related Macular Degeneration, Ophthalmology 115 (2008) 347-354.
Andor Technology, "Transport Across the Nuclear Membrane Using Quantum Dots," Aug. 23, 2011, available at http://www.andor.com/company/news/?docID=1224.
Boyden, "Optogenetics: Using Light to Control the Brain," The Dana Foundation, Nov. 30, 2011, available at http://www.dana.org/news/cerebrum/detail.aspx?id=34614.
Buchen, "Illuminating the Brain," Nature, vol. 465, May 6, 2010, pp. 26-28.
Dixit et al., "Quantum Dot Encapsulation in Viral Capsids," Nano Letters, vol. 6, No. 9 (2006); pp. 1993-1999.
Deisseroth, "Optogenetics," Nature Methods, Published online Dec. 20, 2010, available at http://www.stanford.edu/group/dlab/papers/deisserothnature2010.pdf.
Deisseroth, "Optogenetics: Controlling the Brain with Light [Extended Version]," Scientific American, Published online Oct. 20, 2010, available at http://www.scientificamerican.com/article.cfm?id=optogenetics-controlling.
Dubertret et al., "In vivo Imaging of Quantum Dots Encapsulated in Phospholipid Micelles," Science, vol. 298, No. 5599 (2002), pp. 1759-1762.
Gill et al., "Fluorescence Resonance Energy Transfer in CdSe/ZnS-DNA Conjugates: Probing Hybridization and DNA Cleavage," J. Phys. Chem. B., vol. 109 (2005), pp. 23175-23179.
Joo et al., "Enhanced Real-Time Monitoring of Adeno-Associated Virus Trafficking by Virus-Quantum Dot Conjugates," ACSNano, vol. 5, issue 5 (2011); pp. 3523-3535.
Michalet et al., "Quantum Dots for Live Cells, in Vivo Imaging, and Diagnostics," Science, 307, No. 5709 (2005), pp. 538-544.
Yizhar et al., "Optogenetics in Neural Systems," Neuron, vol. 71 (2011), 9-34.
Zhang et al., "Optogenetic interrogation of neural circuits: technology for probing mammalian brain structures," Nature Protocols, vol. 5, No. 3 (2010), pp. 439-456.
Aguilera et al. "Systemic in vivo distribution of activatable cell penetrating peptides is superior to cell penetrating peptides," Integr Biol (Camb), vol. 1 , No. 5-6 (2009), pp. 371-381.
Kelley. "What Clinicians Need to Know About Molecular Markers in Solid Tumors" Aug. 6, 2010, available at http://www.medscape.org/viewarticle/725989.
Nguyen et al. "Surgery with molecular fluorescence imaging using activatable cell-penetrating peptides decreases residual cancer and improves survival," Proc. Nat. Acad. Sci., 107 (2010) 4317-4322.
Olson et al. "In vivo characterization of activatable cell penetrating peptides for targeting protease activity in cancer," Integr Bioi, 1 (2009) pp. 382-393.
Olson et al. "Activatable cell penetrating peptides linked to nanoparticles as dual probes for in vivo fluorescence and MR imaging of proteases," Proc. Nat. Acad. Sci. 107 (2010) 4311-4316.
Hoare et al. "A Magnetically-Triggered Composite Membrane for On-Demand Drug Delivery," Nano Lett. 9 (2009) 3651-3657.
Mornet et al., Magnetic nanoparticle design for medical diagnosis and therapy, J. Mater. Chem., 14 (2004) 2161-2175.
Sexton et al. "A Protective Vaccine Delivery System for in Vivo T Cell Stimulation Using Nanoengineered Polymer Hydrogel Capsules," ACS Nano, vol. 3, No. 11 (2009), pp. 3391-3400.
Alavarez-Lorenzo et al., "Temperature-sensitive chitosan-poly(N-isopropylacrylamide) interpenetrated networks with enhanced loading capacity and controlled release properties" J. Controlled Release 102(3), (2005) 629-641.
Balasubramaniam et al., "Poly(N-isopropylacrylamide)-Coated Superaramagnetic Iron Oxide Nanoparticles: Relaxometric and Fluorescence Behavior Correlate to Temperature-Dependent Aggregation" Chem. Mater., 2011, 23, 3348-3356.
Benyettou et al., "Magnetoliposome for alendronate delivery" J. Mater. Chem., 21 (2011) 4813-4820.

(56) References Cited

OTHER PUBLICATIONS

Budgin et al. "Functionalization of Magnetic Nanoparticles with Amphiphilic Block Copolymers: Self-Assembled Thermoresponsive Submicrometer Particles" Langmuir 28 (2012) 4142-4151.

Farokhzad et al., "Impact of Nanotechnology on Drug Delivery" ACS Nano 3(1) 2009, 16-20.

Filipa et al., "Polyelectrolyte-Coated Unilamellar Nanometer-Sized Magnetic Liposomes" Langmuir 2009, 25(12), 6793-6799.

Pothayee et al., "Magnetic Block Ionomer Complexes for Potential Dual Imaging and Therapeutic Agents" Chem. Mater. 2012, 24, 2056-2063.

Tai et al. "Thermosensitive liposomes entrapping iron oxide nanoparticles for controllable drug release" Nanotechnology 20 (2009) 135101 (9 pages).

Xu et al. "Controlled Release and Assembly of Drug Nanoparticles via pH-Responsive Polymeric Micelles: A Theoretical Study" J. Phys. Chem. B, 2012, 116 (20), 6003-6009.

Booth et al. Exosomes and HIV Gag bud from endosome-like domains of the T cell plasma membrane. The Journal of Cell Biology, vol. 172, No. 6, Mar. 13, 2006, 923-935.

Heath et al., Varying Polymer Architecture to Deliver Drugs AAPS J. 9 (2007) Nanotechnology and Drug Delivery, article 26 (http://www.aapsi.org) E235-E240.

Jamagin et al. Treatment of cholangiocarcinoma with oncolytic herpes simplex virus combined with external beam radiation therapy. Cancer Gene Therapy 13 (2006) 326-334.

Ding et al., Farnesyltransferase inhibitor tipifamib inhibits Rheb prenylation and stabilizes Bax in acute myelogenous leukemia cells. Haematologica 99 (2014) 60-69.

Kleiner et al. Farnesyl and geranylgeranyl transferase inhibitors: an anti-inflammatory effect. Comment to "Inhibition of protein geranylgeranylation and farnesylation protects against graft-versus-host disease via effects on CD4 effector T cells" haematological 98 (2013) e44-e45.

Karp et al. Multi-institutional phase 2 clinical and pharmacogenomic trial of tipifarnib plus etoposide for elderly adults with newly diagnosed acute myelogenous leukemia. Blood 119 (2012) 55-63.

Hong et al. Phase I Trial of a Combination of the Multikinase Inhibitor Sorafenib and the Farnesyltransferase Inhibitor Tipifamib in Advanced Malignancies. Clin Cancer Res 15 (2009), 7061-7068.

Kurzrock et al. Phase I Study of Alternate-Week Administration of Tipifamib in Patients with Myelodysplastic Syndrome. Clin Cancer Res 14 (2008) 509-514.

Haferlach. Molecular Genetic Pathways as Therapeutic Targets in Acute Myeloid Leukemia. (2008) 400-411.

Armand et al. The Emerging Role of Targeted Therapy for Hematologic Malignancies: Update on Bortezomib and Tipifamib. The Oncologist 12 (2007) 281-290.

Yanamandra et al. Tipifarnib and Bortezomib are Synergistic and Overcome Cell Adhesion-Mediated Drug Resistance in Multiple Myeloma and Acute Myeloid Leukemia. Clin Cancer Res 12 (2006) 591-599.

Beaupre et al. R115777 induces Ras-independent apoptosis of myeloma cells via multiple intrinsic pathways. Mol Cancer Ther 3 (2004) 179-186.

Leite et al. PE and PS Lipids Synergistically Enhance Membrane Poration by a Peptide with Anticancer Properties. Biophysical Journal 109 (2015) 936-947.

Bakalova et al., "Quantum Dot-Conjugated Hybridization Probes for Preliminary Screening of siRNA Sequences" J. Am. Chem. Soc., (2005), 127 (32), pp. 11328-11335.

Derfus et al. "Targeted Quantum Dot Conjugates for siRNA Delivery" Bioconjugate Chem., vol. 18, No. 5 (2007) pp. 1391-1396.

Ebenstein et al. "Combining atomic force and fluorescence microscopy for analysis of quantum-dot labeled protein-DNA complexes" J. Molecular Recognition, vol. 22, issue 5 (2009), pp. 397-402.

Gill et al. "Fluorescence Resonance Energy Transfer in CdSe/ZnS-DNA Conjugates: Probing Hybridization and DNA Cleavage" J. Phys. Chem. B, vol. 109, (2005), pp. 23715-23719.

Joo et al. "Enhanced Real-Time Monitoring of Adeno-Associated Virus Trafficking by Virus-Quantum Dot Conjugates" ACS Nano, vol. 5, No. 5 (2011), pp. 3523-3535.

Lim et al. "Specific Nucleic Acid Detection Using Photophysical Properties of Quantum Dot Probes" Anal. Chem., vol. 82, No. 3 (2010), 886-891.

\* cited by examiner

EARLY CANCER DETECTION AND ENHANCED IMMUNOTHERAPY

This patent application claims priority to U.S. Provisional Patent Application No. 62/614,456, entitled "Cancer Treatment Methods Using Thermotherapy and/or Enhanced Immunotherapy", filed on Jan. 7, 2018, and is a continuation-in-part of application Ser. No. 15/853,821, entitled "Early Cancer Detection And Enhanced Immunotherapy", filed Dec. 24, 2017, which claims priority to U.S. Provisional Patent Application No. 62/569,592, entitled "Cancer Treatment Methods Using Thermotherapy and/or Enhanced Immunotherapy", filed on Oct. 8, 2017, and to U.S. Provisional Patent Application No. 62/577,485, entitled "Cancer Treatment Methods Using Thermotherapy and/or Enhanced Immunotherapy", filed on Oct. 26, 2017, and Ser. No. 15/853,821 is a continuation-in-part of application Ser. No. 15/143,981, entitled "Early Cancer Detection And Enhanced Immunotherapy", filed May 2, 2016, now U.S. Pat. No. 9,849,092, which is a continuation-in-part of application Ser. No. 14/976,321, entitled "Method to Visualize Very Early Stage Neoplasm or Other Lesions", filed Dec. 21, 2015, the disclosure of each of which is hereby incorporated by reference as if set forth in their entirety herein.

Figure 1:
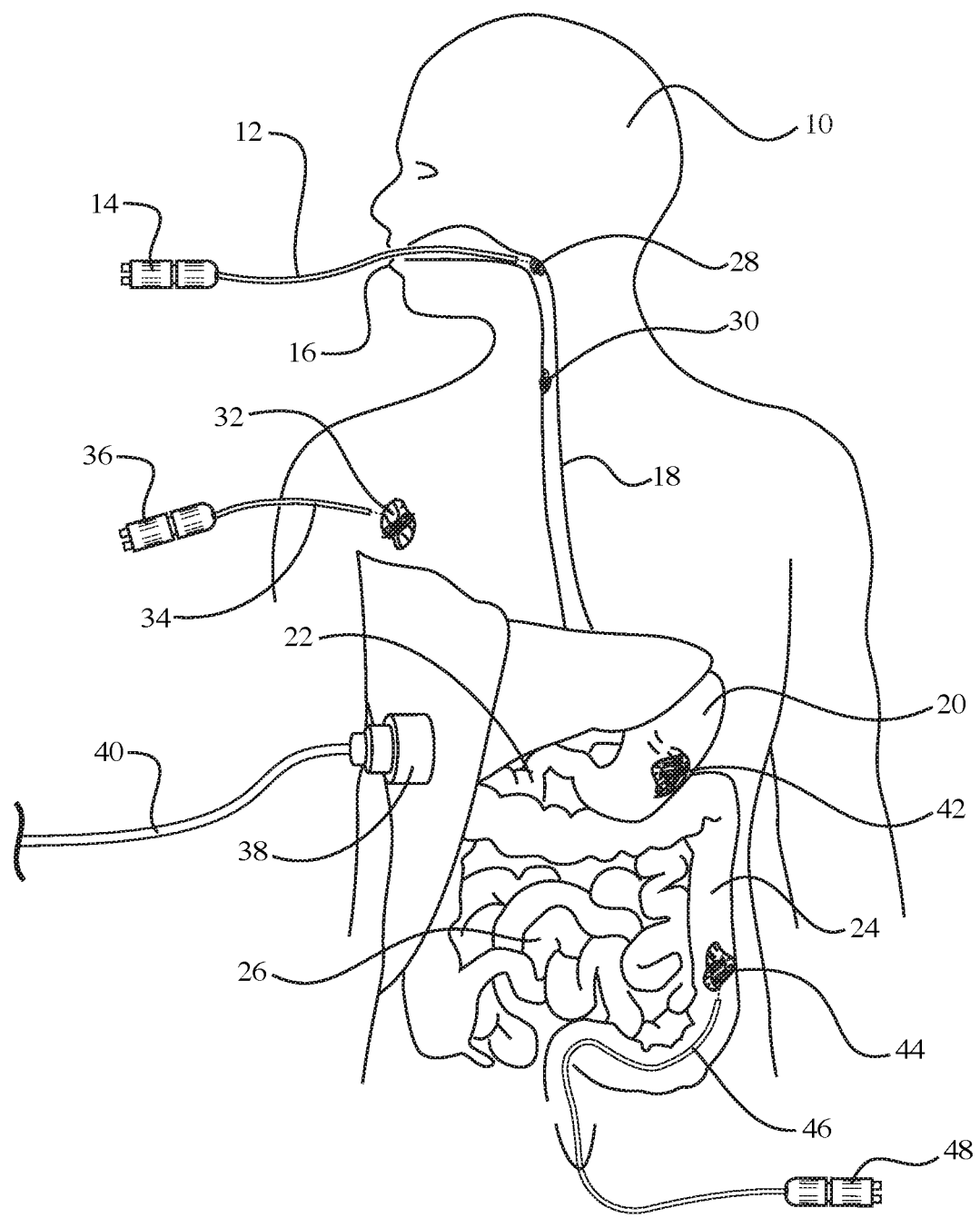
FIG. 1 is a diagrammatic illustration of a human body showing the treatment of tumors located in various areas of the body with light emitted by fiber optic devices, according to an embodiment of the invention.

Various factors may lead one to suspect the presence of a small cancerous or neoplastic tumor in a patient. Such factors include the patient's genetic history, environmental conditions to which the patient is or has been exposed, the presence of biomarkers in the patient's blood, or the presence of a lesion on a patient's skin or mucosal surface. A small neoplasm of 1 to 2 millimeters (mm) in diameter, however, is often not recognized unless and until it produces some clinical symptom.

In a patient having a genetic mutation indicating a predisposition to cancer, prophylactic surgical intervention, such as a bilateral mastectomy performed in a patient having a genetic mutation indicating a predisposition to breast cancer, is seldom performed. Additionally, a genetic predisposition to one type of cancer may not lead to that type of cancer, e.g. breast cancer, but it may lead to another unsuspected type of cancer, e.g. malignant melanoma. Even if the other type of cancer is suspected, because of the finding of biomarkers in the blood, a small internal lesion may not be seen on radiography, or may not be accessible by surgery, or the collateral complications may not be acceptable. It may not suffice to just know the biomarker for a tumor, because this information may not indicate whether the tumor is a primary site or a metastatic site, the tissue of its origin, and/or its location. It is appreciated that some treatment techniques such as surgery or radiation may be useful, but only if the tumor is tissue specific. Radiation and chemotherapy also have their own side effects, and may not destroy the tumor completely. Larger tumors present a much complex problem, e.g., mutations in one area of the tumor are usually different from mutations in another area of the same tumor.

It is clearly preferable, then, to manage small early neoplasms that have not progressed to a larger tumor to provide the patient an improved clinical prognosis.

The invention includes a method of therapy for a non-surgically accessible tumor by administering a combination of thermotherapy and immunotherapy combined with gene delivery. In one or more embodiments, the gene delivery may use CRISPR-cas9 mediated Homology—Independent Targeted Integration (HITI) or Homology Directed Repair (HDR). The combination therapy beneficially treats the tumor and prevents tumor recurrence, either locally or at a different site, by boosting the patient's immune response both at the time or original therapy and/or for later therapy as a "booster" vaccine with or without viral-like particles (VLP) or adjuvants to the original therapy by administering them with antibody coated nanoparticles conjugated with checkpoint inhibitors, such as PD-1, PD-L1, CTLA-4, Jagged 1 inhibitor 15D11, etc. and anti-inflammatory agents, such as Rock inhibitors, Fasudil, etc., Wnt inhibitors, such as niclosamide etc. to enhance cellular immune response of the patient while reducing the inflammatory response and preventing an auto immune reaction or cytokine storm. In one embodiment, the vaccine with or without VLP, adjuvants, sodium bicarbonate to modify acidic tumor cell environment is combined with checkpoint inhibitors, such as PD-1, PD-L1, CTLA-4, Jagged 1 inhibitor 15D11, etc., anti-VEGF, and anti-inflammatory agents, Rock inhibitors, such as Fasudil or Botox, or Wnt inhibitor, such as niclosamide, ivermectin and Selamectin, etc., can be injected every six months or once a year, or is used in the treatment of recurrent metastatic disease. In another embodiment the antibody coated nanoparticles or solid lipid nanoparticles are coated with thermosensitive polymers which are released at the temperature or 41-42 C under thermotherapy and administered with checkpoint inhibitors, such as PD-1, PD-L1, CTLA-4, Jagged 1 inhibitor 15D11, etc. and Rock inhibitors, such as Fasudil or Botox, or Wnt inhibitor, such as niclosamide, ivermectin, or Selamectin and/or an antineoplastic medication depending on the cancer, at lower dose than is normally recommended, but is made more effective by thermotherapy.

In one embodiment, N-myristoyltransferase (NMT) in cell cycle is inhibited which is involved in cell proliferation etc. NMT conjugates with rare fatty acid and proteins. Lipid modification through inhibition of N-myristoylation interferes with cell multiplication. Numerous antimalarial, anti-fungal, antiparasitic, antinematodes or antifilarial, antiviral, compounds can interfere with NMT function, but specifically the compound IMP-1088 which inhibits capsid formation in viruses. However combining antibody coated nanoparticles with the compound IMP-1088, NMT inhibitors, DDD85646 and DDD100870 and cHSC70 and/or enolase can be used alone or synergistically with Wnt inhibitors or Rock inhibitors, as anticancer therapeutic agent(s) conjugated with antibody coated nanoparticles/medication injected intravenously or intra-arterially to the organ containing the tumor to inhibit the cancer cell proliferation along with controlled thermotherapy.

In one embodiment the diagnosis and precision thermo-immune therapy is performed locally or limited to an organ (e.g. head, lung, intestinal tract or extremities etc.) having radiographically or thermoacoustically imaged a small tumor, anticancer therapeutic agent conjugated with antibody coated nanoparticles/medication is injected intravenously or intra-arterially to the organ containing the tumor, while sensitizing the immune system to the tumor antigen to damage the original tumor and also attack the potentially existing circulating tumor cells, tumor exosomes, or yet invisible metastatic lesion using thermotherapy locally combined with antibody coated nanoparticles, checkpoint inhibitors, and an immune stimulator such as VLP, adjuvants, or toll like receptors, TNF alpha, etc. attached to antibody coated pluralities of nanoparticles or solid lipid nanoparticles administered simultaneously to stimulate body's immune response and eliminate the localized tumor and its circulating cells, exosomes or metastatic lesions by innate immune cells stimulation.

In one embodiment, combination antibody coated nanoparticles, such as nanoparticles or solid lipid or liposomes, dextrin, etc. conjugated with Wnt inhibitors, such as Ivermectin and Selamectin and inhibitor of N-myristoyltransferase, specifically IMP-1088, or NMT inhibitors, DDD85646 and DDD100870, checkpoint inhibitors and an immune stimulant (e.g., VLP), and sodium bicarbonate to modify acidic tumor cell environment, adjuvants, etc. administered intravenously or intra-arterially to work synergistically in preventing cancer cell proliferation of a small locally confined tumor along with controlled thermotherapy at the temperature of 40-43 degrees C. and treat simultaneous localized immune therapy.

In one embodiment, early stage tumor therapy involves the anticancer therapeutic agents conjugated with antibody coated nanoparticles/medication injected intravenously or intra-arterially to the organ containing the tumor while the thermotherapy performed with a laser fiber optic locally is brought to the tumor site through the feeding artery, or a focused ultrasound is used in a thermal or non-thermal mode from outside the body under temperature control using an imaging system or thermoacoustic temperature imaging unit.

In one embodiment, a portable photoacoustic or thermoacoustic transducer probe can be moved in any direction on the body, e.g., up and down, side to side, etc., over the skin while emitting a laser light, microwave, or focused ultrasound etc. and recording the sound waves from the antibody coated nanoparticles producing a thermal expansion of nanoparticles. Using a processor in the photoacoustic or thermoacoustic unit, one uses the photoacoustic or thermoacoustic response data to construct a two- or three-dimensional image of a tumor for diagnosis of a lesion in the body.

In one embodiment, the hand held photoacoustic/thermoacoustic probe permits scanning any bodily surface locally to diagnose presence of a tumor, including but not limited to, the skin, breast, eye, central nervous system (CNS), spinal cord, extremities, internal organs, lung, nose, chest, trachea, throat, abdomen, and urogenital organs after administration of the pluralities of antibody coated nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) or solid lipid nanoparticles injected intravenously, topically or intra-arterially, and irradiated with a source of thermal energy such as laser, focused ultrasound or an alternating magnetic field. The cyclodextrin nanoparticles may carry medication, checkpoint inhibitors, VLP, adjuvants, and/or sodium bicarbonate to modify the acidic tumor cell environment and act as slow release polymers at the tumor site, which can be released by thermal energy.

In one embodiment, a laser fiber optic can be used for diagnosis and therapy of the surface or internal lesions after administration of the pluralities of antibody-coated nanoparticles with cell penetrating peptides (CPP), activating CPP (ACPP), biotin, streptavidin or antibody coated nanoparticles conjugated with medication and (alpha)-cyclodextrin, (beta)-cyclodextrin, (gamma)-cyclodextrin, hydroxypropyl-b-cyclodextrin (bHPCD) or solid lipid nanoparticles intravenously, topically for surface tumors, skin, mucosa, or through the accessible cavities such as the eyes, vitreous cavity, bladder, mouth, throat, esophagus, stomach, duodenum, rectum, colon, small intestinal tract, and lung. In this embodiment, the antibody/cyclodextrin coated nanoparticles carry medication, such as Rock inhibitors, Wnt inhibitors and/or Inhibitors of N-myristoyltransferase, specifically IMP-1088, or NMT inhibitors, DDD85646 and DDD100870 and checkpoint inhibitors, or VLP, adjuvants, sodium bicarbonate to modify the acidic tumor cell environment and immune stimulators and act as slow release polymers delivered via a flexible fiber optic and a tube is inserted through the natural orifices of the body (see FIGS. 1 and 4) or through a feeding artery or vein (see FIG. 5) to bring the laser pulses close to the tissue containing a tumor, and deliver the nanoparticles, but also use the laser energy to heat the accessible lesion or apply thermal energy externally using microwave, focused ultrasound in thermal and non-thermal modes releasing the medication(s) and stimulate the immune system to attack the tumor cells locally or wherever they are systemically by cellular immune response. In one embodiment, the methods of delivery of antibody coated nanoparticles/medications are internal through the arteries or veins or through the body orifices as shown by the drawings (see FIGS. 1 and 4-7) or through an incision (e.g., made in the abdomen, etc. or subcutaneous or intramuscular, etc. injection in the desired location or tissue, or by topical application).

For example, as shown in FIG. 1, one laser fiber optic device 12 may be inserted through the mouth 16 of a person 10 so as to treat an esophageal tumor 28 by emitting light pulses generated a light source 14. In addition, the laser fiber optic device 12 may be further inserted into the esophagus 18 so as treat another tumor 30 located further down in the esophagus 18. In addition, as shown in FIG. 1, a skin tumor 32 located near the right shoulder of the person 10 may be treated with a laser fiber optic device 34 having a light source 36. Next, turning to the digestive system in FIG. 1, which includes the stomach 20, duodenum 22, large intestine 24, and small intestine 26, further aspects of the illustrated embodiment will be described. In FIG. 1, it can be seen that a tumor 42 is disposed in the stomach 20, and another tumor 44 is disposed in the large intestine 24. The tumor 44 in the large intestine 24 is being treated with a laser fiber optic device 46 that has been inserted into the large intestine 24 through the rectum. The laser fiber optic device 46 has a light source 48. Also, as shown in FIG. 1, a photoacoustic receiver 38 with cord 40 may be placed against the body of the person 10 in order to record a photoacoustic/thermoacoustic response resulting from the thermal expansion of nanoparticles attached to the tumor (e.g., attached to tumor 42 in stomach 20) that are heated by the laser light pulses from a fiber optic device. As described above, the nanoparticles may be delivered to the tumor site prior to the heating thereof by a tube attached to the fiber optic device.

In one embodiment, the thermotherapy is done either internally or externally using a laser applied through a fiber optic, etc. (see e.g., FIGS. 1-6). In one embodiment, the antibody coated nanoparticles/medications are delivered intra-arterially or intravenously, but the thermotherapy is done externally using focused ultrasound, microwaves, radio frequency (RF), or using an alternating magnetic field when nanoparticles are magnetic or paramagnetic.

In some situations, as in the brain, the thermotherapy can be done at a low temperature (e.g., with focused ultrasound) that make the tumor vessels leakier prior to the injection on the antibody-coated nanoparticles. In another embodiment, the nanoparticles are injected prior to the thermotherapy, etc.

In one embodiment, the source of energy is a focused ultrasound in a non-thermal or thermal mode applied from the outside the body while the pluralities of antibody-coated nanoparticles/medications are piezoelectric, such as quartz, graphene, or perovskites, nanobubbles, perfluorocarbon liquid filled vesicles, etc., and administered intra-arterially or intravenously, etc.

Figure 5:
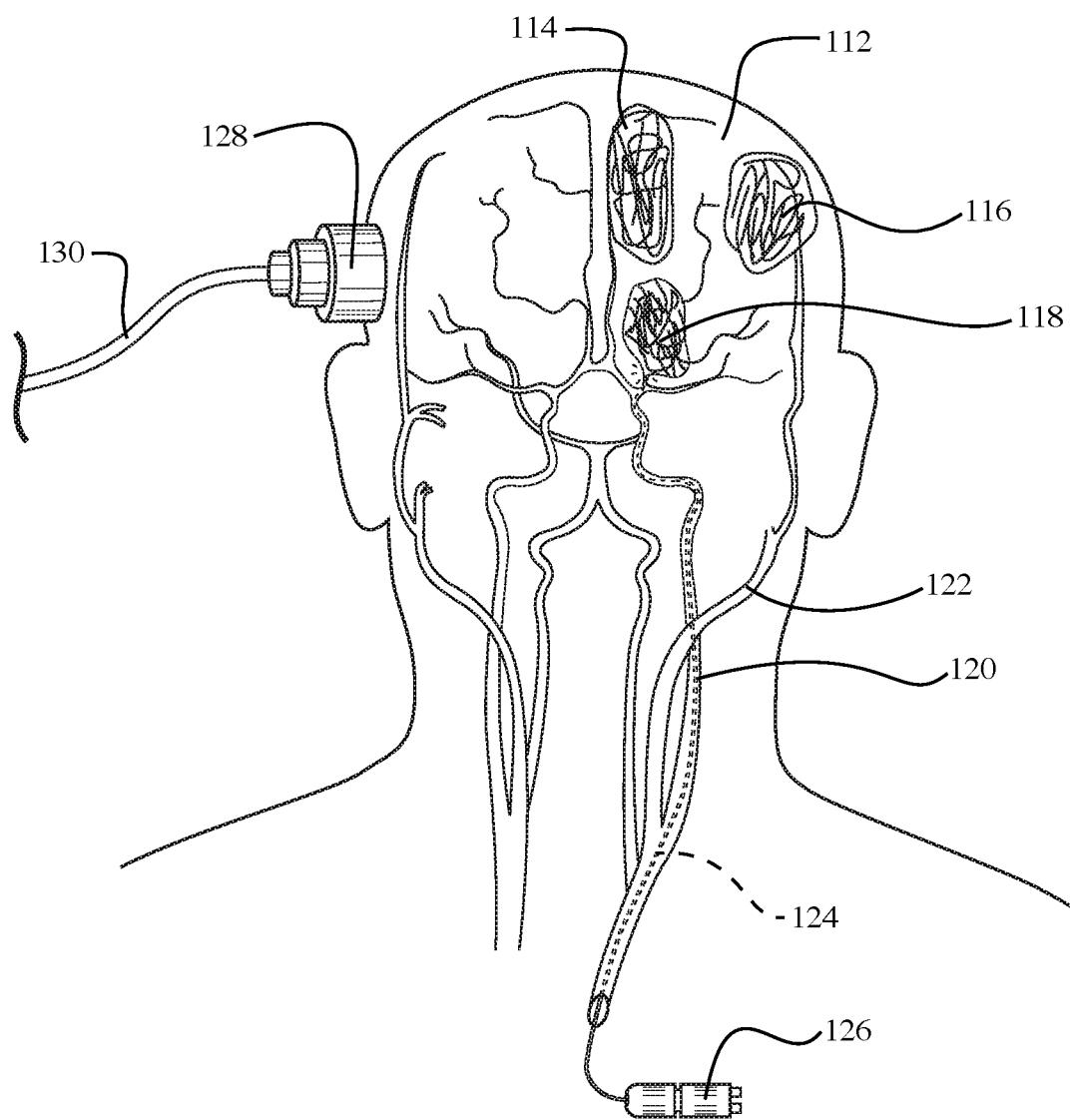
FIG. 5 is a diagrammatic illustration of the circulation system and brain of the human head showing tumors located in various areas of the brain and the treatment of one of the tumors with light emitted by a fiber optic device, according to yet another embodiment of the invention.

In one embodiment, as shown in the embodiment of FIG. 5, the delivery of antibody coated nanoparticles/medication is done through an artery and thermotherapy is done with an internal laser using a fiber optic.

In one embodiment, one can deliver the antibody coated nanoparticles/medication internally and heat up the tumor preferably externally (e.g., by using a focused ultrasound). This is preferred for internally located tumors, such as in the brain and internal organs that cannot be reached by the laser or the size of the tumors are mostly larger than 4 millimeters (mm) in diameter.

In another embodiment, any method or delivery of nanoparticles can be used depending on the location of the tumor and its thickness. Lasers are used mostly for small accessible lesions or superficial tumors, or laser accessible tumors via a fiber optic or external laser for tumors having a thickness of about 1-4 mm. All other tumors can be preferably treated by a source of energy that penetrates deep in the tissue (e.g., focused ultrasound, microwaves, radio frequency (RF), or alternating magnetic field). In all cases, thermal delivery and temperature are controlled by either a photoacoustic imaging or thermoacoustic imaging unit to the desired level of temperature which is predetermined.

In one embodiment, a miniature capsule with an imaging camera, which is equipped with a laser system, is swallowed by the patient that constantly radiates a laser pulse, as it passes through the intestinal tract and transmits recorded images to a receiver outside the body.

In one embodiment, a photoacoustic sound wave is produced when pluralities of antibody-coated nanoparticles are injected intravenously with cell penetrating peptides (CPP), activating CPP (ACPP), biotin, streptavidin, and/or the cyclodextrin antibody-coated nanoparticles carry medication, inhibition of N-myristoyltransferase such as many anti malaria parasites medication, specifically IMP-1088, or NMT inhibitors, DDD85646 and DDD100870, checkpoint inhibitors, or VLP, adjuvants, sodium bicarbonate to modify the acidic tumor cell environment and immune stimulators, such as TNF alpha, toxin, etc., and act as slow release polymeric drug release, where the nanoparticles accumulate at the site of the tumor(s) in the intestinal tract and are stimulated with the laser pulses which heat and create a photoacoustic sound that is recorded by a receiver located outside the body and in contact with body surface, such as over the abdomen, etc., and is analyzed by software while an internal capsule with a video camera is traveling through the intestine and locates the presence of a tumor.

In one embodiment, as the capsule passes in front of a lesion in the intestinal tract, which has accumulated the pluralities of antibody coated nanoparticles or solid lipid nanoparticles thereon, the laser pulse creates a photoacoustic sound that can be recorded by a receiver positioned on the trunk of the patient and records the image of the lesion and the temperature at that site as the capsule travels through the intestine.

In one embodiment, the photoacoustic sound can be correlated with the video taken by the capsule and the location of the tumor is determined even if the tumor is too small to be recognized by CT scan or radiography or too small to make any visible or physical symptom. In one embodiment, the capsule emits a significant amount of energy to increase the temperature at the tumor site to release the medication, gene, from the antibody-coated nanoparticles with cell penetrating peptides (CPP), activating CPP (ACPP), biotin, streptavidin or the cyclodextrin antibody-coated nanoparticles which carry medication, such as Rock inhibitors, Wnt inhibitors or inhibitors of N-myristoyltransferase, IMP-1088, NMT inhibitors, DDD85646 and DDD100870, and checkpoint inhibitors, and/or VLP, adjuvants, sodium bicarbonate to modify acidic tumor cell environment and other immune stimulators, such as TNF alpha, IL 2 IL-6, toll like receptor 7/8 that stimulate innate immune cell response, etc. and are released from the slow release polymers, and damage and kill the tumor cells while releasing their cellular antigens in the circulation to attract cellular immune response and kill the remaining tumor cells that are present locally or might exist in the body.

In one embodiment, a laser fiber optic with or without the camera, while pulsing laser energy, is passed through the mouth to the stomach or through the rectum into the colon or through the ureter inside the bladder, through the mouth, throat, trachea, and bronchi, etc. or through the vagina inside the uterus or further through one of the fallopian tubes toward the ovaries.

In one embodiment, the laser pulse produces a photoacoustic or thermoacoustic response from the pluralities of antibody-coated nanoparticles with cell penetrating peptides (CPP), activating CPP (ACPP), biotin, streptavidin or the cyclodextrin antibody coated nanoparticles carrying medication, such as Rock inhibitors, Wnt inhibitors or inhibitors of N-myristoyltransferase, such as many anti-malaria parasites medication, specifically IMP-1088 compound or NMT inhibitors, DDD85646 and DDD100870, and checkpoint inhibitors, or VLP, adjuvants, sodium bicarbonate to modify the acidic tumor cell environment and immune stimulators, such as TNF alpha, IL6, IL 17, toll like receptors, etc. and act as slow release polymeric drug release carrying medication to be attached to the tumor cells injected intravenously or intra-arterially 1-2 or more minutes ahead, permitting the nanoparticles to travel in the body and attach to the tumor cells that can be exposed to laser radiation, focused ultrasound, microwave or an alternating magnetic field to heat the nanoparticles and to produce a photoacoustic or thermoacoustic sound to be recorded by a photoacoustic or thermoacoustic transducer (an ultrasound receiver) located on the surface of the body to image the tumor while measuring the temperature generated at the tumor site by the laser or other energy source, such as focused ultrasound, microwave, or alternating magnetic field to image the temperature and the tumor in a 2-D and 3-D format, increasing the thermal radiation by a processor connected to the photoacoustic unit and thermal delivery unit to increase the tumor temperature and damage or kill the tumor cells at temperatures of 43 to 45-47 degrees C. and release cytoplasmic tumor antigens to attract dendritic cells, T-cells, and/or other killer cells to remove the tumor as they circulate in the body destroying the circulating or sessile tumor cells elsewhere in the body.

Figure 3:
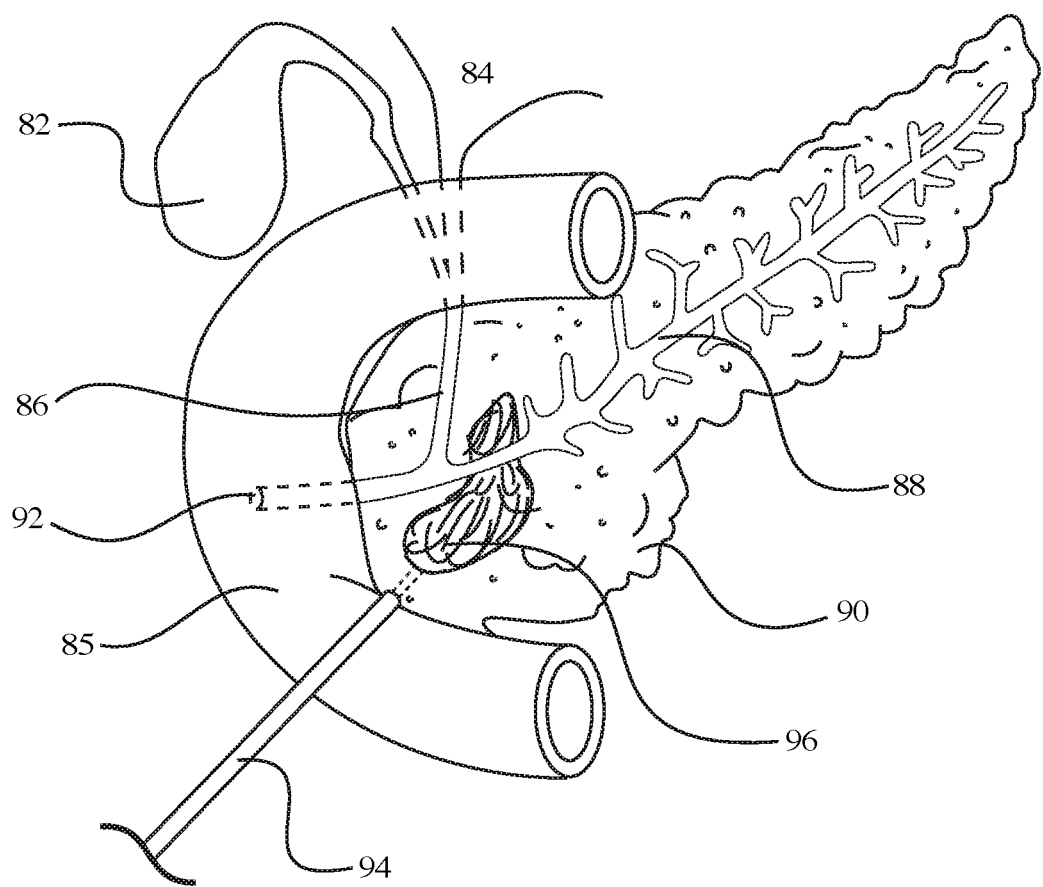
FIG. 3 is a diagrammatic illustration of several digestive organs of the human body showing the treatment of a tumor located in the pancreas with light emitted by a fiber optic device, according to yet another embodiment of the invention.

In one embodiment, where a tumor is inaccessible through the natural orifices, a fiber optic endoscope 94 is inserted through a small incision in the abdomen in the peritoneal cavity toward liver, spleen, pancreas, or kidney (see e.g., FIG. 3, which depicts a tumor 96 located in the pancreas 90) for diagnostic or therapeutic purposes using the laser thermal energy, to recognize the location of the tumor after injecting intravenously the antibody-coated pluralities of nanoparticles with cell penetrating peptides (CPP), activating CPP (ACPP), biotin, and/or streptavidin, or antibody-coated nanoparticles conjugated with (alpha)-cyclodextrin, (beta)-cyclodextrin, (gamma)-cyclodextrin, hydroxypropyl-b-cyclodextrin (bHPCD) conjugated with a thermosensitive polymer carrying medication and/or a gene, medication or immune stimulators. In this embodiment, shining the laser light over the suspected tumor/nanoparticle complex area creates a photoacoustic sound, which is imaged by a receiver or receivers located on the skin of the abdomen, then heating preferentially the antibody-coated pluralities of nanoparticles attached to the tumor cells by a laser, microwaves, or focused ultrasound, etc. damaging the tumor cells at a temperature of 37-43 degrees C., thereby releasing the conjugated medication, gene, toxins, Wnt inhibitors, or Rock inhibitors along with immune stimulators to kill and eliminate the cancer cells. In FIG. 3, several digestive organs of the human body are illustrated around the area of the pancreas 90 being treated by the fiber optic device 94, namely the gallbladder 82, liver 84, and duodenum 85. Also, illustrated in FIG. 3 are the bile duct 86, the pancreatic duct 88, and the opening 92 of the bile and pancreatic ducts 86, 88 into the duodenum 85.

In one embodiment, other tumors inside the body can be accessed through insertion of a fiber optic through the blood vessels, arteries, or veins of an organ (see e.g., FIG. 5) to induce a more organ specific diagnosis, and thermo-immune therapy without affecting the normal cells (e.g., in the brain, eye, or extremities) for tumors localized in the head and neck or urogenital organs, lung, etc.

In one embodiment, the thermotherapy is performed by injecting intravenously or intra-arterially, antibody or monoclonal antibody-coated pluralities of nanoparticles or solid lipid nanoparticles conjugated with thermosensitive polymers such as chitosan/medication or antibody coated nanoparticles conjugated with (alpha)-cyclodextrin, (beta)-cyclodextrin, (gamma)-cyclodextrin, hydroxypropyl-b-cyclodextrin (bHPCD, liposomes, solid lipid nanoparticles with nanowires, nanotubes, nanoshells, nanocages, periodic mesoporous organosilica nanoparticles conjugated with immune stimulator(s), such as interferon alpha, toll like receptors, IL 2, IL6, IL17, or VLP, adjuvants, sodium bicarbonate to modify the acidic tumor cell environment and CPP, with medication, inhibitors of N-myristoyltransferase, such as many anti-malaria parasites medication, specifically IMP-1088, or NMT inhibitors, DDD85646 and DDD100870, and Rock inhibitors, Wnt inhibitors which interferes with cellular proliferation or is injected through a major artery after insertion of a flexible laser fiber optic with a tube or a needle in a few steps of therapy: (a) administering the pluralities of antibody coated nanoparticles or liposomes, solid lipid nanoparticles, etc.; (b) applying thermal energy to the lesion and imaging it by a thermoacoustic unit to control the temperature to 40-43 degrees C., to release the medication from the nanoparticles or liposomes or solid lipid nanoparticles at the tumor site and irradiate the tumor cells with thermal energy; (c) continue administering antibody coated nanogel/nanoparticles, such as quantum dots or other nanoparticles such as gold or silica, magnetic, non-magnetic or hydrogels or liposomes or solid lipid nanoparticles (e.g., made of desired molar concentration and the ANG nanogel content) with or without various concentrations of a crosslinker, fibrinogen, adenosine diphosphate (ADP) to convert thrombinogen to thrombin and the fibrinogen to fibrin locally at the site of the tumor vasculature creating a precise localized vascular occlusion at the tumor site only while sparing the normal surrounding tissue.

In one embodiment, in contrast to the standard technique of embolization of a large vessel supplying a tumor which leads to indiscriminate closure of supply of a large area of an organ and damaging normal cells, the precise thermotherapy damages the endothelial cells and the tumor cells, releasing the medication from the antibody coated nanoparticles, namely releasing prothrombotic medication, checkpoint inhibitors, immune stimulators, anti-VEGF enhancing platelets binding and aggregation, and clotting; thus creating a discrete blood clot or thrombus, which obstructs the blood supply to the tumor, and starves the tumor from its blood supply while releasing the immune stimulating agents and medications slowly from the polymeric nanoparticle compounds and provide a long term local or systemic immunotherapy to the patient, and withdrawing blood after therapy one obtains increased tumor biomarkers proving the presence of a tumor even it was not initially not visible radiologically and administering antibody-coated pluralities of nanoparticles coated with dimethylacetyl-beta-cyclodextrin to inhibit excessive innate immune response locally and prevent excessive edema at the tumors surrounding site.

In one embodiment, one creates a precise local temperature increase and vascular occlusion at the site of the tumor and tumor vessels regardless of its location in the body and the size of the lesion, the injected antibody or monoclonal antibody-coated pluralities of nanoparticles conjugated with thermosensitive polymers, such as chitosan, and/or medication or antibody-coated nanoparticles conjugated with (alpha)-cyclodextrin, (beta)-cyclodextrin, (gamma)-cyclodextrin, hydroxypropyl-b-cyclodextrin (bHPCD, liposomes or solid lipid nanoparticles containing nanowires, nanotubes, nanoshells, nanocages, periodic mesoporous organosilica nanoparticles with immune stimulator(s), such as interferon alpha, toll like receptors, IL 2, IL6, IL17 or VLP, adjuvants, sodium bicarbonate to modify the acidic tumor cell environment and CPP, medication such as inhibitors of N-myristoyltransferase, such as many anti-malaria parasites medication, specifically IMP-1088 or NMT inhibitors, DDD85646 and DDD100870, Rock inhibitors, Wnt inhibitors are given intravenously but preferably through a feeding artery after insertion of a flexible laser fiber optic with a tube or just a small gauge needle in the vessel in different steps of therapy: (a) administering the pluralities of nanoparticles or combined with liposomes or solid lipid nanoparticles, etc.; (b) applying thermal energy to the lesion either with laser or focused ultrasound or an alternating magnetic field, microwave, etc. and using thermoacoustic imaging to control the energy delivery system to a temperature of 40-43 degrees C., to release the medication and damage the tumor cells membrane and the their endothelial cells membrane of their feeding vessels and capillaries supplying the tumor cells; (c) releasing from the antibody-coated nanogel/nanoparticles, such as quantum dots, liposomes, solid lipid nanoparticles, or other nanoparticles, such as gold or silica, magnetic, non-magnetic or hydrogels or liposomes or solid lipid nanoparticles or cyclodextrin, e.g., coated with a desired molar concentration, fibrinogen, adenosine diphosphate (ADP) to release them and to convert locally thrombinogen to thrombin and the fibrinogen to fibrin, producing a local thrombus locally at the site of the tumor vasculature, thus creating a precise vascular occlusion at the area of the tumor under observation. This is in contrast to the presently done embolization of a large vessel that not only supplies a tumor but large areas of an organ indiscriminatingly, such as in liver, brain, spleen, pancreas, lung, kidney, genitourinary system, or any other part of the body.

In one embodiment, after intravenous injection of antibody-coated nanoparticles, a localized thermotherapy is performed that damages the tumor cells and the endothelial cells membrane enhancing platelets binding and creating a discrete blood clot or thrombus, which obstructs the blood supply to the tumor precisely, and starves the tumor from oxygen and nutrition, while releasing from the nanoparticles, the innate body's immune stimulating compound agents, such as antibody coated nanoparticles conjugated with interferon alpha, toll like receptors, IL 2, IL6, IL17 and adjuvants and checkpoint inhibitors with CPP, anti-VEGF and medications, such as Rock inhibitors, Wnt inhibitors or inhibition of N-myristoyltransferase which interferes with cellular proliferation, to be released slowly for a long time from the polymeric compounds of the nanoparticles and provide a long term local or systemic immunotherapy to the patient followed with withdrawing blood after therapy to obtain tumor biomarkers for the future vaccine production.

In one embodiment, the injection of antibody or monoclonal antibody coated pluralities of nanoparticles conjugated with thermosensitive polymers, such as chitosan, and/or medications and antibody-coated nanoparticles conjugated with (alpha)-cyclodextrin, (beta)-cyclodextrin, (gamma)-cyclodextrin, hydroxypropyl-b-cyclodextrin (bHPCD) with anti-VEGF, immune stimulator(s), such as interferon alpha, toll like receptors, IL 2, IL6, IL17, or VLP, adjuvants, sodium bicarbonate to modify the acidic tumor cell environment and CPP is done through an artery after insertion of a flexible laser fiber optic with a tube in these different steps of therapy: (a) administering the pluralities of antibody-coated nanoparticles carrying checkpoint inhibitors, along with immune stimulators; (b) applying thermal energy to the lesion and simultaneous thermal imaging to control the temperature to 40-43 degrees C., to release the medication from the coating of the nanoparticles and damage and/or irritate the tumor cells membrane; (c) administering antibody-coated platelets from the patient's blood, coating the platelets with antibodies, or monoclonal antibodies and reintroducing the coated platelets into the patient to attach to the tumor and its associated vascular supply, creating a blood clot or thrombus, which obstructs the blood supply to the tumor, and nutritionally starves the tumor while the immune stimulating agents and medications continue to be released slowly for a long time from the polymeric compounds and provide a long term local or systemic immunotherapy to the patient, which can be also injected later in another body location to act as a vaccine.

In one embodiment, the thermotherapy of the injected antibody or monoclonal antibody-coated pluralities of nanoparticles conjugated with thermosensitive polymers, such as chitosan, and/or medication with immune stimulator(s) interferon alpha, toll like receptors, IL 2, IL 6, IL17, or VLP and CPP is done through an artery after insertion of a laser fiber optic with a tube in at least four different steps of therapy: (a) administering the pluralities of nanoparticles, (b) applying thermal energy to the lesion and imaging to control the temperature to 40-43 degrees C., to release the medication and irritate the tumor cells, (c) administering antibody coated nanogel/nanoparticles, such as quantum dots, or other nanoparticles such as gold or silica, magnetic, non-magnetic or hydrogel (e.g., made of desired molar concentration and the ANG nanogel content with or without various concentrations of a cross-linker) to attach to the tumor and its associated vascular supply, enhancing platelets binding and clotting, creating a blood clot or thrombus, which obstructs the blood supply to the tumor, and nutritionally starves the tumor while the immune stimulating agents and medications continue to be released slowly for a long time from the polymeric compounds and provide a long term local or systemic immunotherapy to the patient, and (d) withdrawing blood after therapy for increased tumor biomarker support for the existence of a tumor even it was not initially visible radiologically for creating a vaccine that can be injected at a later time subcutaneously.

In one embodiment, injection of antibody or monoclonal antibody-coated pluralities of nanoparticles conjugated with thermosensitive polymers, such as chitosan, and/or medication or antibody-coated nanoparticles conjugated with (alpha)-cyclodextrin, (beta)-cyclodextrin, (gamma)-cyclodextrin, hydroxypropyl-b-cyclodextrin (bHPCD) with immune stimulator(s), such as interferon alpha, toll like receptors, IL 2, IL6, IL17, or VLP, adjuvants, sodium bicarbonate to modify the acidic tumor cell environment and CPP, Wnt inhibitors or Rock inhibitors, anti-VEGF is done through an artery after insertion of a flexible laser fiber inside a tube imaged during its insertion in an artery for immune thermotherapy by: (a) administering the pluralities of antibody coated nanoparticles; (b) applying external or internal laser thermal energy, focused ultrasound, microwave or an alternating magnetic field to the lesion and thermoacoustic imaging to control the temperature to 40-43 degrees C., to release the medication and irritate the tumor cells and endothelial cells of the tumor; (c) administering antibody-coated nanogel/nanoparticles, such as quantum dots or other nanoparticles, such as gold or silica, magnetic non-magnetic or hydrogel (e.g., made of desired molar concentration and the ANG nanogel content with or without various concentrations of a photosensitizer) to attach to the tumor and its associated vascular supply, enhancing platelets binding and clotting, creating a blood clot or thrombus, which obstructs the blood supply to the tumor, and starves the tumor from its nutrition and oxygen while releasing immune stimulating agents and medications slowly in a continuous manner from the polymeric coated nanoparticles and providing a long term local or systemic immunotherapy to the patient; (d) withdrawing blood after therapy to obtain increased tumor biomarkers that support the presence of a tumor even it was not initially visible radiologically; and (e) administering antibody coated pluralities of nanoparticles coated with dimethylacetyl-beta-cyclodextrin to inhibit excessive innate immune response locally and prevent excessive edema at the tumors surrounding site.

In one embodiment, the laser fiber optic is inside a flexible tube through which one injects pluralities of antibody-coated nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) conjugated with thermosensitive polymers, such as PLA, PGA, chitosan, polyanhydride, polyanhydride, porous silicon carrying medication, siRNS, DNA, RNAi, CRISPR-cas9, inhibitors of N-myristoyltransferase, such as many anti-malaria parasites medication, specifically IMP-1088, NMT inhibitors, DDD85646 and DDD100870, Wnt inhibitors, or Rock inhibitors or CAR-t cells grown in cell culture and sensitized to the tumor antigen along with immune stimulation with VLP, toll-like receptors, adjuvants, sodium bicarbonate to modify the acidic tumor cell environment, toll like receptor 7/8 or interferons antibody-coated nanoparticles dendrimers, etc. can be injected in the circulation locally, intra-arterially to attach to the tumor cells and damage their cell membranes with thermal energy, such as laser, focused ultrasound, alternating magnetic field, or microwaves, etc. increasing the nanoparticles' and/or tumor cell's temperature to 40-43 degrees C. or more, and releasing the medication, immune stimulator, locally at the tumor site and enhance local immune therapy for a long duration and innate immune stimulation for a long period of time due to the release of the immune stimulators from the nanoparticles or porous silicone nano or microparticles, and withdrawing blood after therapy to measure increased tumor biomarkers and use them for vaccine therapy.

In one embodiment, E-selectin coated pluralities of antibody-coated nanoparticles are injected intravenously with cell penetrating peptides (CPP), activating CPP (ACPP), or antibody-coated nanoparticles conjugated with (alpha)-cyclodextrin, (beta)-cyclodextrin, (gamma)-cyclodextrin, hydroxypropyl-b-cyclodextrin (bHPCD), biotin, and/or streptavidin conjugated with medication and an Wnt inhibitor binds to sialylated carbohydrates on the surface proteins of certain leukocytes, increasing the nanoparticle temperature using a source of thermal energy to 40-43 degrees C. or more, and releasing the medication locally to the tumor cells and attracting neutrophils, monocytes, eosinophils, memory-effector T-like lymphocytes, and natural killer cells to further damage and remove the tumor cells.

In one embodiment, the CAR-T cells or killer cells are grown in a tissue culture with antibody-coated nanoparticles with cell penetrating peptides (CPP), activating CPP (ACPP), biotin, and/or streptavidin, or antibody-coated nanoparticles conjugated with (alpha)-cyclodextrin, (beta)-cyclodextrin, (gamma)-cyclodextrin, hydroxypropyl-b-cyclodextrin (bHPCD) which are conjugated with E-selectin to attach to the surface of the CAR-T cells and conjugated with VLP, adjuvants, sodium bicarbonate to modify the acidic tumor cell environment or other immune stimulating agents conjugated with polymeric nanoparticles or porous silicon nanoparticles coated with slow release polymers of PAL, GA, PLGA, or chitosan administered before and after thermotherapy to attach to the tumor cells and enhance cellular immune response after thermotherapy for 2 to 3 months or more as long as the slow release polymers last in the body.

In one embodiment, the CAR-T cells or killer cells are in grown tissue culture with antibody-coated nanoparticles with cell penetrating peptides (CPP), activating CPP (ACPP), biotin, and/or streptavidin, or (alpha)-cyclodextrin, (beta)-cyclodextrin, (gamma)-cyclodextrin, hydroxypropyl-b-cyclodextrin (bHPCD) which are conjugated with E-selectin to attach to the surface of the CAR-T cells and a medications, toxins, enzymes, TNF, TRAIL, VLP, adjuvants, sodium bicarbonate to modify the acidic tumor cell environment, toxins, propranolol, a beta blocker, or an anti-VEGF to inhibit the tumor's vascular growth and can be injected intra-arterially at less than $\frac{1}{10}$-$\frac{1}{50}$th of the quantities used systemically, through laser fiber optic tube slowly before and after thermotherapy of a localized tumor, to be released slowly to attack repeatedly, the tumor cells in the specific organ, and induce a localized lasting immune response or induce an immune response in the body to eliminate potential existing tumor cells or invisible metastasis and autoimmune response.

In one embodiment, the release of antibody-coated pluralities of nanoparticles with cell penetrating peptides (CPP), activating CPP (ACPP), biotin, and/or streptavidin or antibody-coated (alpha)-cyclodextrin, (beta)-cyclodextrin, (gamma)-cyclodextrin, hydroxypropyl-b-cyclodextrin (bHPCD) are observed after intra-arterial injection with an imaging system such as MRI, or ultrasound to verify the position of the tumor that is being treated with controlled thermotherapy using electromagnetic radiation, microwave, radiofrequency (RF), or focused ultrasound or alternating magnetic field or an electric field, and the lesion is imaged by a photoacoustic or thermoacoustic imaging system, the temperature is controlled by the thermoacoustic unit connected via a processor to the thermal delivery system to control thermal energy delivery, and prevent over cooking of the tissue via the thermoacoustic imaging system that measures the temperature rise 100 times per second and is in communication with the thermal energy delivery device so that the desired temperature of, for example, 41-43 degrees C. is achieved or maintained for a preferred time.

In one embodiment, the laser fiber optic with the tube is inserted through the carotid artery to reach either sides of the CNS harboring a tumor, such as glioblastoma, etc. to release pluralities of antibody-coated nanoparticles with cell penetrating peptides (CPP), activating CPP (ACPP), biotin, and/or streptavidin, Wnt or Rock inhibitors or antibody coated (alpha)-cyclodextrin, (beta)-cyclodextrin, (gamma)-cyclodextrin, hydroxypropyl-b-cyclodextrin (bHPCD) conjugated with polymers, such as PLA or PGA, nanoparticles of porous silicon, chitosan attached with medication or immune stimulators in the circulation so that the majorities of nanoparticles reach at a high concentration at the tumor site and are released as needed by application of internal or external thermal energy such as laser, focused ultrasound, alternating magnetic field, etc. under observation of the tumor's temperature kept at 41-43 degrees C. for a desired time while the thermal energy delivery system is controlled via a processor that connects the thermoacoustic imaging unit that measures and records to the thermal energy delivery unit so that the predetermined temperature is achieved inside the tumor and maintained for a desired time to prevent over-cooking of the normal tissue.

In one embodiment, the laser fiber optic with the tube is inserted through the femoral artery through the abdomen and moved toward any organ, such as the kidney, intestine, spleen, liver, heart, lung or reaches the carotid artery or any other part of the brain, to release pluralities of antibody-coated nanoparticles in the circulation so that the nanoparticles/medications reach a higher concentration at the tumor site than would be reached when injected intravenously where most of the nanoparticles/medications are taken up by the liver and spleen's reticuloendothelial cells before reaching the tumor site.

In one embodiment, the laser fiber optic with the tube is inserted through the femoral or radial/femoral artery (see FIG. 7) to reach the tumor in the bone or extremities to release the pluralities of antibody-coated nanoparticles/medication/propranolol with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) conjugated with thermosensitive polymers such as PLA, PGA, PLGA, chitosan, polyanhydride or antibody-coated nanoparticles/microparticles of porous silicon carrying medication, siRNS, DNA, RNAi, CRISPR-Cas9, Wnt inhibitors, or Rock inhibitors or CAR-t cells grown in cell culture and sensitized to the tumor antigen along with immune stimulation with VLP, adjuvants, sodium bicarbonate to modify the acidic tumor cell environment, toll like receptors 7/8 or interferons, TNF alpha, IL2 can be injected in the circulation locally to attach to the tumor cells so as to then damage them with thermal energy such as laser, focused ultrasound, alternating magnetic field, or microwaves by increasing the nanoparticles temperature to 40-43 degrees C. or more and releasing the medication, and propranolol locally to the tumor cells.

Figure 7:
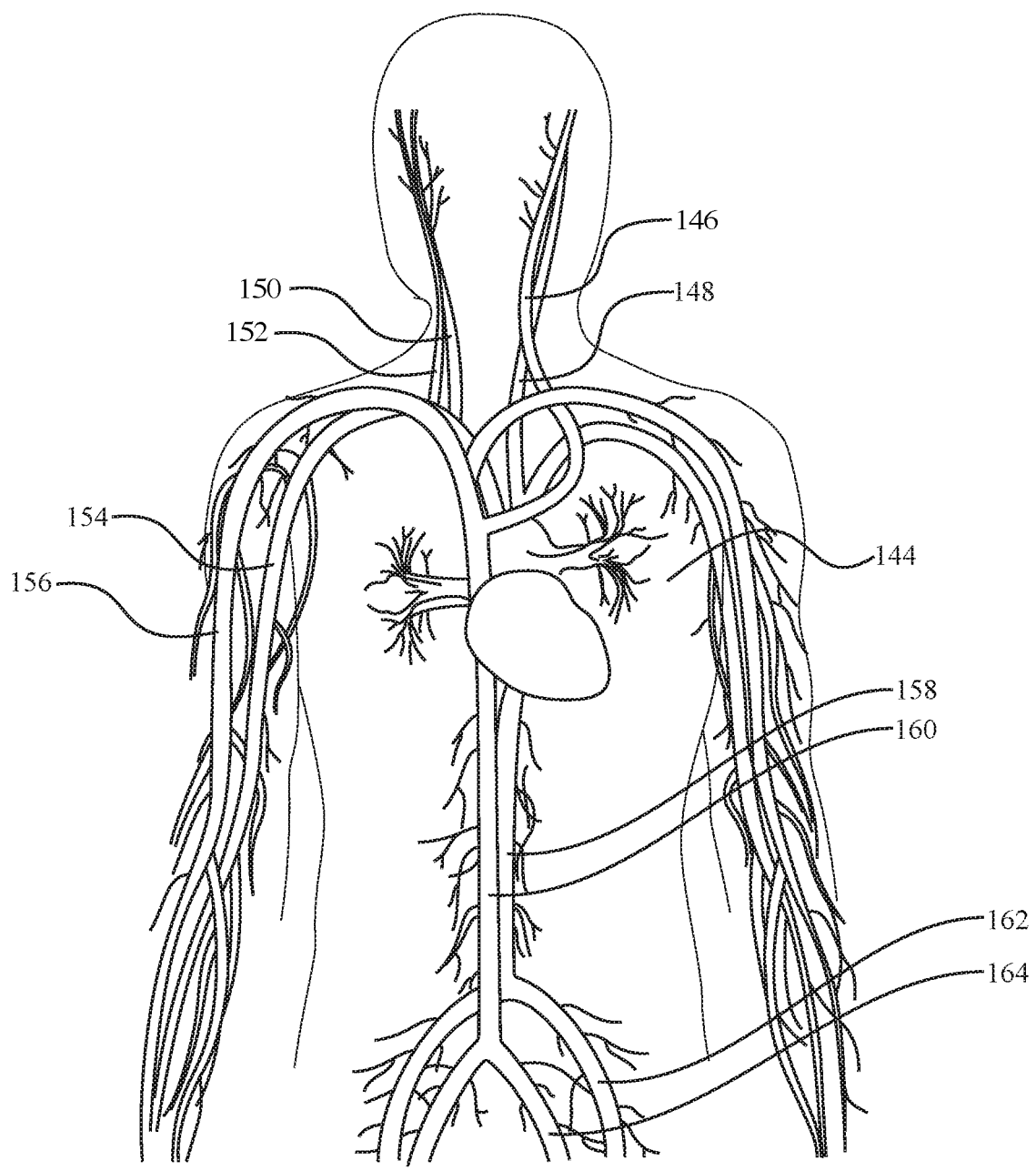
FIG. 7 is a diagrammatic illustration of the human circulatory system in the upper portion of the body.

The human circulatory system 144 is represented in diagrammatic form in FIG. 7. In FIG. 7, it can be seen that the circulatory system 144 includes left and right common carotid arteries 146, 150, left and right internal jugular veins 148, 152, a right brachial artery 154, a right vein 156, an abdominal aorta artery 158, an inferior vena cava 160, a left femoral artery 162, and a left common iliac vein 164. As described above, in one or more embodiments, the laser fiber optic with the tube carrying the antibody-coated nanoparticles may be inserted through one of the arteries or veins 146-164 depicted in FIG. 7.

In one embodiment, the flexible laser fiber optic with the tube is inserted through the radial arteries, to reach the lung or the heart to deliver pluralities of antibody-coated nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) conjugated with thermosensitive polymers, such as PLA PGA, chitosan, polyanhydride carrying medication, siRNS, DNA, RNAi, CRISPR-Cas9, Wnt inhibitors, or Rock inhibitors or CAR-t cells grown in cell culture and sensitized to the tumor antigen along with immune stimulation with VLP, adjuvants, sodium bicarbonate to modify the acidic tumor cell environment, toll-like receptors 7/8 or interferons can be injected in the circulation locally to attach to the tumor cells so as to then damage them with thermal energy such as laser, focused ultrasound, or alternating magnetic field by increasing the nanoparticles temperature to 40-43 degrees C. or more and releasing the medication locally to the tumor cells.

In one embodiment, for example, a brain tumor is located in the right or left temporal lobe of the brain, and the laser fiber/tube is inserted through the carotid artery (see FIG. 5) for delivery of pluralities of antibody-coated nanoparticles/medication with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) conjugated with thermosensitive polymers such as PLA, PGA, chitosan, and polyanhydride or porous silicon nanoparticles and/or microparticles carrying medication, siRNS, DNA, RNAi, CRISPR-Cas9, Wnt inhibitors, checkpoint inhibitors, or Rock inhibitors or CAR-t cells grown in cell culture and sensitized to the tumor antigen along with immune stimulation with VLP, adjuvants, sodium bicarbonate to modify the acidic tumor cell environment, toll-like receptors 7/8 or interferons, the antibody-coated nanoparticles can be injected in the circulation locally to attach to the tumor cells so as to then damage them with thermal energy, such as laser, focused ultrasound, or alternating magnetic field, thereby increasing the nanoparticles temperature to 40-43 degrees C. or more and releasing the medication locally to the tumor cells and damage the tumor cells and combining it with humoral and cellular immune therapy, while a drainage tube is placed in the jugular vein of the right or left side to collect cellular debris and toxins and pass it through a dialysis system and return the cleansed blood back to the patient eliminating the adverse effects of chemotherapy and immune therapy to the patient, thus creating a concept of lasting therapeutic intervention with potential of ease of re-injection as vaccine and re-stimulation of the immune system.

For example, as shown in FIG. 5, a laser fiber optic device 124 may be inserted through the internal carotid artery 120 in the head of a person so as to treat a tumor 118 in the brain 112 of the person by emitting light pulses generated a light source 126. Also, as shown in FIG. 5, additional tumors 114, 116 are located in the brain 112 of the person. The additional tumors 114, 116 may also be treated using a laser fiber optic device inserted through a nearby artery in the head of the person. As one example, a fiber optic device may be inserted through the external carotid artery 122 in the head of the person so as to treat the tumor 116. Also, as shown in FIG. 5, a photoacoustic receiver 128 with cord 130 may be placed against the head of the person in order to record a photoacoustic/thermoacoustic response resulting from the thermal expansion of nanoparticles attached to the tumor (e.g., attached to tumor 118 in the brain 112) that are heated by the laser light pulses from the fiber optic device 124. The nanoparticles may be delivered to the tumor site prior to the heating thereof by a tube attached to the fiber optic device 124.

In one embodiment, to prevent a severe autoimmune response after tumor immunotherapy, one uses the return blood, for example, from the jugular vein for extracorporeal plasmapheresis, the nanoparticle assisted thermotherapy and imaging system to apply heavy thermal energy to a tube containing blood cells and to achieve a temperature as high as 60 degrees C. to kill the sensitized immune cells containing nanoparticles. Blood is then passed through a dielectrophoresis system to characterize and remove dead or live T-cells, sensitized killer cells, and tumor cells prior to re-infusing blood in the patient while simultaneously administering antibody-coated nanoparticles conjugated with anti-inflammatory agents, including biologics and mycophenolic acid to reduce the severe autoimmune response often seen after tumor immunotherapy.

In one embodiment, the pluralities of antibody-coated nanoparticles or dendrimers with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) conjugated with thermosensitive polymers such as PLA, PGA, PLGA, chitosan, polyanhydride, anhydride or porous silicon nanoparticles and/or microparticles carrying medication and immune stimulators, siRNS, DNA, RNAi, to modify the genetic mutation of the tumor cells using CRISPR-Cas9 to reduce the expression of checkpoint proteins without the use of a viral vector, and can be injected intravenously or preferably intra-arterially in the circulation at a dose far below the systemically used non-toxic dose so that the nanoparticles travel and attach to the tumor cells directly in an organ and eliminate the tumor cells or modify their genetic component without using a vector using controlled thermotherapy and using CRISPR-Cas9 mediated Homology—Independent Targeted Integration (HITI) or Homology Directed Repair (HDR).

In one embodiment, the pluralities of antibody-coated nanoparticles with cell penetrating peptides (CPP), activating CPP (ACPP), biotin, and/or streptavidin or antibody-coated nanoparticles/medication conjugated with (alpha)-cyclodextrin, (beta)-cyclodextrin, (gamma)-cyclodextrin, hydroxypropyl-b-cyclodextrin (bHPCD) conjugated with thermosensitive polymers, such as PLA, PGA, PLGA, chitosan, polyanhydride, anhydride or porous silicon nanoparticles and/or microparticles carrying medication, siRNS, DNA, RNAi to modify the genetic mutation of the tumor cells using CRISPR-Cas9 to reduce the expression of checkpoint proteins without the use of a viral vector but combined with Wnt inhibitors, or Rock inhibitors/antibody-coated nanoparticles can be injected intravenously or preferably intra-arterially in the circulation at a dose far below the systemically non-toxic dose or less than 1/100 the non-toxic dose used systemically so that the nanoparticles travel directly to the tumor cells locally, attach to them in an organ and eliminate the tumor cells or modify their genetic component by using CRISPR-Cas9 mediated Homology—Independent Targeted Integration (HITI) or Homology Directed Repair (HDR) component without using a viral vector.

In one embodiment, the pluralities of magnetic or paramagnetic coated nanoparticles, or magnetic luminescent porous SI nanoparticles and/or microparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) are administered intra-arterially and heated at the tumor site either with the laser light internally with the use of a fiber optic or from outside with a focused ultrasound in a compressive non-thermal focused mode to strip from the nanoparticles, the coating conjugated with a gene, medication or Wnt or Rock inhibitors, and then heated to 40-43 degrees C. with the thermal mode of a focused ultrasound, microwaves, or laser creating a thermal effect on the tumor while the degree of the temperature is imaged using a photoacoustic or thermoacoustic thermal imaging system where the receiver is attached to the surface of the skull, neck, or body elsewhere or the use of an MRI to locate the tumor and measure the tumor/nanoparticle temperature. The control of the temperature is achieved with an operative connection between the thermoacoustic unit and the thermal delivery unit (e.g., a hardware and software-based connection), which controls the thermal energy depending on what temperature is needed and dialed on the system.

In one embodiment, the thermal energy is provided with either an alternating magnetic field or a microwave unit of an RF unit or focused ultrasound while the thermoacoustic system controls the desired energy level and duration with a hardware/software-based connection to thermal delivery system.

In one embodiment the tumor/nanoparticles are heated to the temperature of 37-40 degrees C. or 40-43 degrees C. and maintained for 1 second to 10 minutes as needed to damage the tumor cells and release the medication.

In one embodiment, one uses the laser fiber optic/tube to induce a localized immunotherapy by administering pluralities of antibody-coated nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) conjugated with checkpoint inhibitors, and or monoclonal antibodies or aptamers, or immune stimulators with or without injection of a limited number of CAR-T cells to phagocytize the damaged tumor cells.

In one embodiment, the CAR-T cells are modified with RNAi or sRNA, etc. in vitro to silence the immune checkpoints in them so that after their administration they do not respond to the tumor cell production of checkpoint inhibitors and attack the tumor cells where they find them.

In one embodiment the pluralities of antibody coated nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) are conjugated with viral-like particles (VLP), adjuvants or toxin, viruses not only to damage the tumor cells but induce localized immune response, inflammation to attract the patient's lymphocytes, and killer cells to remove the dead tumor cells and provide systemic immunity to circulating tumor cells.

In one embodiment, the blood returning from the brain, etc. where the tumor is located is withdrawn through the jugular vein, passed through a dialysis or dielectrophoresis system to clean the blood from the dead cells and remove checkpoint inhibitors, the VLP, adjuvants, or other toxins produced by the dead tumor cells to prevent a cytokine storm.

In one embodiment, after the thermo-immune therapy, Wnt inhibitors, or Rock inhibitors are administered to the tumor by conjugating them with pluralities of antibody-coated nanoparticles/medication, with cell penetrating peptides (CPP), activating CPP (ACPP), biotin, and/or streptavidin or antibody coated nanoparticles conjugated with nanoparticles coated with (alpha)-cyclodextrin, (beta)-cyclodextrin, (gamma)-cyclodextrin, hydroxypropyl-b-cyclodextrin (bHPCD). Administering antibody coated dimethylacetyl-beta-cyclodextrin after therapy inhibits excessive innate immune response and prevent excessive edema at the tumors surrounding site, to reach the tumor area and prevent excessive inflammation and edema.

In one embodiment, the tumor is located in the eye, nose, throat, or any part of the neck and head, mucosa, skin, tongue, throat, eye, esophagus, thyroid, salivary or lacrimal glands, bladder, genitourinary system, nose, brain that can be reached through the natural body orifices or through an artery or a vein using laser tube delivery device with its fiber optic for laser delivery to the tumor.

Figure 2:
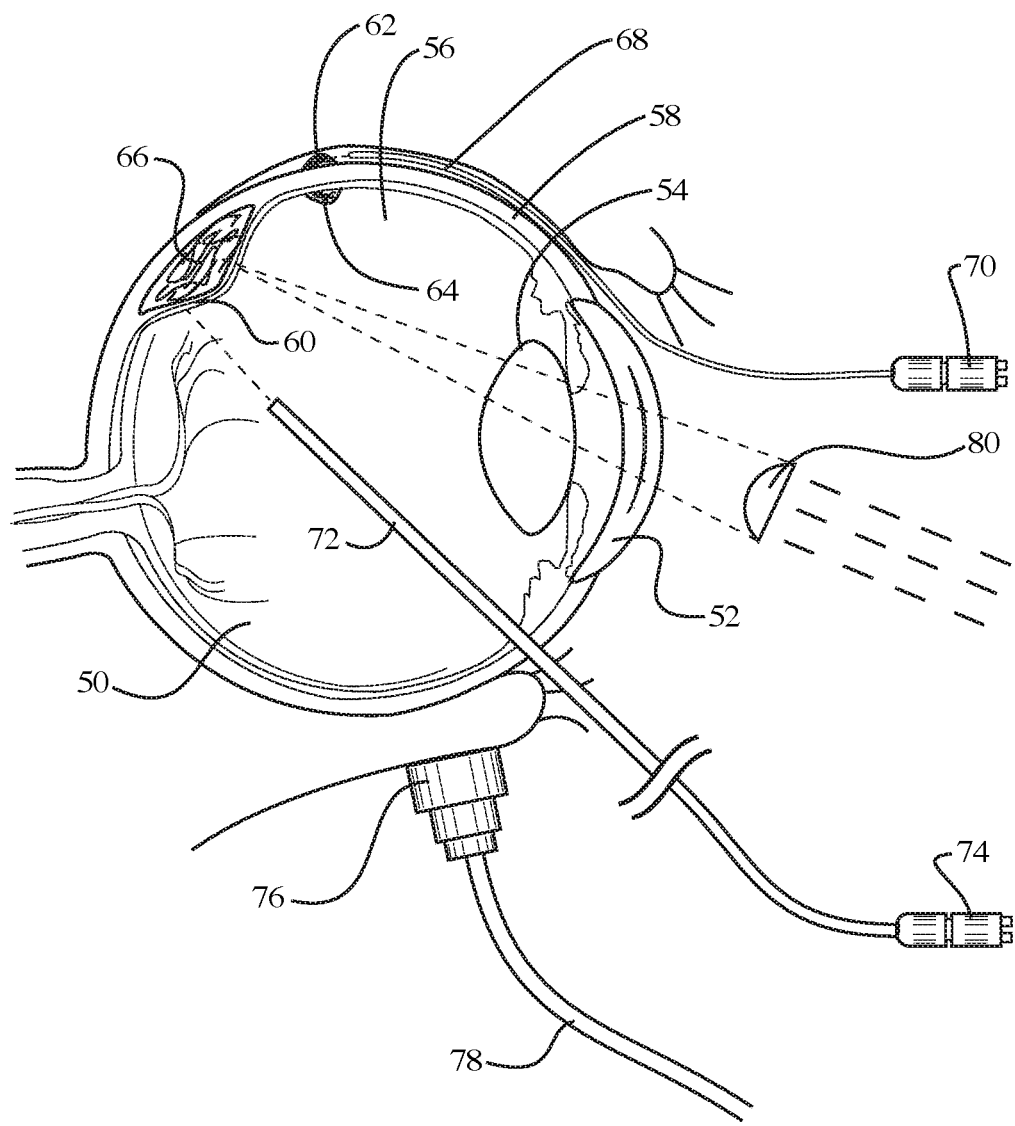
FIG. 2 is a diagrammatic illustration of a human eye showing the treatment of tumors located in several areas of the eye with light emitted by fiber optic devices, according to another embodiment of the invention.

For example, as shown in FIG. 2, one laser fiber optic device 68 may be inserted through the conjunctiva so as to treat a tumor 62 located on the sclera 58 of the eye 50 by emitting light pulses generated a light source 70. In FIG. 2, it can be seen that the eye 50 includes a cornea 52, a lens capsule 54, a vitreous cavity 56, a sclera 58, and a retina 60. In addition, as also shown in FIG. 2, another fiber optic device 72 with light source 74 may be inserted into the vitreous cavity 56 of the eye 50 so as treat another tumor 66 located proximate to the retina 60 of the eye 50. Alternatively, or in addition to the internally disposed fiber optic device 72, a light source 80 located outside of the eye 50 may be used to deliver light pulses for treating the tumor 66. In FIG. 2, it can be seen that the eye 50 contains another tumor 64 on the retina 60, which may be treated with the fiber optic device 72 or the external light source 80. Also, as shown in FIG. 2, a photoacoustic receiver 76 with cord 78 may be placed against the eyelid of the eye 50 in order to record a photoacoustic/thermoacoustic response resulting from the thermal expansion of nanoparticles attached to the tumor (e.g., attached to tumor 66 in the eye 50) that are heated by the laser light pulses from a fiber optic device 72. As described above, the nanoparticles may be delivered to the tumor site prior to the heating thereof by a tube attached to the fiber optic device 72.

Figure 4:
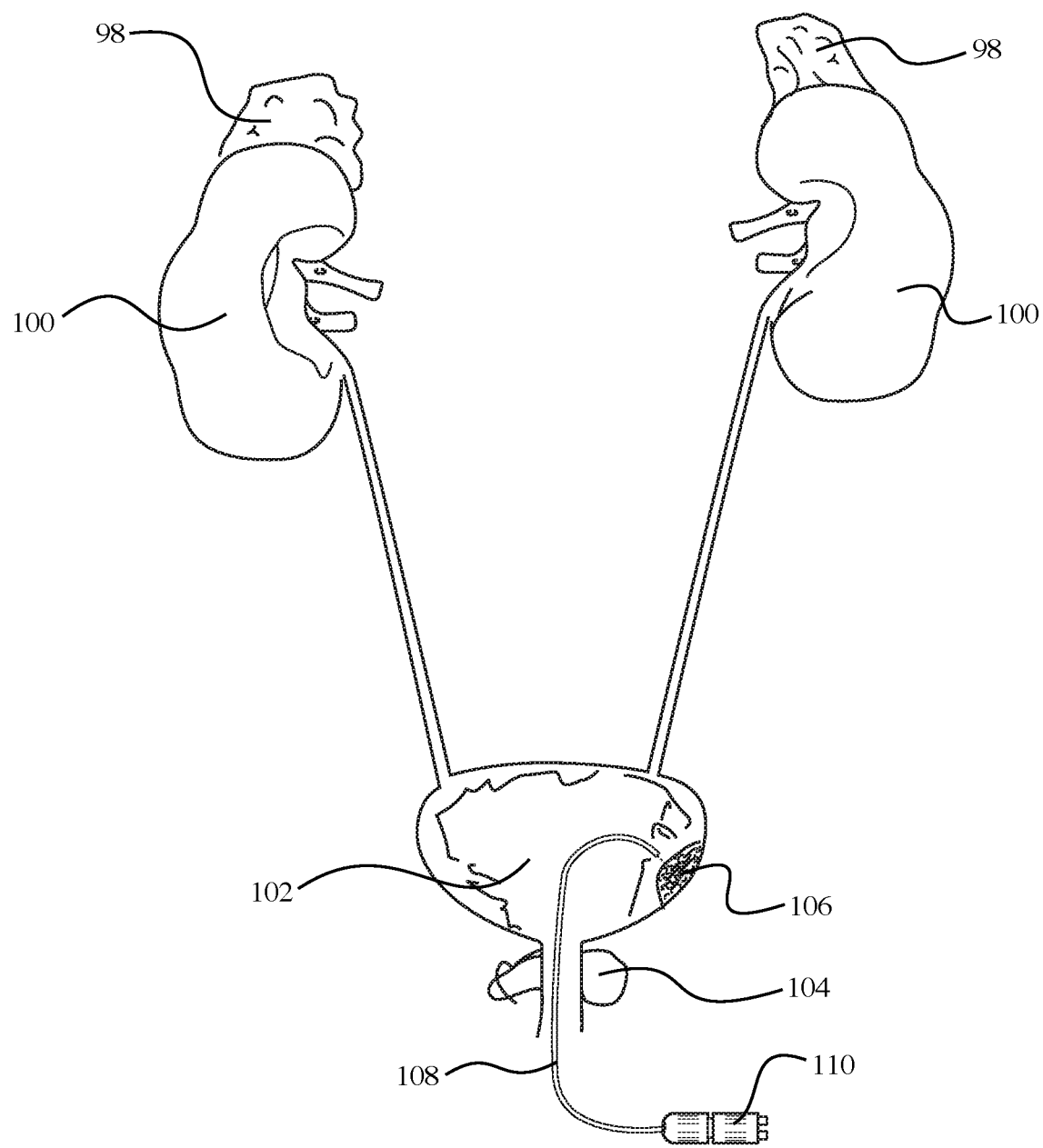
FIG. 4 is a diagrammatic illustration of the urinary system of the human body showing the treatment of a tumor located in bladder with light emitted by a fiber optic device, according to still another embodiment of the invention.

As another example, as shown in FIG. 4, a laser fiber optic device 108 may be inserted through the urethra so as to treat a tumor 106 located in the bladder 102 by emitting light pulses generated a light source 110. As illustrated in FIG. 4, in addition to the bladder 102, it can be seen that the renal/urinary system illustrated therein further includes the suprarenal glands 98, kidneys 100, and prostate 104.

Figure 6:
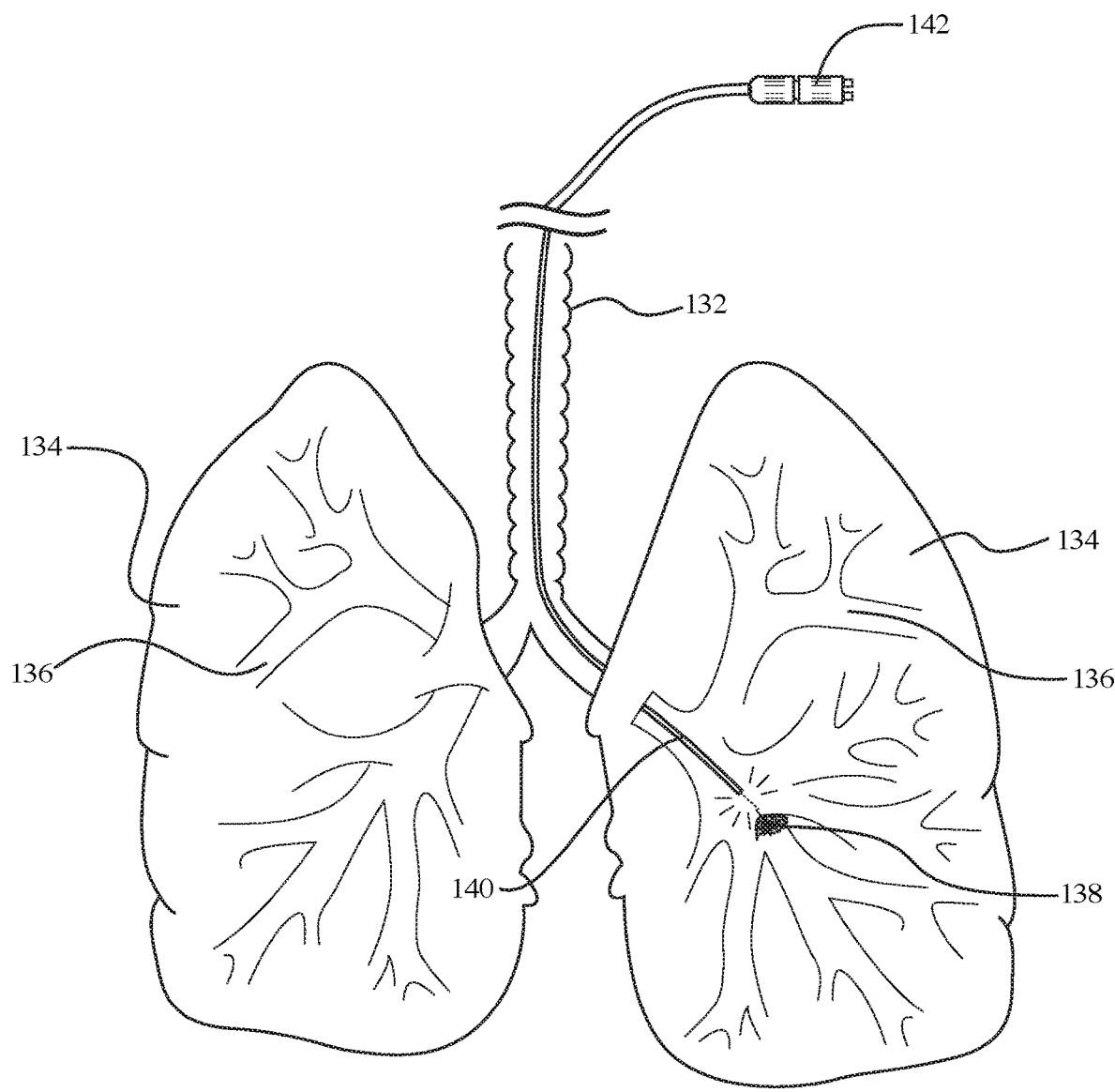
FIG. 6 is a diagrammatic illustration of the lungs and trachea of the human respiratory system showing a tumor located in one of the lungs and the treatment of the tumor with light emitted by a fiber optic device, according to still another embodiment of the invention.

As yet another example, as shown in FIG. 6, a laser fiber optic device 140 may be inserted through the trachea 132 and bronchi 136 so as to treat a tumor 138 located in the lung 134 by emitting light pulses generated a light source 142.

In another embodiment, polymeric antibody-coated nanoparticles or polysaccharide or synthetic polymers conjugated with biomarkers and nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) are administered to enhance a vaccination effect and are taken up by antigen presenting cells.

In one embodiment, simultaneous administration of vaccine adjuvants with antibody-coated pluralities of nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) conjugated tumor lysates, VLPs, or purified antigen with or without adjuvant, interferon stimulating genes, toll-like receptors 7/8 using thermosensitive polymers or without the use of thermal energy with antibody-coated chitosan or other slow release antibody-coated nanoparticles of biodegradable polymeric nanoparticles, lactic acid, glycolic acid, or combination of them. PLGA nanoparticles or polycaprolactone, polyanhydrides, acrylamide, anhydride, or porous silicon nanoparticles and/or microparticles, etc. stimulates immune cell response initially during the thermotherapy and afterwards keep immune cell, dendritic cells, T cells, activated natural killer (NK) cells stimulation active for 3-6 months after the initial thermotherapy treatment or can be repeated as a vaccination every 6 months to kill tumor cell recurrences locally or elsewhere in the body.

In another embodiment, the thermotherapy is associated with local, intra-arterial injection supplying an organ having the tumor, administration of immune stimulating agent conjugated with antibody-coated pluralities of nanoparticles or porous silicon nanoparticles and/or microparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) with tumor lysates, VLPs, or purified antigens with or without adjuvants, interferon stimulating genes, toll-like receptors 7/8 using thermosensitive polymers or with or without the use of thermal energy with antibody-coated polymers, such as chitosan or other slow release antibody-coated nanoparticles of biodegradable polymeric nanoparticles, lactic acid, glycolic acid, PLGA nanoparticles, anhydride, etc. so as to expose mostly the local invasive tumors, such as glioblastoma, are bathed with the antibody-coated nanoparticles rather than the entire body, where the antibody coated nanoparticles or the immune stimulators could produce an adverse effect, such as in liver or kidney, etc.

In one embodiment, the local intra-arterial immune stimulatory therapy and thermotherapy is associated with culture grown immune cell therapy, where the number of CAR-T cell administration is kept far below ⅒ of what would be needed for the whole body intravenous administration as is done routinely, thus reducing the chance of an auto immune response.

In one embodiment, the venous drainage of an organ can be cannulated to remove blood containing the excessive cellular immune cells or nanoparticles, associated with checkpoint inhibitors or medications cleansed from the cellular elements and nanoparticles and re-infused to the patient's body to reduce or eliminate adverse effect of the systemic medication as is done routinely.

In one embodiment, Phosphoinositides 3-Kinase are involved in cell signaling pathways and play an important role in cellular growth, translation and metabolism. In general the Phosphoinositides 3-Kinase are a part of PI4K/AkT/mTOR pathway which are involved in tumor growth. Their inhibition has been an important goal of cancer therapy. However, until now, the PI4K/Aky/mTOR pathway inhibitors and other isoforms of the PI3Ks with their sub-units known as p110 alpha, beta, gamma and delta inhibitors such as wortmannin, Idelalisib, Alpelesib, Buperlasib, etc. are administered systemically and not selectively, locally, intra-arterially or intravenously along with pluralities of antibody or monoclonal antibody-coated nanoparticles or antibody-coated nanoparticles conjugated with (alpha)-cyclodextrin, (beta)-cyclodextrin, (gamma)-cyclodextrin, hydroxypropyl-b-cyclodextrin (bHPCD) at far lower doses than used for systemic medication, while enhancing cellular permeability with localized thermotherapy.

In one embodiment, similarly Phosphoinositides 3-Kinase or PI4K inhibitors or Shep 2 inhibitors affect growth of certain tumors, such as intestinal, brain, lung, etc. cancers, but also affect proliferation of macrophages which interestingly support the proliferation of the tumor cells, this process of inhibition of macrophage proliferation can be countered with local administration of Phosphoinositides 3-Kinase or PI4K inhibitors, inhibitors or Shep 2 inhibitors by antibody-coated nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) are conjugated with viral-like particles (VLP), toxins, or lytic viruses not only to damage the tumor cells but induce localized immune response, inflammation to attract the patient's lymphocytes, and killer cells and antibody-coated nanoparticles and slow release polymers of chitosans, polycaprolactone, lactic, and glycolic acid, anhydride or porous silicon nanoparticles and/or microparticles administration conjugated with immune stimulators and checkpoint inhibitors, and immune stimulators such as VLP or toxins enhancing innate humoral and other cellular response, such as natural killer cell T-lymphocytes, etc.

In one embodiment, pluralities of antibody or monoclonal antibody-coated nanoparticles or antibody-coated nanoparticles conjugated with (alpha)-cyclodextrin, (beta)-cyclodextrin, (gamma)-cyclodextrin, hydroxypropyl-b-cyclodextrin (bHPCD) are conjugated with thermosensitive nanoparticles conjugated with Phosphoinositides 3-Kinas inhibitors or in combination with AkT/mTOR inhibitors carrying immune stimulating agents, such as interferons, toll like receptors, toxins, or VLP or simultaneous checkpoint inhibitors, such as PD-1, CTLA-4 or Jagged1, which can be injected into the circulation intravenously or intra-arterially, and can be released with the medication specifically at the site of the malignant tumors at a controlled temperature of 40-43 degrees C. or applied locally or externally using laser light, focused ultrasound, or microwaves, RF, or an alternating magnetic field along with magnetic nanoparticles, or magnetic luminescent porous silicon nanoparticles and/or microparticles etc., and control of the energy by a thermoacoustic imaging unit to treat the lesions by inhibiting the PI4K/AkT/mTOR Shp 2 pathway locally and enhance vascular and cellular permeability with localized thermotherapy and simultaneously enhance systemic humoral and cellular response to kill the tumors.

In one embodiment, the treatment of cancer, such as brain cancer (e.g., glioblastoma) or hematological malignant cells, such as lymphoma or leukemia, or breast cancer of head and neck, eye, skin or mucosa cancers or lung or intestinal tract cancers, or genitourinary cancers in cases where the cancers have become therapy resistant to one medication, it requires administration of a combination of medication that when applied together, may be more beneficial to the patients, but also enhance each other's side effects of medications in these cases. In one embodiment, pluralities of antibody or monoclonal antibody-coated nanoparticles or antibody coated nanoparticles conjugated with (alpha)-cyclodextrin, (beta)-cyclodextrin, (gamma)-cyclodextrin, hydroxypropyl-b-cyclodextrin (bHPCD) are conjugated with thermosensitive nanoparticles conjugated with Phosphoinositides 3-Kinas inhibitors, or in combination with AkT/mTOR inhibitors, such as everolimus, or Wnt inhibitors or Rho inhibitors carrying immune stimulating agents, such as interferons, toll-like receptors, toxins, or VLP or simultaneous checkpoint inhibitors, such as PD-1, CTLA-4 or Jagged1 can be injected into the circulation intravenously or intra-arterially to be released specifically the medication at the site of the malignant tumors at a controlled temperature of 40-43 degrees C. or applied locally or externally using laser light, focused ultrasound, or microwave, RF or an alternating magnetic field along with magnetic nanoparticles, etc., and control of the energy by a thermoacoustic imaging unit treat the lesions by inhibiting the PI3K/AkT/mTOR or Shp 2 pathway locally and enhance vascular and cellular permeability with localized thermotherapy and simultaneously enhance systemic humoral and cellular response to kill the tumors.

With respect to gene delivery, the inventive method may be used in cancer therapy, but is not limited to such use; it will be appreciated that the inventive method may be used for gene delivery in general with antibody coated pluralities of nanoparticles with cell penetrating peptide (CPP), activating CPP (ACPP), biotin, streptavidin. For example, the inventive method facilitates cellular gene uptake by current methods that lack a thermal energy component, such as electroporation, quantum dot delivery, etc. The controlled and precise application of thermal energy enhances gene and medication transfer to any cell, whether the cell is a neoplastic cell, a pre-neoplastic cell, or a normal cell by using CRISPR-cas9 mediated Homology—Independent Targeted Integration (HITI) or Homology Directed Repair (HDR).

The inventive method provides in vitro and in vivo precision immunotherapy to decrease or eradicate a malignant neoplasm at an early stage of the disease. This method provides a vaccination effect periodically to prevent at least the same kind of cancer or to treat recurrences.

One embodiment is a method for evaluating treatment outcome in a patient having a genetic predisposition for a malignant neoplasm before clinical manifestation of the neoplasm can be seen radiographically. The method permits visualization of any tumor, whether located externally on a patient's body or located internally in the body, and as small as 2 mm in diameter, producing a biomarker, either a biomarker specific for the tumor or a general biomarker.

In general, a biomarker indicates a disease process. As subsequently described, a biomarker can be a protein, antigen, enzyme, hormone, carbohydrate, toxin, DNA, an organism such as bacteria, tumor cell, exosome, or indirectly an antibody, present in a liquid biopsy specimen. It can be produced by the plasma cells, against a tumor antigen, etc.

The method uses antibodies conjugated with nanoparticles with cell penetrating peptides (CPP), activating CPP (ACPP), biotin, and/or streptavidin, which include but are not limited to quantum dots, with the conjugated form collectively termed functionalized nanoparticles, that are heated under specified conditions to produce a photoacoustic or thermoacoustic signal that is then then recorded and visualized to locate the tumor to which the nanoparticles are attached. Nanoparticles may be used for qualitative and quantitative assessment of an analyte in the blood or other tissue using photoacoustic/thermoacoustic technology, U.S. Pat. No. 8,554,296. As previously stated, as used herein, unless specifically stated otherwise, nanoparticles include but are not limited to quantum dots.

Early stage small neoplastic cells produce biomarkers that are either specific to the tumor cells or that represent the body's response to the tumor as an antibody. The biomarkers can be proteomic, genetic, epigenetic or glycomic biomolecules. These biomolecules can be recognized in the patient's tissue samples or in the blood or fluids. Their existence can be demonstrated thus far chemically using, e.g., immunoassay or PCR methods. Quantitation of these biomarkers is also important to determine disease progression and prognosis of the disease.

Biomarkers for many diseases are found in the blood. As subsequently disclosed, biomarkers detected in a liquid biopsy sample are used to generate antibodies against them using known methods in the art. The anti-tumor antibodies are used to coat nanoparticles with cell penetrating peptides (CPP), activating CPP (ACPP), biotin, and/or streptavidin in the inventive method, where a lesion can be imaged regardless of the lesion size or location in the body. The method is not limited to tumor detection and/or therapy. As only one example, detecting an antibody against anti-beta-amyloid protein present in Alzheimer's disease in a liquid biopsy specimen, the method renders the plaque visible with the nanoparticles and accessible to the inventive treatment. As another example, the method can also be used to detect and/or treat inflammatory processes, etc.

The inventive method is applicable to any processes or diseases that produce a biomarker detectable in a liquid biopsy specimen. It is applicable to a lesion including an abscess, an ulcer, a tumor either benign or malignant, an ischemic area of a stroke and/or an area of the brain affected by a stroke whether visible or microscopically.

Well over a thousand proteins are differentially expressed in human cancers and thus may serve as biomarkers. Such proteins play a role in cancer-related processes such as angiogenesis, apoptosis, cell differentiation, cell signaling, hematopoiesis, hormonal control, immune reactions, etc. Exemplary biomarkers include, but are not limited to, CEA for both malignant pleural effusion and peritoneal cancer dissemination; HER-2/neu for stage IV breast cancer; bladder tumor antigen for urothelial cell carcinoma; thyroglobulin for thyroid cancer metastasis; α-fetoprotein for hepatocellular carcinoma; PSA for prostate cancer; CA 125 for non-small cell lung cancer; CA 19.9 for pancreatic cancer; CA 15.3 for breast cancer; the combination of leptin, prolactin, osteopontin, and IGF-II for ovarian cancer; the combination of CD98, fascin, sPIgR, and 14-3-3 eta for lung cancer; troponin I for myocardial infarction, and B-type natriuretic peptide for congestive heart failure. While the previous nine proteins are the only approved markers for cancer testing to date, they are but a small fraction of the total number of available biomarkers, and their sensitivity and specific vary.

Other common biomarkers include the estrogen receptor/progesterone receptor (ER/PR), HER-2/neu, and ESFR for breast cancer, and TIMP-1-associated with serum HER2-positive breast cancer; KRAS and UGT 1A1 for colorectal cancer; HER-2/neu for gastric cancer, c-KIT, CD20 antigen, CD30, and FIP1L1-PDGRF alpha, and PDGFR for GIST; Philadelphia Chromosome (BCR/ABL)/PML/RAR alpha and TPMT/UGT 1A1/ALK EGFR for leukemia/lymphoma; KRAS/EGFR for lung cancer, and BRAF and S100 for melanoma.

Other examples of biomarkers include tumor suppressors that are lost in cancers, such as BRCA1, BRCA2; RNA such as mRNA, microRNA; proteins found in body fluids or tissue such as prostate specific antigen and CA-125; gene and protein based biomarkers; and nonspecific biomarkers such as glycosaminoglycans in body fluids; alkaline phosphatase and urinary hydroxyproline in skeletal involvement; hyaluronic acid excretion and urinary hydroxyproline in bone disease, and combinations thereof.

In malignancies, the biomarkers may be released into the circulation either prior to or after the tumor has grown sufficiently to become metastatic. Small tumors (less than about 2 mm) seldom have any clinical manifestations, however even such small tumors can release chemical and/or biomarkers into the circulation.

The existence of biomarkers in the circulation has been known, but has not met the threshold for locating tumor cells that could not be imaged radiographically or by ultrasound as long as the tumors were asymptomatic. Available imaging methods such as x-ray, magnetic resonance imaging (MRI), functional MRI, computed tomography (CT) scans, CT ultrasound, etc. may not permit visualization of lesions smaller than about 3 mm in diameter. This has been the case for most malignant tumors, or when a malignant tumor is created from a benign precursor lesion such as nevus, breast unspecific cyst or unspecific scar, prostate tumors along with benign prostate hypertrophy, or uterus cancer inside the uterus fibroma, melanoma inside a skin nevus or choroidal nevus under the retina in the eye or in a seborrheic keratosis, etc. Moreover, it is often difficult to follow a cancerous tumor which has been irradiated but may still harbor malignant cells, and that can start growing with time and metastasize before it shows a local growth that is detected by conventional imaging or other methods.

The diagnosis of a malignant tumor may be extremely difficult, even when a tumor is visible clinically or radiologically, e.g. a uterus fibroma that may have some malignant transformation. Moreover, a diagnosis also affects the decision whether or not and also how to remove the tumor. As one example, accessing the uterus through a small incision, and removing the tumor piece by piece using an endoscope and a cutting probe, has a fast post-operative recovery. Such a method is in contrast to completely removing the uterus with the tumor intact out of caution that the tumor may harbor neoplastic cells, but using a large incision with significantly higher operative risks and post-operative complication probabilities. Another, more problematic example, is the decision for a woman having genetic disposition to breast cancer without any physical or radiological manifestation. The woman must endure the stress and fear not knowing if or when she may develop breast cancer, and must consider prophylactic removal of both breasts. As another example, a personal decision whether or not to undergo radiation therapy when a nevus is discovered under the retina, and biopsy results that often do not provide definitive information because of the diversity of the cells in the entire area of the tumor.

When the tumor site is unknown, locating a biomarker in the circulation may be akin to finding a needle in a hay stack. For any particular tumor or cancer, not all biomarkers are even known. Similarly, finding a micro DNA in the circulation may not provide an answer when the tumor is either invisible or has already metastasized. An example of this occurs in patients with uveal melanomas, having a mortality rate of about 50%, even if the tumors undergoes radiation, at the time the ophthalmologist discovers the tumor. This points to the fact that a malignant tumor can metastasize very early, at times even when the size of the tumor is about 2 mm in diameter which is equal to about one million cells. In general, these lesions do not have any symptoms.

The inventive method makes it possible to evaluate a patient with genetic predisposition of a malignant neoplasm before its clinical manifestation can be seen radiographically.

In one embodiment, the presence of one or more biomarkers is evaluated in any body fluid or organ. Exemplary bodily fluids include, but are not limited to, urine, blood, cerebrospinal fluid (CSF), eye cavity fluid, tear film, sputum, fluid obtained from the trachea, bronchi, abdominal cavity, vagina, uterus etc. The biomarkers are analyzed in vitro by methods known in the art, e.g., immunoassays including enzyme-linked immunoassay (ELISA), Western blots, fluorescence in situ hybridization (FISH), polymerase chain reaction (PCR), etc. The biomarkers are then conjugated with functionalized antibody coated nanoparticles and/or quantum dots, as known in the art.

In one embodiment one obtains a liquid biopsy sample. Such a sample may be obtained from, e.g., blood, urine, cerebrospinal fluid (CFS), aqueous or vitreous or abdominal cavity fluid, lymph node fluid, bladder fluid, milk duct fluid, sputum, gastric fluid, bile duct fluid, sinus fluid, etc. The patient may or may not have any clinical symptom. The patient may or may not have history of a family disposition for tumors in and/or cancer of the breast, brain, lung, prostate, ovary, pancreas, etc., or a genetic abnormality leading to progression in diseases such as, e.g., Alzheimer's, Parkinson's, post traumatic brain syndrome, brain tumor, other neurological disease, age related macular degeneration, an infectious disease, an immune response, etc. The method evaluates the components of the sample for cell free nucleic acid-based biomarkers including but not limited to microRNA and microDNA; protein-based biomarkers, extracellular vesicle (EV)-based biomarkers that are contained within exosomes, extracellular vesicles, or microvesicles, and circulating tumor cell (CTC)-based biomarkers. The method uses methodologies such as next generation sequencing (NGS) or recombinant affinity reagents fabricated into nanostructures such as carbon nanotubes, nanowires, quantum dots, or gold nanoshells, to enhance their detection with the use of, e.g., surface-enhanced Raman scattering (SERS), as known in the art.

For example, if a known tumor exists and there is a known biomarker for the tumor, one may have or prepare an antibody against the tumor to be used in both imaging and therapy. Large tumors with symptoms can be imaged, but before the inventive method, there was a problem when a biomarker was present in a liquid biopsy specimen but the tumor was invisible, e.g., an early stage of a tumor, and there was no symptomatic or radiographic evidence of the tumor.

Detecting a tumor biomarker, typically a protein or a glycoprotein, in a liquid biopsy specimen is facilitated by the inventive method. Once detected, an antibody against that tumor biomarker can be prepared. The antitumor biomarker antibody is used to locate the tumor. Antibody production is a well-known method in the art, and it will be appreciated that the antibody against either or both of the tumor biomarker and the tumor cell may be recombinant, monoclonal, polyclonal, or an aptamer. The prepared antitumor cell antibodies are conjugated with nanoparticles and administered to a patient, where they target the tumor cells and can be detected and/or treated. Detection is by photoacoustic/thermoacoustic imaging technology. Treatment is at least by one of thermal energy. The photoacoustic detection and thermal treatment is described herein.

In one embodiment, any specific tumor related biomarker may be used. One example uses trastuzumab or herceptin, a recombinant monoclonal antibody, against the oncogene HER-2, previously mentioned, which is a member of the human epidermal growth factor receptor (HER/EGFR/ERBB) family. Other examples of known monoclonal antibodies or biologics include, but are not limited to, rituximab, cetuximab, racotunomab, obinotuzumab, pertuzumab, belaniatumomab, bevacizumab, nivolumab, ofatumumab, botezomib, daratumumab, ipilumumab, pembrolizumab, and daratumumab.

In one embodiment, in the absence of a specific biomarker, antibodies against biomarkers that are shared by a number of the tumors may be used. Such biomarkers include glycosaminoglycan, which is specific for a group of cancers such as bladder, gastrointestinal, glioblastoma, etc. Antibodies against such biomarkers are then conjugated with nanoparticles, termed functionalized nanoparticles. The term "functionalized" indicates nanoparticles that have been coated to render them soluble, biocompatible, and/or targeted by conjugating them with a biomolecule such as an antibody.

In one embodiment, the pluralities of nanoparticles may be one or more of the following compounds or contain one or more of the following components: quantum dots, nanowires, nanotubes, nanoshells, nanocages, periodic mesoporous organosilica nanoparticles, perovskites, nanoparticles that are magnetic such as iron or iron oxide, paramagnetic, or nanoparticles that are non-magnetic such as gold, gold-silica, gold-iron, silica coated gold nanospheres and nanorods, copper sulfide, ferritic, quartz, graphene, carbon, zinc oxide, piezoelectric, porous silicon nano and microparticles or magnetic luminescent porous silicon nanoparticles and/or microparticles, etc. Any of these nanoparticles, alone or in combination, may be conjugated or otherwise associated with the biomarkers' antibodies, with cell penetrating peptides (CPP), activating CPP (ACPP), biotin, and/or streptavidin using methods known in the art.

In another embodiment, self-assembling bio/nano hybrid material consisting of two constituents at the nanometer or molecular level composed of inorganic and organic compounds, having amphiphilic characteristics, i.e., hydrophilic and lipophilic components or micelles, which may be radioactive (e.g., $Cu^{64}$) or radioactive (e.g., tin) are prepared with biocompatible coatings with cell penetrating peptides (CPP), activating CPP (ACPP), biotin, and/or streptavidin and administered in the body for both therapy and imaging.

In one embodiment, the functionalized nanoparticles or magnetic luminescent porous silicon nanoparticles and/or microparticles travel in the body and attach to receptors of desired cells, e.g., tumors, Alzheimer's plaque, drusen of the retina, etc. These nanoparticles are imaged by applying external thermal energy and/or by applying an electromagnetic radiation, microwaves, radiofrequency waves or a reversible or alternating magnetic field. The thermal energy causes the nanoparticles to expand, producing an ultrasound wave in the tissue known as photoacoustic or thermoacoustic sound. The ultrasound wave can be detected by an ultrasonic receiver which is imaged in two to three dimensional formats as a tomogram. In another embodiment the plaques in Alzheimer's disease, and the drusen in age related macular degeneration, are rendered visible using silica coated nanoparticles <2 nm in diameter administered with turmeric, glycosaminoglycan, amyloid antibody, or percolan, etc. and are quantified. In another embodiment, the nanoparticles are conjugated with porous silicon nanoparticles and/or microparticles or magnetic luminescent porous SI nanoparticles and microparticles and/or thermosensitive polymers, such as chitosan, polylactic poly glycolic acid, acrylic derivatives, polycaprolactone, and are conjugated with are conjugated with antibodies, medications, sterols, antibiotics, antifungals, antibacterials, antiproliferative agents, medications interfering with the normal cell signaling processes, with stimulatory or inhibitory action such as Wnt inhibitors (e.g., ivernectin) or Rho kinase inhibitors known as Rock inhibitors (e.g., Fasudil or Botox) or dyes, etc. that can be released from silica coated gold nanoparticles when coated with thermosensitive polymers, e.g., chitosan coated nanoparticles heated to 40° C.-42° C., to treat various diseases including bacteria, fungi, parasites, plaque, drusen, inflammation, tumors, etc. In another embodiment, the plaques and drusen can be quantified by imaging using light, MRI, photoacoustic/thermoacoustic technology imaging, etc.

In another embodiment, the functionalized anti-biomarker-conjugated nanoparticle, ranges in size from 1 nm to 900 nm. In another embodiment, the functionalized biomarker ranges in size from 1 nm to 8 nm, chosen to enhance their elimination through the kidney for facilitated clearance.

In one embodiment, the nanoparticles are rendered magnetic by coating with a thin film of iron oxide prior to their conjugation with biomarkers' antibodies.

In one embodiment, the nanoparticles are rendered more biocompatible by coating with a compound, including but not limited to the following: (poly)ethylene glycol, cell penetrating peptide (CPP), activating CPP (ACPP), biotin, streptavidin, etc., as known in the art, prior to their injection in the body.

Thermal energy in the form of electromagnetic radiation, ultrasound, or an alternating magnetic field is applied, under the control of a photoacoustic/thermoacoustic imaging system, to the organ suspected of potentially harboring an as yet invisible neoplasm. The thermal energy applied increases preferentially the temperature of the exposed nanoparticle, and creates (e.g. using a laser light) a photoacoustic sound from the superficial lesions and or using focused ultrasound, microwave, RF, or an alternating magnetic field to produce a thermoacoustic sound from deep in the tissue located lesions, and to image or create a tomogram of the accumulated heated nanoparticles/tumor. This image or tomogram represents a suspected neoplasm in that organ, and is compared to an image taken without the thermal application radiographically.

In one embodiment, one administers functionalized antibody-coated nanoparticles that, once attached to tumor cells, become visible with a photoacoustic/thermoacoustic imaging unit that corroborates with an image obtained or not seen with other technology such as ultrasound, MRI, PET, CT scan, etc. In one embodiment, the images obtained with other instruments are either overlapped using a processor or are taken simultaneously during photoacoustic/thermoacoustic imaging. In one embodiment, after administration of the antibody-coated nanoparticle, porous silicon nanoparticles and/or microparticles or magnetic luminescent porous silicon nanoparticles and/or microparticles, periodic mesoporous organosilica nanoparticles an MRI image is overlapped with the photoacoustic image and compared by a processor to verify the changes in the imaged area.

In one embodiment, the nanoparticles are incorporated in liposomes or solid lipid nanoparticles. In this embodiment, they may contain medications or a dye that, upon attainment of a specific tumor temperature, are released. The type of medication is not limited, and can include anti-bacterial, anti-viral, anti-fungal, antineoplastic, anti-inflammatory such as acetyl cycline, anti-beta-amyloid protein, other antibodies, non-steroidal anti-inflammatory drugs, Rock inhibitors, Botox, Wnt inhibitors niclosamide, ivernectin, preventing inflammation or tumor growth, checkpoint inhibitors, anti-VEGF, immune stimulating agents, VLPs, anti-VEGF agents, propranolol, anti-aggregation agents, such as sterols, etc.

In another embodiment, antibody-coated nanoparticles or porous silicon nanoparticles and/or microparticles or magnetic luminescent porous silicon nanoparticles and/or microparticles or antibody coated nanoparticles conjugated with (alpha)-cyclodextrin, (beta)-cyclodextrin, (gamma)-cyclodextrin, hydroxypropyl-b-cyclodextrin (bHPCD) and conjugated with thermosensitive polymers, such as chitosan, carrying any medication including but not limited to sterol, squalamine, lanosterol, is administered to a patient having a neurologic pathology such as Alzheimer's disease, Parkinson's disease, or age related retinal drusen, etc. In this embodiment, administration is either intravenous or local in the cerebrospinal fluid or vitreous cavity, respectively, or at another local site. After controllably increasing the temperature of the functionalized nanoparticle to between 40° C.-43° C. by increased energy delivery through a delivery source, under the control of the photoacoustic imaging system and a processor, the temperature-sensitive coating polymers such as chitosan melts and release medications specific to the pathology. For example, a medication to dissolve amyloid plaques would be administered to a patient with Alzheimer's disease; a medication to remove retinal drusen would be administered to a patient with age related retinal disease, etc.

In one embodiment, the functionalized nanoparticle, e.g., a nanoshell, nanocage, porous silicon nanoparticles and/or microparticles or magnetic luminescent porous silicon nanoparticles and/or microparticles, etc. is combined with biodendrimers that are conjugated with biomarkers and monoclonal antibodies and/or genes, e.g., siRNA, mRNA, RNAi, CRISPR to reduce the expression of checkpoint proteins by the tumor cells etc., and for simultaneous visualization and therapy.

In another embodiment, after thermal imaging one increases the temperature of the functionalized nanoparticles. This is achieved by increased energy delivered by a thermal delivery source under the control of the photoacoustic/thermoacoustic imaging system connected to a processor. The energy delivery unit increases the temperature of the functionalized nanoparticles to 41° C.-43° C. to melt the temperature-sensitive coating polymers such as chitosan, liposomes or solid lipid nanoparticles, and release anticancer medications, Rock inhibitors (e.g., fasudil, exoenzyme or Y27632, Botox etc.), Wnt inhibitors (e.g., niclosamide, etc.) or inhibitory genes, siRNA, miRNA, RNAi, CRISPR to reduce the expression of checkpoint proteins by the tumor cells, etc., or checkpoint inhibitors, or introduce missing genes, or add any other genes for gene editing from the thermosensitive coating of the nanoparticles along with a CRISPR complex to modify the genetic composition of the tumor cells, etc. by using CRISPR-cas9 mediated Homology—Independent Targeted Integration (HITI) or Homology Directed Repair (HDR). In another embodiment, the temperature of the functionalized nanoparticles is increased, by the thermal delivery unit via a processor under the control of the photoacoustic/thermoacoustic imaging unit to image the temperature and control it to 45° C.-47° C., to 47° C., or to 50° C. to kill the suspected tumor to which the antibody-coated nanoparticles are attached and release tumor antigens in the circulation to attract and enhance a cellular immune response to a tumor.

In one embodiment, one synthetizes hybrid, very small (1 nm-8 nm) gold silica nanoparticles that have a dual function, the nanoparticles antibody coated for imaging, and having photovoltaic and magnetic properties, to release one or more gene(s) or medication(s) at certain temperatures, creating a photoacoustic/thermoacoustic signal after heating for imaging in the body or by laser or light stimulation in the eye for simultaneous imaging and therapy.

In one embodiment, using antibody coated quantum dots and light of a specific wavelength that is absorbed by the quantum dot and emits light of a different wavelength, one can render the moving tumor cells and extracellular vesicle visible attached to the quantum dots visible in the retinal or choroidal vessels, or vessels and tumors of the skin, or tumors located beneath the skin and their feeding vessels, by light absorbed by the quantum dots circulating in the vessels, as is done in fluorescence angiography with appropriate filters and camera.

In another embodiment, a gold quantum dot in a mesoporous silica shell or cage is coated with an antibody or a biomarker with cell penetrating peptides (CPP), activating CPP (ACPP), biotin, and/or streptavidin, or antibody coated nanoparticles conjugated with (alpha)-cyclodextrin, (beta)-cyclodextrin, (gamma)-cyclodextrin, hydroxypropyl-b-cyclodextrin (bHPCD) to any cell, e.g., neuronal or tumor cells, retinal drusen, Alzheimer plaques, etc. for delivering medication or gene modification to an organ, e.g., retina or brain by using CRISPR-cas9 mediated Homology—Independent Targeted Integration (HITI) or Homology Directed Repair (HDR).

In another embodiment, the extent of plaque or drusen, as an indicator of disease progression in the brain or eye, respectively, can be evaluated by conjugating nanoparticles with antibodies to glycosaminoglycan, heparin sulfate, glycosaminoglycan, and/or heparin sulfate proteoglycan, and injecting the composition into the circulation of the body or locally to adhere to plaques or drusen for diagnosis, quantitation, and/or therapy with antibodies and medication.

In another embodiment, the pluralities of antibody coated nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) are used for simultaneous imaging and thermotherapy of very small tumors. The nanoparticles are heated to a temperature ranging from 41° C.-43° C., releasing anti-cancer medication, such as Rock inhibitors, such as Botox, exoenzyme or Y27632, or Wnt inhibitors (e.g., niclosamide, ivermectin, Selamectin and alpha lipoidic acid (ALA) precisely at the desired location, along with inhibitory siRNA, RNAi, CRISPR to reduce the expression of checkpoint proteins by the tumor cells, etc., or modify a gene using the CRISPR/cas9 system or another CRISPR system mediated Homology—Independent Targeted Integration (HITI) or Homology Directed Repair (HDR), additionally releasing checkpoint inhibitors such as CTLA-4 or PD-1 or Jagged 1 along with tumoricidal vectors, etc.

In one embodiment, the pluralities of antibody coated nanoparticles with cell penetrating peptides (CPP), activating CPP (ACPP), biotin, and/or streptavidin or antibody-coated nanoparticles conjugated with (alpha)-cyclodextrin, (beta)-cyclodextrin, (gamma)-cyclodextrin, hydroxypropyl-b-cyclodextrin (bHPCD) are rendered radioactive by coating with alpha or beta radiators that are antibody specific or nonspecific biomarkers of the tumor. The nanoparticles can also be coated with heat sensitive polymers, including but not limited to chitosan, PEG, poly amino esters, etc.

In one embodiment, checkpoint inhibitors defined as immune system components that act as co-stimulatory or co-inhibitory molecules are released from the pluralities of antibody coated nanoparticles from thermosensitive coating of the nanoparticles at temperature of 41 to 43 degrees C. along with poisons such as bee or snake venom, ant, sodium formate, or other toxic agents that damage tumor cell membranes, or genes that inhibit tumor growth, siRNA, siDNA, mi RNA, mDNA along with the CRISPR/cas 9 complex using CRISPR-cas9 mediated Homology—Independent Targeted Integration (HITI) or Homology Directed Repair (HDR) or variations of these may be used.

In one embodiment, the pluralities of antibody coated nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD) are coated with a specific or a nonspecific biomarker such as glycosaminoglycan and injected into the circulation, into a body fluid such as the lymphatic system or cerebrospinal fluid (CSF), or inside a body cavity. Examples of injection sites include, but are not limited to, eye, sinuses, abdominal cavity, bladder, uterus, etc. The nanoparticles with cell penetrating peptides (CPP), activating CPP (ACPP), biotin, and/or streptavidin may also be injected into the breast ducts, e.g., through the nipple, inside the brain, into the prostate or other organ, or may even be applied topically. The injected nanoparticles circulate and seek cells bearing a receptor to their antibody, or perhaps cells with specific receptors or biomolecules, and readily attach within minutes or hours.

In one embodiment, specific or non-specific biomarkers' antibodies are conjugated with nanoparticles with cell penetrating peptides (CPP), activating CPP (ACPP), biotin, and/or streptavidin or antibody coated nanoparticles conjugated with (alpha)-cyclodextrin, (beta)-cyclodextrin, (gamma)-cyclodextrin, hydroxypropyl-b-cyclodextrin (bHPCD), and injected either into circulation or locally into a body cavity. The nanoparticles travel and seek cells bearing specific receptors or biomolecules, and attach within a few hours. The patient's body or organ is then scanned, with the thermal energy producing radiation or an alternating or reversible magnetic field, microwave radiation, a laser, radiofrequency (RF) waves or focused ultrasound to heat the nanoparticles. Using photoacoustic/thermoacoustic technology, the sound wave generated by the thermal expansion of the nanoparticle induced by absorption of the thermal energy is recorded. The sound wave signals may originate from any part of the body, or from a specific organ.

In one embodiment, an alternating magnetic field produces heat in magnetic nanoparticles as a result of rapid circular or semicircular motion of the magnetic or paramagnetic nanoparticles heating them. The patient's body is scanned within the reversible magnetic field, and the photoacoustic sound is recorded as a temperature profile of the site of the nanoparticle/cell membrane imaged and location of the lesion is verified.

In another embodiment, other sources of thermal energy are used. Such sources include, but are not limited to, electromagnetic radiation, visible light, invisible light, infrared radiation, microwaves, or radiofrequency waves, focused ultrasound (FUS), etc. The nanoparticles with cell penetrating peptides (CPP), activating CPP (ACPP), biotin, and/or streptavidin are heated from body temperature of 37° C. to 40° C. or 43° C., or if needed to 45° C. At the desired temperature, e.g., 41° C.-43° C., the heat sensitive coating of the nanoparticle melts, releasing its cargo of, e.g., medication, gene, etc., thus facilitating or enhancing passage of these compounds through the membrane of the neoplastic cells and by using CRISPR-cas9 mediated Homology—Independent Targeted Integration (HITI) or Homology Directed Repair (HDR).

In another embodiment, use of a photoacoustic technology unit controls the thermal delivery unit and the thermal energy delivered to the nanoparticles to maintain or reach a predetermined temperature for a desired time.

In one embodiment, the temperatures rise of the nanoparticles expands them, producing a photoacoustic or thermoacoustic sound wave. This sound wave is recorded by one or multiple ultrasonic receivers located on the patient's skin. The signal can be obtained from any part of the body, or from a specific organ, since the signal travels through the body as a wave. The signal or sound pulse is converted to an electric pulse in the receiver, then using a processor, is amplified and imaged on a monitor. A processor produces a two- or three-dimension image of the lesion, localizing the location of the sound and indicating the size of a lesion and its temperature by the amplitude of the sound pulse.

In one embodiment, photoacoustic imaging is used for a very early stage diagnosis of cancerous lesion that are less than 2 mm in diameter, which are radiographically invisible without knowing their exact location in the body.

In one embodiment using photoacoustic technology and a specific or non-specific tumor biomarker, a very small lesion (<2 mm in diameter) is imaged in the body when the tumor has not caused any clinical symptom. The inventive method thus is used to differentiate a malignant lesion from a benign lesion, even if the cancerous lesion is inside a begin lesion. It is noteworthy that biopsy of these very small tumors, even when the lesion is visible, e.g., on skin or under the retina, may not yield malignant cells if the biopsy is performed on a part of the lesion that contains benign cells. With tumors in the brain, it is most often the case that the tumors will not be noted absent a neurological symptom.

In one embodiment, the inventive method is used with specific biomarkers of a tumor such as breast cancer, prostate cancer, glioma, pancreatic malignancies, along with nonspecific biomarkers. The location and size of a malignant tumor in any organ is imaged in a patient with a genetic propensity to develop a tumor. The thermal energy may also be applied, if desired, to treat the lesion simultaneously with providing the photoacoustic effect. Subsequent evaluation of the level of these biomarkers in the blood indicate if the lesion was damaged or eliminated by the thermal energy increasing the biomarkers in the blood, including use of medicaments/dye released from the thermosensitive nanoparticle coating with cell penetrating peptides (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD) and/or other treatment agents delivered by the method as cargo in the nanoparticles.

In one embodiment, a combination of biomarkers can be used in an early stage. For example, specific or nonspecific bio-markers such as glycosaminoglycans can be used in imaging a malignant lesion using antibody-coated nanoparticles to photoacoustically image the presence of a very small early stage tumor anywhere in the body.

In another embodiment, the inventive method is employed to determine residual tumor cells that may have left at the site of a tumor resection or elsewhere in the body, and to treat or eliminate the residual tumor cells.

In another embodiment, the functionalized nanoparticles are conjugated with one of the recombinant, monoclonal, or polyclonal antibodies or aptamers known in the art and administered along with either one or more toxin(s) or antibodies, along with a medication that is provided at a much lower dose systemically to kill the already compromised tumor cells. Monoclonal antibodies that may be used include, but are not limited to, those shown in Table 1, e.g., rituximab, obinuzumab, oftumumab, etc.

TABLE 1

| Name | Trade name | Type | Source | Target | Use |
|---|---|---|---|---|---|
| 3F8 | | mab | mouse | GD2 | neuroblastoma |
| 8H9 | | mab | mouse | B7-H3 | neuroblastoma, sarcoma, metastatic brain cancers |
| Abagovomab | | mab | mouse | CA-125 (imitation) | ovarian cancer |
| Abciximab | ReoPro | Fab | chimeric | CD41 (integrin alpha-IIb) | platelet aggregation inhibitor |
| Abituzumab | | mab | humanized | CD51 | cancer |
| Abrilumab | | mab | human | integrin α4β7 | inflammatory bowel disease, ulcerative colitis, Crohn's disease |
| Actoxumab | | mab | human | *Clostridium difficile* | *Clostridium difficile* infection |
| Adalimumab | Humira | mab | human | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | | mab | human | EpCAM | prostate and breast cancer |
| Aducanumab | | mab | human | beta-amyloid | Alzheimer's disease |
| Afelimomab | | F(ab')₂ | mouse | TNF-α | sepsis |
| Afutuzumab | | mab | humanized | CD20 | lymphoma |
| Alacizumab pegol | | F(ab')₂ | humanized | VEGFR2 | cancer |
| ALD518 | | ? | humanized | IL-6 | rheumatoid arthritis |
| Alemtuzumab | Campath, MabCampath | mab | humanized | CD52 | Multiple sclerosis |
| Alirocumab | | mab | human | NARP-1 | hypercholesterolemia |
| Altumomab pentetate | Hybri-ceaker | mab | mouse | CEA | colorectal cancer (diagnosis) |
| Amatuximab | | mab | chimeric | mesothelin | cancer |
| Anatumomab mafenatox | | Fab | mouse | TAG-72 | non-small cell lung carcinoma |
| Anetumab ravtansine | | mab | human | MSLN | cancer |
| Anifrolumab | | mab | human | interferon α/β receptor | systemic lupus erythematosus |
| Anrukinzumab (= IMA-638) | | mab | humanized | IL-13 | ? |
| Apolizumab | | mab | humanized | HLA-DR ? | hematological cancers |
| Arcitumomab | CEA-Scan | Fab' | mouse | CEA | gastrointestinal cancers (diagnosis) |
| Ascrinvacumab | | mab | human | activin receptor-like kinase 1 | cancer |
| Aselizumab | | mab | humanized | L-selectin (CD62L) | severely injured patients |
| Atezolizumab | | mab | humanized | CD274 | cancer |
| Atinumab | | mab | human | RTN4 | ? |
| Atlizumab (= tocilizumab) | Actemra, RoActemra | mab | humanized | IL-6 receptor | rheumatoid arthritis |
| Atorolimumab | | mab | human | Rhesus factor | hemolytic disease of the newborn[citation needed] |

TABLE 1-continued

| Name | Trade name | Type | Source | Target | Use |
|---|---|---|---|---|---|
| Bapineuzumab | | mab | humanized | beta amyloid | Alzheimer's disease |
| Basiliximab | Simulect | mab | chimeric | CD25 (α chain of IL-2 receptor) | prevention of organ transplant rejections |
| Bavituximab | | mab | chimeric | phosphatidylserine | cancer, viral infections |
| Bectumomab | LymphoScan | Fab' | mouse | CD22 | non-Hodgkin's lymphoma (detection) |
| Begelomab | | mab | mouse | DPP4 | ? |
| Belimumab | Benlysta, LymphoStat-B | mab | human | BAFF | non-Hodgkin lymphoma etc. |
| Benralizumab | | mab | humanized | CD125 | asthma |
| Bertilimumab | | mab | human | CCL11 (eotaxin-1) | severe allergic disorders |
| Besilesomab | Scintimun | mab | mouse | CEA-related antigen | inflammatory lesions and metastases (detection) |
| Bevacizumab | Avastin | mab | humanized | VEGF-A | metastatic cancer, retinopathy of prematurity |
| Bezlotoxumab | | mab | human | *Clostridium difficile* | *Clostridium difficile* infection |
| Biciromab | FibriScint | Fab' | mouse | fibrin II, beta chain | thromboembolism (diagnosis) |
| Bimagrumab | | mab | human | ACVR2B | myostatin inhibitor |
| Bimekizumab | | mab | humanized | IL17A and IL17F | ? |
| Bivatuzumab mertansine | | mab | humanized | CD44 v6 | squamous cell carcinoma |
| Blinatumomab | | BiTE | mouse | CD19 | cancer |
| Blosozumab | | mab | humanized | SOST | osteoporosis |
| Bococizumab | | mab | humanized | neural apoptosis-regulated proteinase 1 | dyslipidemia |
| Brentuximab vedotin | | mab | chimeric | CD30 (TNFRSF8) | hematologic cancers |
| Briakinumab | | mab | human | IL-12, IL-23 | psoriasis, rheumatoid arthritis, inflammatory bowel diseases, multiple sclerosis |
| Brodalumab | | mab | human | IL-17 | inflammatory diseases |
| Brolucizumab | | mab | humanized | VEGFA | ? |
| Brontictuzumab | | mab | | Notch 1 | cancer |
| Canakinumab | Ilaris | mab | human | IL-1? | rheumatoid arthritis |
| Cantuzumab mertansine | | mab | humanized | mucin CanAg | colorectal cancer etc. |
| Cantuzumab ravtansine | | mab | humanized | MUC1 | cancers |
| Caplacizumab | | mab | humanized | VWF | thrombotic thrombocytopenic purpura, thrombosis |
| Capromab pendetide | Prostascint | mab | mouse | prostatic carcinoma cells | prostate cancer (detection) |
| Carlumab | | mab | human | MCP-1 | oncology/immune indications |
| Catumaxomab | Removab | 3funct | rat/mouse hybrid | EpCAM, CD3 | ovarian cancer, malignant ascites, gastric cancer |
| cBR96-doxorubicin immunoconjugate | | mab | humanized | Lewis-Y antigen | cancer |
| Cedelizumab | | mab | humanized | CD4 | prevention of organ transplant rejections, treatment of autoimmune diseases |
| Certolizumab pegol | Cimzia | Fab' | humanized | TNF-α | Crohn's disease |
| Cetuximab | Erbitux | mab | chimeric | EGFR | metastatic colorectal cancer and head and neck cancer |
| Ch.14.18 | | mab | chimeric | ??? | neuroblastoma |
| Citatuzumab bogatox | | Fab | humanized | EpCAM | ovarian cancer and other solid tumors |
| Cixutumumab | | mab | human | IGF-1 receptor | solid tumors |
| Clazakizumab | | mab | humanized | *Oryctolagus cuniculus* | rheumatoid arthritis |
| Clenoliximab | | mab | chimeric | CD4 | rheumatoid arthritis |
| Clivatuzumab tetraxetan | hPAM4-Cide | mab | humanized | MUC1 | pancreatic cancer |
| Codrituzumab | | mab | humanized | glypican 3 | cancer |
| Coltuximab ravtansine | | mab | chimeric | CD19 | cancer |
| Conatumumab | | mab | human | TRAIL-R2 | cancer |
| Concizumab | | mab | humanized | TFPI | bleeding |
| Crenezumab | | mab | humanized | 1-40-β-amyloid | Alzheimer's disease |
| CR6261 | | mab | human | Influenza A hemagglutinin | infectious disease/influenza A |
| Dacetuzumab | | mab | humanized | CD40 | hematologic cancers |
| Daclizumab | Zenapax | mab | humanized | CD25 (α chain of IL-2 receptor) | prevention of organ transplant rejections |
| Dalotuzumab[39] | | mab | humanized | insulin-like growth factor I receptor | cancer etc. |
| Dapirolizumab pegol | | mab | humanized | CD40 ligand | ? |

TABLE 1-continued

| Name | Trade name | Type | Source | Target | Use |
|---|---|---|---|---|---|
| Daratumumab | | mab | human | CD38 (cyclic ADP ribose hydrolase) | cancer |
| Dectrekumab | | mab | human | IL-13 | ? |
| Demcizumab | | mab | humanized | DLL4 | cancer |
| Denintuzumab mafodotin | | mab | humanized | CD19 | cancer |
| Denosumab | Prolia | mab | human | RANKL | osteoporosis, bone metastases etc. |
| Derlotuximab biotin | | mab | chimeric | histone complex | recurrent glioblastoma multiforme |
| Detumomab | | mab | mouse | B-lymphoma cell | lymphoma |
| Dinutuximab | | mab | chimeric | ganglioside GD2 | neuroblastoma |
| Diridavumab | | mab | human | hemagglutinin | influenza A |
| Dorlimomab aritox | | F(ab')$_2$ | mouse | ? | ? |
| Drozitumab | | mab | human | DR5 | cancer etc. |
| Duligotumab | | mab | human | HER3 | ? |
| Dupilumab | | mab | human | IL4 | atopic diseases |
| Durvalumab | | mab | human | CD274 | cancer |
| Dusigitumab | | mab | human | ILGF2 | cancer |
| Ecromeximab | | mab | chimeric | GD3 ganglioside | malignant melanoma |
| Eculizumab | Soliris | mab | humanized | C5 | paroxysmal nocturnal hemoglobinuria |
| Edobacomab | | mab | mouse | endotoxin | sepsis caused by Gram-negative bacteria |
| Edrecolomab | Panorex | mab | mouse | EpCAM | colorectal carcinoma |
| Efalizumab | Raptiva | mab | humanized | LFA-1 (CD11a) | psoriasis (blocks T-cell migration) |
| Efungumab | Mycograb | scFv | human | Hsp90 | invasive *Candida* infection |
| Eldelumab | | mab | human | interferon gamma-induced protein | Crohn's disease, ulcerative colitis |
| Elgemtumab | | mab | human | ERBB3 | cancer |
| Elotuzumab | | mab | humanized | SLAMF7 | multiple myeloma |
| Elsilimomab | | mab | mouse | IL-6 | ? |
| Emactuzumab | | mab | humanized | CSF1R | cancer |
| Emibetuzumab | | mab | humanized | HHGFR | cancer |
| Enavatuzumab | | mab | humanized | TWEAK receptor | cancer etc. |
| Enfortumab vedotin | | mab | human | AGS-22M6 | cancer expressing Nectin-4 |
| Enlimomab pegol | | mab | mouse | ICAM-1 (CD54) | ? |
| Enoblituzumab | | mab | humanized | B7-H3 | cancer |
| Enokizumab | | mab | humanized | IL9 | asthma |
| Enoticumab | | mab | human | DLL4 | ? |
| Ensituximab | | mab | chimeric | 5AC | cancer |
| Epitumomab cituxetan | | mab | mouse | episialin | ? |
| Epratuzumab | | mab | humanized | CD22 | cancer, SLE |
| Erlizumab | | F(ab')$_2$ | humanized | ITGB2 (CD18) | heart attack, stroke, traumatic shock |
| Ertumaxomab | Rexomun | 3funct | rat/mouse hybrid | HER2/neu, CD3 | breast cancer etc. |
| Etaracizumab | Abegrin | mab | humanized | integrin αvβ3 | melanoma, prostate cancer, ovarian cancer etc. |
| Etrolizumab | | mab | humanized | integrin α7 β7 | inflammatory bowel disease |
| Evinacumab | | mab | human | angiopoietin 3 | dyslipidemia |
| Evolocumab | | mab | human | PCSK9 | hypercholesterolemia |
| Exbivirumab | | mab | human | hepatitis B surface antigen | hepatitis B |
| Fanolesomab | NeutroSpec | mab | mouse | CD15 | appendicitis (diagnosis) |
| Faralimomab | | mab | mouse | interferon receptor | ? |
| Farletuzumab | | mab | humanized | folate receptor 1 | ovarian cancer |
| Fasinumab | | mab | human | HNGF | acute sciatic pain |
| FBTA05 | Lymphomun | 3funct | rat/mouse hybrid | CD20 | chronic lymphocytic leukaemia |
| Felvizumab | | mab | humanized | respiratory syncytial virus | respiratory syncytial virus infection |
| Fezakinumab | | mab | human | IL-22 | rheumatoid arthritis, psoriasis |
| Ficlatuzumab | | mab | humanized | HGF | cancer etc. |
| Figitumumab | | mab | human | IGF-1 receptor | adrenocortical carcinoma, non-small cell lung carcinoma etc. |
| Firivumab | | mab | human | influenza A virus hemagglutinin | ? |
| Flanvotumab | | mab | human | TYRP1(glycoprotein 75) | melanoma |
| Fletikumab | | mab | human | IL 20 | rheumatoid arthritis |
| Fontolizumab | HuZAF | mab | humanized | IFN-γ | Crohn's disease etc. |
| Foralumab | | mab | human | CD3 epsilon | ? |

TABLE 1-continued

| Name | Trade name | Type | Source | Target | Use |
|---|---|---|---|---|---|
| Foravirumab | | mab | human | rabies virus glycoprotein | rabies (prophylaxis) |
| Fresolimumab | | mab | human | TGF-β | idiopathic pulmonary fibrosis, focal segmental glomerulosclerosis, cancer |
| Fulranumab | | mab | human | NGF | pain |
| Futuximab | | mab | chimeric | EGFR | ? |
| Galiximab | | mab | chimeric | CD80 | B-cell lymphoma |
| Ganitumab | | mab | human | IGF-I | cancer |
| Gantenerumab | | mab | human | beta amyloid | Alzheimer's disease |
| Gavilimomab | | mab | mouse | CD147 (basigin) | graft versus host disease |
| Gemtuzumab ozogamicin | Mylotarg | mab | humanized | CD33 | acute myelogenous leukemia |
| Gevokizumab | | mab | humanized | IL-1β | diabetes etc. |
| Girentuximab | Rencarex | mab | chimeric | carbonic anhydrase 9 (CA-IX) | clear cell renal cell carcinoma[81] |
| Glembatumumab vedotin | | mab | human | GPNMB | melanoma, breast cancer |
| Golimumab | Simponi | mab | human | TNF-α | rheumatoid arthritis, psoriatic arthritis, ankylosing spondylitis |
| Gomiliximab | | mab | chimeric | CD23 (IgE receptor) | allergic asthma |
| Guselkumab | | mab | human | IL23 | psoriasis |
| Ibalizumab | | mab | humanized | CD4 | HIV infection |
| Ibritumomab tiuxetan | Zevalin | mab | mouse | CD20 | non-Hodgkin's lymphoma |
| Icrucumab | | mab | human | VEGFR-1 | cancer etc. |
| Idarucizumab | | mab | humanized | dabigatran | reversal of anticoagulant effects of dabigatran |
| Igovomab | Indimacis-125 | F(ab')$_2$ | mouse | CA-125 | ovarian cancer (diagnosis) |
| IMAB362 | | mab | human | CLDN18.2 | gastrointestinal adenocarcinomas and pancreatic tumor |
| Imalumab | | mab | human | MIF | cancer |
| Imciromab | Myoscint | mab | mouse | cardiac myosin | cardiac imaging |
| Imgatuzumab | | mab | humanized | EGFR | cancer |
| Inclacumab | | mab | human | selectin P | ? |
| Indatuximab ravtansine | | mab | chimeric | SDC1 | cancer |
| Indusatumab vedotin | | mab | human | GUCY2C | cancer |
| Infliximab | Remicade | mab | chimeric | TNF-α | rheumatoid arthritis, ankylosing spondylitis, psoriatic arthritis, psoriasis, Crohn's disease, ulcerative colitis |
| Intetumumab | | mab | human | CD51 | solid tumors (prostate cancer, melanoma) |
| Inolimomab | | mab | mouse | CD25 (α chain of IL-2 receptor) | graft versus host disease |
| Inotuzumab ozogamicin | | mab | humanized | CD22 | cancer |
| Ipilimumab | Yervoy | mab | human | CD152 | melanoma |
| Iratumumab | | mab | human | CD30 (TNFRSF8) | Hodgkin's lymphoma |
| Isatuximab | | mab | chimeric | CD38 | cancer |
| Itolizumab | | mab | humanized | CD6 | ? |
| Ixekizumab | | mab | humanized | IL-17A | autoimmune diseases |
| Keliximab | | mab | chimeric | CD4 | chronic asthma |
| Labetuzumab | CEA-Cide | mab | humanized | CEA | colorectal cancer |
| Lambrolizumab | | mab | humanized | PDCD1 | antineoplastic agent |
| Lampalizumab | | mab | humanized | CFD | ? |
| Lebrikizumab | | mab | humanized | IL-13 | asthma |
| Lemalesomab | | mab | mouse | NCA-90 (granulocyte antigen) | diagnostic agent |
| Lenzilumab | | mab | human | CSF2 | ? |
| Lerdelimumab | | mab | human | TGF beta 2 | reduction of scarring after glaucoma surgery |
| Lexatumumab | | mab | human | TRAIL-R2 | cancer |
| Libivirumab | | mab | human | hepatitis B surface antigen | hepatitis B |
| Lifastuzumab vedotin | | mab | humanized | phosphate-sodium co-transporter | cancer |
| Ligelizumab | | mab | humanized | IGHE | severe asthma and chronic spontaneous urticarial |
| Lilotomab satetraxetan | | mab | mouse | CD37 | cancer |
| Lintuzumab | | mab | humanized | CD33 | cancer |
| Lirilumab | | mab | human | KIR2D | ? |
| Lodelcizumab | | mab | humanized | PCSK9 | hypercholesterolemia |

TABLE 1-continued

| Name | Trade name | Type | Source | Target | Use |
|---|---|---|---|---|---|
| Lokivetmab | | mab | veterinary | *Canis lupus familiaris* IL31 | ? |
| Lorvotuzumab mertansine | | mab | humanized | CD56 | cancer |
| Lucatumumab | | mab | human | CD40 | multiple myeloma, non-Hodgkin's lymphoma, Hodgkin's lymphoma |
| Lulizumab pegol | | mab | humanized | CD28 | autoimmune diseases |
| Lumiliximab | | mab | chimeric | CD23 (IgE receptor) | chronic lymphocytic leukemia |
| Lumretuzumab | | mab | humanized | ERBB3 | cancer |
| Mapatumumab | | mab | human | TRAIL-R1 | cancer |
| Margetuximab | | mab | humanized | ch4D5 | cancer |
| Maslimomab | | ? | mouse | T-cell receptor | ? |
| Mavrilimumab | | mab | human | GMCSF receptor α-chain | rheumatoid arthritis |
| Matuzumab | | mab | humanized | EGFR | colorectal, lung and stomach cancer |
| Mepolizumab | Bosatria | mab | humanized | IL-5 | asthma and white blood cell diseases |
| Metelimumab | | mab | human | TGF beta 1 | systemic scleroderma |
| Milatuzumab | | mab | humanized | CD74 | multiple myeloma and other hematological malignancies |
| Minretumomab | | mab | mouse | TAG-72 | tumor detection (and therapy?) |
| Mirvetuximab soravtansine | | mab | chimeric | folate receptor alpha | cancer |
| Mitumomab | | mab | mouse | GD3 ganglioside | small cell lung carcinoma |
| Mogamulizumab | | mab | humanized | CCR4 | cancer |
| Morolimumab | | mab | human | Rhesus factor | ? |
| Motavizumab | Numax | mab | humanized | respiratory syncytial virus | respiratory syncytial virus (prevention) |
| Moxetumomab pasudotox | | mab | mouse | CD22 | cancer |
| Muromonab-CD3 | Orthoclone OKT3 | mab | mouse | CD3 | prevention of organ transplant rejections |
| Nacolomab tafenatox | | Fab | mouse | C242 antigen | colorectal cancer |
| Namilumab | | mab | human | CSF2 | ? |
| Naptumomab estafenatox | | Fab | mouse | 5T4 | non-small cell lung carcinoma, renal cell carcinoma |
| Narnatumab | | mab | human | RON | cancer |
| Natalizumab | Tysabri | mab | humanized | integrin α4 | multiple sclerosis, Crohn's disease |
| Nebacumab | | mab | human | endotoxin | sepsis |
| Necitumumab | | mab | human | EGFR | non-small cell lung carcinoma |
| Nemolizumab | | mab | humanized | IL31RA | ? |
| Nerelimomab | | mab | mouse | TNF-α | ? |
| Nesvacumab | | mab | human | angiopoietin 2 | cancer |
| Nimotuzumab | Theracim, Theraloc | mab | humanized | EGFR | squamous cell carcinoma, head and neck cancer, nasopharyngeal cancer, glioma |
| Nivolumab | | mab | human | PD-1 | cancer |
| Nofetumomab merpentan | Verluma | Fab | mouse | ? | cancer (diagnosis) |
| Obiltoxaximab | | mab | chimeric | *Bacillus anthracis* anthrax | *Bacillus anthracis* spores |
| Obinutuzumab | Gazyva | mab | humanized | CD20 | Chronic lymphatic leukemia |
| Ocaratuzumab | | mab | humanized | CD20 | cancer |
| Ocrelizumab | | mab | humanized | CD20 | rheumatoid arthritis, lupus erythematosus etc. |
| Odulimomab | | mab | mouse | LFA-1 (CD11a) | prevention of organ transplant rejections, immunological diseases |
| Ofatumumab | Arzerra | mab | human | CD20 | chronic lymphocytic leukemia etc. |
| Olaratumab | | mab | human | PDGF-Rα | cancer |
| Olokizumab | | mab | humanized | IL6 | ? |
| Omalizumab | Xolair | mab | humanized | IgE Fc region | allergic asthma |
| Onartuzumab | | mab | humanized | human scatter factor receptor kinase | cancer |
| Ontuxizumab | | mab | chimeric/humanized | TEM1 | cancer |
| Opicinumab[1] | | mab | human | LINGO-1 | multiple sclerosis |
| Oportuzumab monatox | | scFv | humanized | EpCAM | cancer |

TABLE 1-continued

| Name | Trade name | Type | Source | Target | Use |
|---|---|---|---|---|---|
| Oregovomab | OvaRex | mab | mouse | CA-125 | ovarian cancer |
| Orticumab | | mab | human | oxLDL | ? |
| Otelixizumab | | mab | chimeric/humanized | CD3 | diabetes mellitus type 1 |
| Otlertuzumab | | mab | humanized | CD37 | cancer |
| Oxelumab | | mab | human | OX-40 | asthma |
| Ozanezumab | | mab | humanized | NOGO-A | ALS and multiple sclerosis |
| Ozoralizumab | | mab | humanized | TNF-α | inflammation |
| Pagibaximab | | mab | chimeric | lipoteichoic acid | sepsis (*Staphylococcus*) |
| Palivizumab | Synagis, Abbosynagis | mab | humanized | F protein of respiratory syncytial virus | respiratory syncytial virus (prevention) |
| Panitumumab | Vectibix | mab | human | EGFR | colorectal cancer |
| Pankomab | | mab | humanized | tumor specific glycosylation of MUC1 | ovarian cancer |
| Panobacumab | | mab | human | *Pseudomonas aeruginosa* | *Pseudomonas aeruginosa* infection |
| Parsatuzumab | | mab | human | EGFL7 | cancer |
| Pascolizumab | | mab | humanized | IL-4 | asthma |
| Pasotuxizumab | | mab | chimeric/humanized | folate hydrolase | cancer |
| Pateclizumab | | mab | humanized | LTA | TNF |
| Patritumab | | mab | human | HER3 | cancer |
| Pembrolizumab | | mab | humanized | PDCD1 | cancer etc. |
| Pemtumomab | Theragyn | ? | mouse | MUC1 | cancer |
| Perakizumab | | mab | humanized | IL17A | arthritis |
| Pertuzumab | Omnitarg | mab | humanized | HER2/neu | cancer |
| Pexelizumab | | scFv | humanized | C5 | reduction of side effects of cardiac surgery |
| Pidilizumab | | mab | humanized | PD-1 | cancer and infectious diseases |
| Pinatuzumab vedotin | | mab | humanized | CD22 | cancer |
| Pintumomab | | mab | mouse | adenocarcinoma antigen | adenocarcinoma (imaging) |
| Placulumab | | mab | human | human TNF | ? |
| Polatuzumab vedotin | | mab | humanized | CD79B | cancer |
| Ponezumab | | mab | humanized | human beta-amyloid | Alzheimer's disease |
| Priliximab | | mab | chimeric | CD4 | Crohn's disease, multiple sclerosis |
| Pritoxaximab | | mab | chimeric | *E. coli* shiga toxin type-1 | ? |
| Pritumumab | | mab | human | vimentin | brain cancer |
| PRO 140 | | ? | humanized | CCR5 | HIV infection |
| Quilizumab | | mab | humanized | IGHE | asthma |
| Racotumomab | | mab | mouse | N-glycolylneuraminic acid | cancer |
| Radretumab | | mab | human | fibronectin extra domain-B | cancer |
| Rafivirumab | | mab | human | rabies virus glycoprotein | rabies (prophylaxis) |
| Ralpancizumab | | mab | humanized | neural apoptosis-regulated proteinase 1 | dyslipidemia |
| Ramucirumab | Cyramza | mab | human | VEGFR2 | solid tumors |
| Ranibizumab | Lucentis | Fab | humanized | VEGF-A | macular degeneration (wet form) |
| Raxibacumab | | mab | human | anthrax toxin, protective antigen | anthrax (prophylaxis and treatment) |
| Refanezumab | | mab | humanized | myelin-associated glycoprotein | recovery of motor function after stroke |
| Regavirumab | | mab | human | cytomegalovirus glycoprotein B | cytomegalovirus infection |
| Reslizumab | | mab | humanized | IL-5 | inflammations of the airways, skin and gastrointestinal tract |
| Rilotumumab | | mab | human | HGF | solid tumors |
| Rinucumab | | mab | human | platelet-derived growth factor receptor beta | neovascular age-related macular degeneration |
| Rituximab | MabThera, Rituxan | mab | chimeric | CD20 | lymphomas, leukemias, some autoimmune disorders |
| Robatumumab | | mab | human | IGF-1 receptor | cancer |
| Roledumab | | mab | human | RHD | ? |
| Romosozumab | | mab | humanized | sclerostin | osteoporosis |
| Rontalizumab | | mab | humanized | IFN-α | systemic lupus erythematosus |
| Rovelizumab | LeukArrest | mab | humanized | CD11, CD18 | haemorrhagic shock etc. |
| Ruplizumab | Antova | mab | humanized | CD154 (CD40L) | rheumatic diseases |

TABLE 1-continued

| Name | Trade name | Type | Source | Target | Use |
|---|---|---|---|---|---|
| Sacituzumab govitecan | | mab | humanized | tumor-associated calcium signal transducer 2 | cancer |
| Samalizumab | | mab | humanized | CD200 | cancer |
| Sarilumab | | mab | human | IL6 | rheumatoid arthritis, ankylosing spondylitis |
| Satumomab pendetide | | mab | mouse | TAG-72 | cancer (diagnosis) |
| Secukinumab | | mab | human | IL-17A | uveitis, rheumatoid arthritis psoriasis |
| Seribantumab | | mab | human | ERBB3 | cancer |
| Setoxaximab | | mab | chimeric | *E. coli* shiga toxin type-2 | ? |
| Sevirumab | | ? | human | cytomegalovirus | cytomegalovirus infection |
| Sibrotuzumab | | mab | humanized | FAP | cancer |
| SGN-CD19A | | mab | humanized | CD19 | acute lymphoblastic leukemia and B-cell non-Hodgkin lymphoma |
| SGN-CD33A | | mab | humanized | CD33 | Acute myeloid leukemia |
| Sifalimumab | | mab | humanized | IFN-α | SLE, dermatomyositis, polymyositis |
| Siltuximab | | mab | chimeric | IL-6 | cancer |
| Simtuzumab | | mab | humanized | LOXL2 | fibrosis |
| Siplizumab | | mab | humanized | CD2 | psoriasis, graft-versus-host disease (prevention) |
| Sirukumab | | mab | human | IL-6 | rheumatoid arthritis |
| Sofituzumab vedotin | | mab | humanized | CA 125 | ovarian cancer |
| Solanezumab | | mab | humanized | beta amyloid | Alzheimer's disease |
| Solitomab | | mab | mouse | EpCAM | ? |
| Sonepcizumab | | ? | humanized | sphingosine-1-phosphate | choroidal and retinal neovascularization |
| Sontuzumab | | mab | humanized | episialin | ? |
| Stamulumab | | mab | human | myostatin | muscular dystrophy |
| Sulesomab | LeukoScan | Fab' | mouse | NCA-90 (granulocyte antigen) | osteomyelitis (imaging) |
| Suvizumab | | mab | humanized | HIV-1 | viral infections |
| Tabalumab | | mab | human | BAFF | B-cell cancers |
| Tacatuzumab tetraxetan | AFP-Cide | mab | humanized | alpha-fetoprotein | cancer |
| Tadocizumab | | Fab | humanized | integrin αIIbβ3 | percutaneous coronary intervention |
| Talizumab | | mab | humanized | IgE | allergic reaction |
| Tanezumab | | mab | humanized | NGF | pain |
| Taplitumomab paptox | | mab | mouse | CD19 | cancer[citation needed] |
| Tarextumab | | mab | human | Notch receptor | cancer |
| Tefibazumab | Aurexis | mab | humanized | clumping factor A | *Staphylococcus aureus* infection |
| Telimomab aritox | | Fab | mouse | ? | ? |
| Tenatumomab | | mab | mouse | tenascin C | cancer |
| Teneliximab | | mab | chimeric | CD40 | ? |
| Teplizumab | | mab | humanized | CD3 | diabetes mellitus type 1 |
| Teprotumumab | | mab | human | CD221 | hematologic tumors |
| Tesidolumab | | mab | human | C5 | ? |
| TGN1412 | | ? | humanized | CD28 | chronic lymphocytic leukemia, rheumatoid arthritis |
| Ticilimumab (= tremelimumab) | | mab | human | CTLA-4 | cancer |
| Tildrakizumab | | mab | humanized | IL23 | immunologically mediated inflammatory disorders |
| Tigatuzumab | | mab | humanized | TRAIL-R2 | cancer |
| TNX-650 | | ? | humanized | IL-13 | Hodgkin's lymphoma |
| Tocilizumab[6] (= atlizumab) | Actemra, RoActemra | mab | humanized | IL-6 receptor | rheumatoid arthritis |
| Toralizumab | | mab | humanized | CD154 (CD40L) | rheumatoid arthritis, lupus nephritis etc. |
| Tosatoxumab | | mab | human | *Staphylococcus aureus* | ? |
| Tositumomab | Bexxar | ? | mouse | CD20 | follicular lymphoma |
| Tovetumab | | mab | human | CD140a | cancer |
| Tralokinumab | | mab | human | IL-13 | asthma etc. |
| Trastuzumab | Herceptin | mab | humanized | HER2/neu | breast cancer |
| TRBS07 | Ektomab | 3funct | ? | GD2 | melanoma |
| Tregalizumab | | mab | humanized | CD4 | ? |
| Tremelimumab | | mab | human | CTLA-4 | cancer |
| Trevogrumab | | mab | human | growth differentiation factor 8 | muscle atrophy due to orthopedic disuse and sarcopenia |

TABLE 1-continued

| Name | Trade name | Type | Source | Target | Use |
|---|---|---|---|---|---|
| Tucotuzumab celmoleukin | | mab | humanized | EpCAM | cancer |
| Tuvirumab | | ? | human | hepatitis B virus | chronic hepatitis B |
| Ublituximab | | mab | chimeric | MS4A1 | cancer |
| Ulocuplumab | | mab | human | C—X—C chemokine receptor type 4 | hematologic malignancies |
| Urelumab | | mab | human | 4-1BB | cancer etc. |
| Urtoxazumab | | mab | humanized | *Escherichia coli* | diarrhoea caused by *E. coli* |
| Ustekinumab | Stelara | mab | human | IL-12, IL-23 | multiple sclerosis, psoriasis, psoriatic arthritis |
| Vandortuzumab vedotin | | mab | humanized | STEAP1 | cancer |
| Vantictumab | | mab | human | Frizzled receptor | cancer |
| Vanucizumab | | mab | humanized | angiopoietin 2 | cancer |
| Vapaliximab | | mab | chimeric | AOC3 (VAP-1) | ? |
| Varlilumab | | mab | human | CD27 | ? |
| Vatelizumab | | mab | humanized | ITGA2 | ? |
| Vedolizumab | | mab | humanized | integrin α4β7 | Crohn's disease, ulcerative colitis |
| Veltuzumab | | mab | humanized | CD20 | non-Hodgkin's lymphoma |
| Vepalimomab | | mab | mouse | AOC3 (VAP-1) | inflammation |
| Vesencumab | | mab | human | NRP1 | ? |
| Visilizumab | Nuvion | mab | humanized | CD3 | Crohn's disease, ulcerative colitis |
| Volociximab | | mab | chimeric | integrin α5β1 | solid tumors |
| Vorsetuzumab mafodotin | | mab | humanized | CD70 | cancer |
| Votumumab | HumaSPECT | mab | human | tumor antigen CTAA16.88 | colorectal tumors |
| Zalutumumab | HuMax-EGFr | mab | human | EGFR | squamous cell carcinoma of the head and neck |
| Zanolimumab | HuMax-CD4 | mab | human | CD4 | rheumatoid arthritis, psoriasis, T-cell lymphoma |
| Zatuximab | | mab | chimeric | HER1 | cancer |
| Ziralimumab | | mab | human | CD147 (basigin) | ? |
| Zolimomab aritox | | mab | mouse | CD5 | systemic lupus erythematosus, graft-versus-host disease |

In another embodiment using photoacoustic/thermoacoustic technology, the circulating tumor, exosomes, or extracellular vesicles in the blood are quantified non-invasively by having a thermal energy source such as laser microwave, RF, or other unit mounted on the patient's wrist, neck, etc. and a receiver to count and record the sound wave generated by circulating cells to which the antibody-coated nanoparticles are attached.

In another embodiment, the ultrasonic receiver of the photoacoustic unit is an array of ultrasonic receivers mounted on a hand held probe. The hand held probe contacts the patient's skin via a gel placed over the area suspected to contain a tumor or lesion. It simultaneously records multiple photoacoustic signals from the lesion during thermal energy application. Thermal energy applied pulses can range from one per second to a million times or more per second. Each time a thermal pulse reaches the nanoparticles, the nanoparticles expand and create a photoacoustic/thermoacoustic response that is recorded by the photoacoustic receiver.

The probe can be moved in any direction, e.g., up and down, side to side, etc., over the skin while recording the sound waves from the nanoparticles. Using a processor in the photoacoustic/thermoacoustic unit, one uses the photoacoustic response data to construct a two- or three-dimensional image of the tumor. The hand held probe permits scanning any bodily surface, including but not limited to breast, eye, CNS, spinal cord, extremities, internal organs, eye, nose, chest, trachea, throat, abdomen, and urogenital organs. The data from the ultrasonic array probe of the photoacoustic/thermoacoustic unit is stored in a computer during the probe's motion, permitting video construction showing tumor shape, structure, location, etc. for video presentation, evaluation, and archiving.

In one embodiment, the unit is capable of storing vast quantities of data from photoacoustic signals. The unit is also capable of storing vast quantities of data from non-stationary tissues, e.g., circulating tumor cells and exosomes in blood vessels, that have accumulated antibody coated nanoparticles on their cell membranes. The targeted cells can also be any normal or abnormal circulating cell in the blood or lymphatic system. The photoacoustic unit reproduces signals from these mobile cells and/or exosomes as photoacoustic cinematography/angiography or video.

In one embodiment, the cinematography or video recording is done by the photoacoustic unit recording at least 30 frames/second of photoacoustic signals, and converting them into an image of a moving object. A cinematography or video is performed by obtaining at least 30 frames of photos of a moving object per second. In photoacoustic videography or photoacoustic angiography, 30 or more frames of pulse signals from the heated nanoparticles per second are needed to reproduce or convert the still images to a moving object, e.g., blood flow, etc. by the unit. Use of such a system is known: Peyman et al. Ophthalmic Surg Laser Imaging 43 (2012) 143-51 doi: 10.3928.15428877-20120105-01 showing, however, lower resolution because no nanoparticles or photoacoustic imaging system was employed, and expressly incorporated by reference herein in its entirety.

In one embodiment the photoacoustic processor converts the microscopic still images to a video or photoacoustic angiography; since the only moving parts in the vessels that are targeted with antibody coated nanoparticles are the circulating tumor cells or exosomes, extracellular vesicles or bubbles covered with antibody coated nanoparticles that are heated by a pulse of thermal energy produces an internal ultrasonic pulse signal recorded by the photoacoustic receiver. A moving image of the cells and exosomes can be created by the unit whether the cells are on the tumor interior or exterior.

Nanoparticle assisted photoacoustic video-angiography or nanoparticle assisted photoacoustic cinematography is novel and inventive. All "photoacoustic" terminology has previously been used for describing tissue heating or the difference in the temperature between two tissues, vessels vs. skin, and has been done with light alone, not in combination with nanoparticles with cell penetrating peptide (CPP), activating CPP (ACPP), biotin, streptavidin. In one embodiment, the method is performed for therapy by providing the patient with at least one antibody-coated functionalized nanoparticle having a detectable property, with the antibody targeting the functionalized nanoparticle to a specific patient site, then heating the nanoparticles to generate a photoacoustic signal, i.e., thermal therapy, and imaging to visualize any localized nanoparticle at the site. The ultrasonic receiver of the photoacoustic unit is an array of ultrasonic receivers mounted on a hand held probe simultaneously recording multiple photoacoustic signals from the lesion during thermal energy application which in one embodiment is pulsating. The array of ultrasonic receivers of the photoacoustic unit mounted on a hand held probe simultaneously records multiple photoacoustic signals from the lesion or vessels during thermal energy application, reproducing motion of moving nanoparticles and/or cells as a nanoparticle assisted photoacoustic video-angiography or nanoparticle assisted photoacoustic cinematography.

In another embodiment, software associated with the photoacoustic/thermoacoustic unit can enhance either or both the photoacoustic signals and resulting images. Enhancement may facilitate differentiating exosomes from circulating cells due to the smaller exosome size. All exosomes or other types of extracellular vesicles are less than one micron; in contrast, tumor cells are five to twenty times larger than exosomes. The inventive system for the first time permits in vivo observation and separation of exosomes from tumor cells, and separation of circulating tumor cells from a tumor mass. The separated cells or cell structures can be observed, counted, and quantified to assess the therapeutic effect of a procedure on tumor cells.

In another embodiment, after imaging and therapy, the biomarkers are collected from liquid biopsies and compared with those obtained prior to therapy in different post-operative periods to confirm the therapeutic effect of the procedure and prognosticate the condition.

In another embodiment, the antibody coated nanoparticles are conjugated and administered with checkpoint inhibitors along with known immune therapy agents and vaccines to facilitate circulating killer cells attack and removal of tumor cells.

In another embodiment, the vaccines with or without VLP facilitate circulating killer cells attacking and removal of tumor cells, and the antibody coated nanoparticles are administered with checkpoint inhibitors, such as PD-1, PD-L1, CTLA-4, Jagged 1 inhibitor 15D11, etc. and Rock inhibitors (e.g., Fasudil or Botox) or Wnt inhibitor, such as niclosamide, ivermectin, etc., and for the future management of the tumor recurrences in the patient or treatment of metastatic disease.

In another embodiment, polymeric nanoparticles or polysaccharide or synthetic polymers or porous silicon nanoparticles and/or microparticles or magnetic luminescent porous silicon nanoparticles and/or microparticles or antibody coated nanoparticles conjugated with (alpha)-cyclodextrin, (beta)-cyclodextrin, (gamma)-cyclodextrin, hydroxypropyl-b-cyclodextrin (bHPCD) conjugated with biomarkers are administered to enhance a vaccination effect and are taken up by antigen presenting cells.

In one embodiment, genetic analysis of the patient is performed to determine a sequence of the gene that is mutated. A sample of the patient's blood is analyzed for any of the following indicia of the presence or a neoplasm or a predisposition to a neoplasm: specific tumor biomarker(s), non-specific tumor biomarker(s), extravascular vesicles, circulating tumor cells, tumor micro RNA, micro DNA, or any other tumor indicator. RNA sequencing reflects the dynamic nature of gene expression for detection of RNA fragments, including mRNA, noncoding RNA, chimeric RNA, pathogen RNA, extracellular RNA, etc.

Examples of biomarkers have been previously disclosed. Other biomarkers include DNA hypermethylation, the presence of ZNF154 in colon, lung, breast, stomach, and endometrial tumor, and the stem cell marker NANOG, a mitochondrial oxidative phosphorylation/fatty acid oxidation molecule in highly malignant tumor-initiating stem-like cells (TICs) that reprograms mitochondrial metabolism.

Use of results from a patient's genetic analysis advantageously permits selection of a therapeutic agent, along with antibody-coated nanoparticles conjugated with porous silicon nanoparticles and/or microparticles or thermosensitive polymers and thermotherapy, to provide the greatest efficacy against cancers that are smaller than 4 mm in diameter. In general, such cancers have not grown to a size whereby they show genetic differentiation of the cancer cells. Treatment of these small cancer cells can thus include treatment of the cancer stem cell(s). In one embodiment, nanoparticles with cell penetrating peptide (CPP), activating CPP (ACPP), biotin, streptavidin activated by electromagnetic radiation, either in vitro or in vivo, enhance both gene transfer and cell proliferation of any desired cell, including stem cells, and by the using CRISPR-cas9 mediated Homology—Independent Targeted Integration (HITI) or Homology Directed Repair (HDR).

In one embodiment, the patient's blood is processed to isolate the patient's own natural killer (NK) cells, i.e., a type of lymphocyte that is part of the patient's innate immune system, and dendritic cells, i.e., immune cells that process antigen material and present it on the cell surface to T cells of the immune system). NK cells and dendritic cells are isolated from a patient's blood using commercially available kits known in the art, e.g., EasySep™ and RosetteSep™ STEMCELL Technologies Inc., Tukwila WA; NK Cell Isolation Kit, Meltinyi Biotech, Bergisch Gladbach Germany. The natural killer cells/dendritic cells are rendered sensitized to the tumor in vitro. Sensitization is accomplished by co-culturing the patient's natural killer cells and/or dendritic cells with IL-2 and the antibody-coated nanoparticles containing the optional penetration-enhancing agents and/or thermosensitive polymers as previously described. The patient's sensitized natural killer cells/dendritic cells are then administered to the patient at intervals to provide a booster immune therapy, much as a vaccine booster injection does. The vaccine may be administered with or without VLPs. IL-2, IL17 is a protein produced by the T cells. When IL-2 is conjugated with the thermosensitive antibody coated nanoparticle, and administered with checkpoint inhibitors, such as PD-1, PD-L1, CTLA-4, Jagged 1 inhibitor, 15D11, etc. and Rock inhibitors, such as Fasudil or Botox, or Wnt inhibitors, such as niclosamide, ivermectin, and Selamectin and alpha lipoidic acid (ALA) or small molecule Wnt inhibitors upon controllable temperature release, IL-2 is systemically available to enhance a T-cell response in the patient by cell sensitization and proliferation as a vaccine or treatment of metastatic disease.

Thermal damage to the tumor cell membrane as a part of nanoparticle assisted thermotherapy releases antigens that, in vivo, activate and stimulate a dendritic cell immunogenic response. The activated dendritic cells induce a signal that additionally activates T cell-driven tumor cell damage or killing.

In one embodiment, the medium used to culture NK/dendritic cells contains viral like particles (VLP), immune stimulators with cell penetrating peptide (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD). The NK/dendritic cells pick up the VLP or immune stimulation with toll like receptor 7/8 or interferons antibody coated nanoparticles dendrimers and enhance sensitization against the tumor. If tumor cell biopsy specimens are available, NK cells/dendritic cells are cultured from these biopsy specimens which additionally contain tumor lysate, killed circulating tumor (CT) cells, and their extracellular vesicles (ECV). In one embodiment, porous silicon nanoparticles and/or microparticles or other nanoparticles, with thermosensitive polymers and conjugated with tumor antibody and VLP, immune stimulation with toll like receptor 7/8 or interferons antibody coated nanoparticles, dendrimers are administered to the patient intravenously, as the first step of tumor vaccination and therapy. The nanoparticles become attached to the tumor cells within a few minutes after administration.

In one embodiment, the tumor biomarkers from a patient's blood are identified, and anti-tumor antibodies are prepared, using conventional antibody techniques known in the art. The antibodies may be monoclonal, polyclonal, humanized, etc.; tumor antibodies also includes aptamers (oligonucleotide or peptides that bind to a specific target). The antibodies/aptamers are then coated on diagnostic or therapeutic nanoparticles or quantum dots, and conjugated with checkpoint inhibitors such as PD-1, PD-L1, CTLA-4, Jagged 1 inhibitor 15D11, etc. and Rock inhibitors, such as Fasudil, hydroxyl Fasudil, etc., botox, 3C exoenzyme etc. or Wnt inhibitors, such as niclosamide, as a vaccine or treatment of metastatic disease, which are then systemically administered to the patient. In vivo, the tumor-antibody-coated nanoparticles seek the tumor cells via the specificity of the anti-tumor antibody component. In one embodiment, adding a cell penetration enhancing agent to the polymer or other coating facilitates penetration of the tumor-antibody-coated nanoparticles into a tumor cell. Cell-penetration enhancing agents render the nanoparticle complex more biocompatible, and have been previously disclosed; they include cell penetrating peptide (CPP), activated CPP (APCC), (poly)ethylene glycol (PEG), biotin streptavidin, etc.

In one embodiment, as previously disclosed, the tumor-antibody-coated nanoparticles are also coated with a thermosensitive polymer that dissolves at a particular temperature, e.g., a polymer such as chitosan that dissolves at a temperature of 40° C.-43° C., and/or an arginine rich polymer, etc.

This coating, in addition to its thermosensitive properties with cell penetrating peptides (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD), is administered with checkpoint inhibitors such as PD-1, PD-L1, CTLA-4, Jagged 1 inhibitor 15D11, etc. and Rock inhibitors, such as Fasudil, Botox, 3C exoenzyme, etc., or Wnt inhibitor, such as niclosamide, etc., and includes one or more medicaments, genes, etc. thus providing additional therapy to the patient upon administration and thermotherapy as a vaccine or treatment of metastatic disease. In one embodiment, adding a phospholipase, anti-phospholipid antibody, toxin (snake, scorpion, bee venom, etc. to the polymer or other coating enhances the damage to the cell membrane from an anti-tumor antibody coated nanoparticle. This beneficially increases the hyperthermal damage to cancer and other undesirable cells due to toxin release from the nanoparticles' coating of thermosensitive polymer at 40° C.-43° C.

In one embodiment, genes are provided that have a stimulatory action in response to light or ultrasound. An example of such a gene is the opsin gene and members of the opsin family. In this embodiment, such genes are provided to regulate cell membrane polarization and depolarization. Such genes can thus controllably create an action potential in the membrane of an excitable cell, such as a retinal cell, or a non-excitable cell such as a tumor cell. Controllable regulation may drive a permanent depolarization state to render the cells accessible to a desired medicament for cell destruction.

In one embodiment, combinations of genes can be used for controllable regulation. As an example, genes responding to light to produce action potential, combined with genes that can modifying a defective gene(s) in the cells of an organ, e.g., eye, brain, lung, spinal cord, peripheral nerve, lung, digestive tract, can be used in combination to facilitate regulation of actions including swallowing, breathing, gland secretion, etc., to restore the normal function of the organ. As another example, genes responding to light to produce an action potential, combined with inhibitory genes such as siRNA, RNAi, microRNA, can be used to inhibit tumor function by simultaneous depolarization of the tumor cells. These genes can additionally be combined with chemotherapeutic agent to work synergistically and damage the tumor cells.

Systemic administration of tumor antibody coated nanoparticles, coated with thermosensitive polymers and a cell penetration facilitating agent, targets the nanoparticles toward the tumor cell membrane. External energy is applied by a thermal delivery device that uses energy (electromagnetic radiation, microwave radiation, radiofrequency waves, an alternating magnet, focused ultrasound, etc.) to increase the temperature of the nanoparticle. The heated nanoparticle absorbs more energy than the tissue surrounding the nanoparticle. The temperature increase causes the nanoparticles to expand. Expansion of the nanoparticles creates a photoacoustic, thermoacoustic, or ultrasound wave, whose sound wave amplitude correlates with the amount of the temperature increase, i.e., the degree of the temperature rise.

In one embodiment, the ultrasound wave is recorded by a transducer and is transmitted to a unit to image the nanoparticle increase in temperature as one-, two- or three-dimensional images. This unit is connected to the thermal delivery device via a computer to maintain the amount of thermal energy needed for the time required to heat the nanoparticles to the desired temperature and for the desired time period and thus release medicament(s), gene(s), CRISPR cas 9, to modify the mutated genes by using CRISPR-cas9 mediated Homology—Independent Targeted Integration (HITI) or Homology Directed Repair (HDR), VLP, immune stimulation, toll like receptor 7/8 or interferons antibody coated nanoparticles, dendrimers, etc. to stimulate immune response. These agents may also be against microorganisms, e.g., bacterial, viral, fungal, or parasitic agents, which have developed resistance to the therapeutic agents. For example, heated bacteria become more permeable to diffusion of appropriate medication; in contrast, non-heated bacteria remain resistant.

In one embodiment, nanoparticles coated with the desired antibody (e.g., anti-tumor antibody, anti-bacterial protein antibody, etc.) are administered to the patient to assure that the antibody-nanoparticle complex is in contact with the appropriate cells or tissues. It will be appreciated that the appropriate cells or tissues may include both circulating cells (e.g., ECV, endosomes, leukemic cells, etc.) and non-circulating cells (e.g., solid tumor).

In one embodiment, a small hand held photoacoustic unit with a small thermal delivery unit e.g. laser, microwave, or radiofrequency unit is placed externally over a subcutaneously located vessel to deliver a pulse of energy and to heat the nanoparticles attached to the circulating tumor cells and create a photoacoustic sound as they heat up. This records the sound wave each time a tumor cell passes by the external hand held unit, adjusts the temperature from 37° C.-43° C., thus assessing and quantifying non-invasively the circulating tumor cells using the hand held thermal imaging device.

In one embodiment, photoacoustic technology imaging is controlled to a low temperature of 37° C.-43° C., thus assessing and non-invasively measuring circulating cells using a hand held thermal imaging device. Imaging may be used in combination with any standard method, including but not limited to radiography, computed tomography (CT), magnetic resonance imaging (MRI), ultrasound, positron and other molecular imaging devices.

In one embodiment, nanoparticles are conjugated with VLP derived from plant viruses. In this embodiment, the VLP are used for cancer therapy by carrying sRNA, RNAi, etc. The host of these viruses are plants e.g. tobacco mosaic virus (TMV), bean yellow dwarf virus (BeYDV), etc., which cannot infect the patient. Thermal application of the antibody coated nanoparticles provides the control over when and where these particles are released to provide maximum benefit in immunotherapy. The VLP are generally immunogenic and do not require adjuncts to induce an immune response. These modified viruses are devoid of genetic components and cannot replicate in the body. However, if a specific gene of a specific protein e.g. an antibody, is conjugated with them and injected in the plant, the modified viruses produce large amounts of the antibody or protein in the plant, which can subsequently be extracted and used in human infective or non-infective diseases or to produce a vaccine to treat e.g. Alzheimer's disease etc. The thermal application at 41-43 degrees C. damages the VLP or other viruses and prevents their proliferation without reducing their immunogenicity. Once the antibody is produced, it can be used in diagnosing or guiding treatment to the affected area in combination with nanoparticles with or without VLP and drug delivery, and administering them with Rock inhibitors, such as Fasudil, botox, C3 exoenzyme, etc., or Wnt inhibitors, such as niclosamide to be used as a vaccine or for treatment of metastatic diseases as needed.

With respect to a gene(s) present in the polymer coating, e.g., an inhibitory gene such as siRNA, siDNA, RNAi, CRISPR to reduce the expression of checkpoint proteins by the tumor cells etc., or an appropriate checkpoint inhibitor, may be used with antibody coated nanoparticles with cell penetrating peptide (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD). Checkpoint inhibitors enhance cellular immune responses to tumor specific proteins in the cancer cells, as previously disclosed. In one embodiment, checkpoint inhibitors, such as PD-1, PD-L1, CTLA-4, Jagged 1 inhibitor 15D11, etc. and Rock inhibitors, such as Fasudil, botox or Wnt inhibitors, such as niclosamide, ivermectin, and Selamectin and alpha lipoidic acid (ALA) as a vaccine or for treatment of metastatic diseases needed or are combined with nanoparticle-assisted targeted immunotherapy as an adaptive T-cell transfer mechanism. These, along with the a CRISPR/cas9 or CRISPR interference (CRISPRi) complex, may perturb or modify the tumor genes by using CRISPR-cas9 mediated Homology—Independent Targeted Integration (HITI) or Homology Directed Repair (HDR).

With respect to medicament(s), the medicament(s) would be released locally present in the polymer coating or pluralities of the antibody coated nanoparticles during thermotherapy. For a medicament that is a biologic, local release permits agents to be concentrated at the desired site without being released systemically resulting in systemic toxicity the medicament may otherwise cause. As one example, anti VEGF agents, TNF inhibitors, antineoplastic medications such as taxol, antimetabolites, anti-inflammatory agents, steroids, checkpoint inhibitors, such as PD-1, PD-L1, CTLA-4, Jagged 1 inhibitor 15D11, etc. and Rock inhibitors, such as Fasudil, C3 exoenzyme, Botox, etc., or Wnt inhibitors, such as niclosamide, ivermectin, Selamectin, and alpha lipoidic acid (ALA), antibiotics, antiviral agent, etc. can be used as a vaccine or for treatment of metastatic diseases and become localize specifically at a tumor or other site at significantly higher concentrations to stop tumor neovascular growth or damage the tumor etc., without causing the known systemic complications such as heart attack, intestinal bleeding, kidney disease, liver disease, or suppressing the normal humoral or cellular immune response of the body, etc. as seen in routine chemotherapy or immune therapy. As another example, release of phospholipase enzymes can create a hole in the membrane of tumors or other cells to provide or facilitate entry of a medicament(s) and/or gene(s) entry into a cell.

In the inventive precision nanoparticle assisted-thermotherapy imaging (NATTI), the temperature of the tumor cell to which the nanoparticle is conjugated is controllably precisely increased. The temperature increases (a) releases a medicament(s) and/or gene(s) from a thermosensitive coating on the nanoparticle, and (b) enhances penetration of the medicament(s) and/or gene(s) through the open pores of the tumor cell membrane. NATTI technology includes a computer-controlled thermal energy delivery unit to ensure attainment of a desired increased temperature of the tumor for achieving the therapeutic goal. Controlling thermal energy delivery to achieve a temperature from 38° C. to 42° C. for drug delivery or more in the tumor-nanoparticle complex to a tumor, or to another tissue affected by a disease as directed by antibody binding to a corresponding antigen. It will be appreciated that the increased temperature may be maintained at the controlled desired level for any desired time interval, e.g., up to 1, 2, 3, 4, 5, 6, 7, 8, 9, 10, 11, 12, 13, 14, 15 minutes, or even longer, depending upon the need.

Typically, normal healthy cell membranes are comprised of the phospholipids phosphatidylserine (PS) and phosphatidylethanolamine (PE), which are located within the inner membrane and oriented toward the cell interior. However, for cancer cells, the orientations of PS and PE are flipped, so each oriented toward the cell exterior. The melting point of PS and PE is about 65° C.-70° C. degree. When the nanoparticles are heated to this temperature, the exposed PS and PE lipids of the cell membrane melt, and create a dehiscence in the cell membrane through which chemotherapeutic agents can freely flow into the tumor cell, killing the tumor cell.

For a medicament that is a chemotherapeutic agent, local release permits a higher concentration of a chemotherapeutic agent to be contained in the polymer coating, i.e., a supratherapeutic concentration, because it is confined to a localized site and would not result in systemic toxicity, yet still would achieve a higher therapeutic level at the tumor site. In one embodiment, a known existing antitumor chemotherapeutic agent is administered at a concentration that exceeds that of a concentration that would be administered under typical therapy, yet that does not result in patient toxicity. Similarly, one can use a toxic medicament(s) to locally perturb a cellular metabolic pathway or a specific cell cycle, e.g., local tumor cell perturbation. Such agents are generally not administered intravenously or orally because of their serious or fatal systemic toxicity and side effects. The concentration of the chemotherapeutic medicament(s) delivered by the inventive method is, in general, high locally, but less the 1/1000 of the concentration that would be required if the medicament(s) were to be effective if delivered systemically.

Use of precision nanoparticle assisted thermotherapy and imaging (NATTI) may be used to fine-tune the approach to perturb survival mechanisms of tumors or other pathological cells. It will be thus appreciated that the inventive method may be used as a rapid en mass treatment of a cancer or an organ. For example, it may be used as a preliminary treatment in advance of other therapies that in general have severe debilitating systemic complications such as immune suppression, etc. and which may take longer to obtain approval for their administration. Thus, nanoparticle assisted thermotherapy and drug delivery NATTI avoids the chemotherapy complication of damaging the patient's immune system as a result of one or multiple chemotherapeutic agents used in these late metastatic cancer patients.

The nanoparticle assisted thermoacoustic imaging technology, with cell penetrating peptides (CPP), activating CPP (ACPP), biotin, streptavidin along with thermal energy, drives the medicament(s), gene(s), CRISPR cas 9, VLP, immune stimulators combined with slow release polymers into the cancer cell, with simultaneous generation of an immune response to the cancer cell and inhibition of cancer cell proliferation by including siRNA, siDNA, etc. or RNAi, CRISPR to reduce the expression of checkpoint proteins by the tumor cells etc., along with simultaneously enhancing gene therapy by conjugating a CRISPR/cas9 or CRISPRi complex to the nanoparticle without relying on viral vectors by using CRISPR-cas9 mediated Homology—Independent Targeted Integration (HITI) or Homology Directed Repair (HDR) to correct or inhibit a genetic component of a tumor. Once inside a cell, e.g., a tumor cell or the cell of an organ, the gene(s), along with the CRISPR/cas9 complex or CRISPRi, enter the cell nucleus or mitochondria and precisely modify the gene pool of those cells. The RNA-guided bacterial endonuclease Cas9 is the effector protein of the type II CRISPR/Cas9 system that detects and subsequently generates a double-strand break (DSB) in target DNA. This may treat a disease caused by a gene deficiency, or add a new useful gene(s), or remove and possible replace a gene, in the cell nucleus or the mitochondria by the using CRISPR-cas9 mediated Homology—Independent Targeted Integration (HITI) or Homology Directed Repair (HDR).

The gene(s) and/or medicaments(s) may be delivered to a specific site, but not released in the circulation from the nanoparticles until reaching the required elevated temperature and after attaching to the tumor or other desired cells or desired location. It will be appreciated that the inventive method can be used in therapy for non-neoplastic diseases. As one example, the amyloid plaques present in Alzheimer's disease may be used to produce anti-amyloid plaque antibodies and treated by the inventive method. As another example, bacteria in patients with severe sepsis refractory to standard antibiotic therapy, e.g., patients with methicillin-resistant *Staphylococcus aureus* (MRSA) etc., may be used to produce anti-bacterial antibodies and treated by the inventive method. In this example, the method may be combined with extracorporeal treatment of blood, using a thermal energy delivery unit to provide electromagnetic radiation, radiofrequency waves, microwaves, focused ultrasound, an alternating magnetic field, etc., under the control of the described NATTI unit, to controllably achieve a temperature of 42° C.-45° C. to kill the bacteria prior to cooling the blood to the normal 37° C. prior to reinfusion to the patient.

In addition, increasing the temperature of the nanoparticles incrementally from 37° C.-43° C. allows precision nanoparticle assisted thermotherapy and imaging (NATTI) to release a gene(s) or medicament(s) from the nanoparticles. It will be appreciated that the method beneficially permits imaging a tumor or other desired cells, such as Alzheimer's plaques, that are present in a small lesion otherwise invisible by conventional imaging methods such as radiography.

The immune response is generated by two different mechanisms. One mechanism is by releasing the VLP, immune stimulation with IL2, IL 17, toll like receptor 7/8 or interferons antibody coated nanoparticles or dendrimers with cell penetrating peptide (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD), which then stimulates a cellular immune response at the site of the tumor. The other mechanism is by the thermotherapy-damaged tumor cells releasing their antigenic material in and beyond the surrounding tissues, creating a more active cellular immune response due to the additional tumor antigens present, and drawing the patient's immune cells, dendritic cell, T-lymphocytes, B-lymphocytes, macrophages, etc., to the tumor location. This mechanism also advantageously provides immune memory functioning as an internal vaccination method. Specifically, local release of antigens from damaged tumor cells enhances a patient's immune response to a large amount of other tumor cell associated antigens, creating a form of in vivo vaccination. Such vaccination can be provided as needed, e.g., annually, at specific intervals, upon specific events, etc. to prime the patient's immune cells against any future tumor cells, and protects against reappearance of any tumors with similar antigenic components. For example, vaccination may be administered annually or biannually or between annual and biannual administration indefinitely, unless new biomarkers are discovered in the patient, necessitating additional and/or earlier therapy.

In addition, the inflammatory process created as a result of the immune therapy and cellular response increases the temperature of the tissue involved, which is also recorded using photoacoustic technology imaging to image the tumor location and its potential metastatic lesions anywhere in the body.

This embodiment results in precise, local, internally-induced immunotherapy and simultaneous vaccination. The antigen, e.g. VLP, immune stimulation with IL 3, toll like receptor 7/8 or interferons antibody coated nanoparticles, dendrimers are delivered intravenously with thermosensitive polymers conjugated with antitumor antibody coated nanoparticles. The VLP and immune stimulators/thermosensitive polymers are released from these nanoparticles only when the temperature of the nanoparticle is increased to 40-43 C degrees, and the nanoparticles are localized only at the tumor site, due to the specificity of the anti-tumor antibody with which the nanoparticles are conjugated.

As previously disclosed, various nanoparticle types, compositions, configurations, etc. are possible, including the following non-limiting examples: organic, synthetic, metallic, non-metallic, magnetic, non-magnetic, paramagnetic, etc., configurations such as a nanosphere, nanotube, nanoshell, nanocage, nanocarbon, etc., including quantum dots, dendrimers, liposomes, or solid lipid nanoparticles, piezoelectric nanoparticles, etc.

In one embodiment, piezoelectric nanoparticles are stimulated by an ultrasonic unit, providing a therapeutic effect by inducing an electric current in cells. Depending upon the frequency, this exposure can kill cells on one hand, or it can enhance growth of specific cells on the other hand. Application of thermal energy at a frequency in the range of 1 Hz-20 Hz promotes cell growth. Application of thermal energy at a frequency greater than about 60 Hz damages cells. Cell death is desirable for treating pathologies such as cancer. However, cell proliferation is desirable to facilitating tissue regeneration. For example, in this embodiment, a patient with a stroke, or a myocardial infarction, or a spinal cord injury, may be treated to regenerate brain, heart, nerve tissue respectively. In this embodiment, the antibody used is targeted to the damaged cells, i.e., neurons, cardiac cells, etc., and treatment is with a pulsed frequency of 1 Hz-20 Hz or more is provided for 1 min-10 min. It will be appreciated that this embodiment permits stem cells to be controllably either stimulated or inhibited.

In one embodiment, the nanoparticle stimulates proliferation of in vitro cultured cells when the nanoparticle is exposed to and absorbs light pulses of low frequency, i.e., frequencies in the range of 1 Hz-20 Hz. Conversely, in one embodiment, the nanoparticle inhibits cell proliferation when the nanoparticle is exposed to and absorbs light pulses of very high frequency, i.e., frequencies in the range of >30 Hz-100 Hz). Thus, selecting the frequency of the thermotherapy, and thus the frequency to which the tumor antibody-coated nanoparticles or solid lipid nanoparticles are exposed, adds to the mechanisms of therapy the patient receives if the light pulses are at low frequencies, i.e., no higher than about 20 Hz.

In one embodiment, after sensitization of the immune cells with the tumor antigen, functionalized quantum dots with antibody coated against cell membrane of immune cells is added so that the cell membranes of the immune cells carry a marker that can be made visible with specific wavelength of light extracorporally.

In one embodiment, antibody coated nanoparticles or solid lipid nanoparticles are conjugated with thermosensitive polymers containing VLP/medication/genes, and administered with checkpoint inhibitors, such as PD-1, PD-L1, CTLA-4, Jagged 1 inhibitor 15D11, etc. and Rock inhibitors, such as Fasudil or botox, or Wnt inhibitors, such as niclosamide etc., and intravenously administered to a patient at a far lower level than would be toxic to the body (i.e., $\frac{1}{10}$ to $\frac{1}{100}$ of the non-toxic dose approved by the FDA). The VLP are released from the thermosensitive nanoparticles or solid lipid nanoparticles by thermal application at temperatures of 41° C.-43° C. The increase in temperature is achieved initially or in the post treatment tissue using, e.g., activation by light, electromagnetic radiation, microwave radiation, radiofrequency waves, focused ultrasound, or alternating magnetic field to preferentially heat the nanoparticles because of their high surface to volume ratio, and because the selected molecular composition of the nanoparticles or solid lipid nanoparticles preferentially absorbs more thermal energy than the surrounding normal cells. The tumor cells to which the nanoparticles are attached are also heated. The thermal energy may also damage the VLP without reducing its immunogenicity at a temperature or 41-43 degrees C. so that there is no chance of multiplication of the VLP in the body.

In one embodiment, the increase in the temperature of the nanoparticles or solid lipid nanoparticles results in their thermal expansion. Thermal expansion of the nanoparticles produces an ultrasonic wave that passes through the body, is captured by a receiver, the ultrasonic pulse is converted and amplified by an ultrasonic, photoacoustic, or thermoacoustic unit, imaged as a thermoacoustic signal or as nanoparticle assisted thermoacoustic signal, and converted by a computer to images, in one-, two-, or three-dimensions, of the temperature and the lesion.

In one embodiment, the photoacoustic or nanoparticle assisted thermoacoustic unit controls the thermal energy delivery unit via a processor to maintain the temperature of the nanoparticles or solid lipid nanoparticles at a predetermined temperature as a closed circuit once the nanoparticles have attached to the tumor cells. An increase in the temperature to which the nanoparticles are exposed, i.e., at the nanoparticle level, from 37° C. to 41° C.-43° C. melts the thermosensitive polymers coating the nanoparticles or solid lipid nanoparticles, releasing under control the conjugated VLP, medication/gene, CRISPR cas 9 which are attached to the thermosensitive antibody coated nanoparticles without relying on viral vectors, locally at the desired site. This method is particularly effective in small tumors, i.e., tumors less than 4 mm in diameter, because the tumor stem cells are still present at the original tumor site and can be simultaneously either genetically modified by the gene(s) using CRISPR-cas9 mediated Homology—Independent Targeted Integration (HITI) or Homology Directed Repair (HDR) or damaged, or killed and eliminated before metastasis has occurred.

In one embodiment, a plurality of the antibody-coated nanoparticles or solid lipid nanoparticles are injected into a patient's circulation with the cultured and tumor-sensitized NK cells/dendritic cells to target the tumor. It will be appreciated that such thermal damage to tumor cells, and a NK cellular response, generates and releases relatively large quantities of lytic enzymes and other cellular contents. In the case of smaller tumors, the released substances are of smaller quantities, but for larger tumors it become necessary to remove them from the blood, by plasmaphoresis, plasma exchange, etc. These substances released into a patient's circulation, may be thought of as cellular debris or detritus, to prevent an immunogenic or cytokine storm in the body.

In one embodiment, the patient receiving the inventive therapy undergoes plasmapheresis to remove, e.g., such cytokines, enzymes, dead cells, etc. from the circulation. Plasmaphoresis is a known method to remove components from blood plasma. Because the patient's plasma is treated extracorporeally, then reinfused, in contrast to reinfusing only cellular components of the patient's blood, plasmaphoresis also beneficially detoxifies the patient's plasma without compromising blood volume and with minimal or no fluid loss. This technique avoids the serious complications and side effects of simply returning the cellular components of the blood to the patient. Additionally, all precautions are observed to avoid hypotension and loss of calcium ions in the process of citrate anticoagulation that this procedure requires. The patient can be treated initially with presently available anticoagulants such as heparin, coumadin, etc., which can be immediately neutralized post-procedure. Neutralization uses standard techniques known in the art, such as calcium, etc. Hemofiltration treatment is performed with activated carbon, treatment on non-ionic exchange resins, etc. for removing free toxin and also toxin bound with plasma proteins, etc. as in renal dialysis methods. The process may be instituted or repeated as needed, e.g., if the tumor reappears. The addition of Rock inhibitors or Wnt inhibitors along with other therapeutic agents can reduce the overt inflammatory response seen in immune therapy or an auto immune disease.

In one embodiment, to prevent a severe autoimmune response after tumor immunotherapy, one uses extracorporeal plasmapheresis. A strong pulse of light energy is applied to a tube containing blood cells to achieve a temperature up to 60° C. to kill immune cells containing quantum dots. The blood is then passed through a dielectrophoresis system to characterize and remove dead or live T-cells, sensitized killer cells, and tumor cells, prior to re-infusing the same blood or performing a blood transfusion in the patient while simultaneously administering immunosuppressive agents, including a biologic, to reduce the severe autoimmune response often seen after tumor immunotherapy.

The size of the nanoparticle may vary, and may vary depending on the site of therapy and imaging as well as other factors. In one embodiment, the nanoparticle size ranges from 1 nm to 999 nm or more. In one embodiment, the nanoparticle size ranges from 1 nm to 20 nm, which is ideal for use in the eye and central nervous system to permit the nanoparticle access to the intercellular space, and also ideal for renal clearance without generating systemic side effects. Nanoparticles having a size less than 10 nm in diameter, and not bound to a tumor, i.e., nanoparticles that are free in the circulation, undergo rapid renal elimination from the body within a few hours of administration. Only nanoparticles attached to the tumor cells remain in the body. This results in a novel form of simultaneous local thermotherapy and vaccination.

The localized thermotherapy component of the method damages the tumor cells, thus disseminating tumor cell-associated antigens into the circulation, generating a cellular immune response to the various tumor biomarkers that were originally present. This dual thermotherapy and cellular response augments the effect of both immunotherapy and thermotherapy. The inventive method augments immunotherapy methods that relied on T-cells that had been sensitized to just a few tumor markers, or that relied only on checkpoint inhibitors to prevent the tumor cells' sequestration from T-lymphocytes. Previous methods of tumor vaccination used intradermal or subcutaneous antigen administration, with the antigen taken up by antigen presenting cells, e.g., dendritic cells, to generate specific killer cells only at a location remote from the specific tumor site. The inventive method augments the previous immunotherapy methods by combining immunotherapy to act synergistically with thermotherapy locally at the tumor site, thus preventing exposure of the entire body to therapeutic agents or checkpoint inhibitors that cause immune suppression or auto-immune disease.

In one embodiment, cultured killer cells sensitized to a tumor are administered simultaneously with the anti-tumor antibody coated nanoparticle-conjugated VLP to attack the tumor cells by the patients t-lymphocytes etc. and remove the dead tumor cells. For example, an intradermally administered antitumor antibody-coated nanoparticle with VLP can be administered with checkpoint inhibitors such as PD-1, PD-L1, CTLA-4, Jagged 1 inhibitor 15D11, etc., and Rock inhibitors, such as Fasudil, botox or Wnt inhibitors, such as niclosamide, in subsequent rounds of therapy during a postoperative period to induce an immune response as needed. This embodiment decreases the likelihood of, or prevents potential recurrences of the tumor or treats a recurrence of a tumor as a vaccination or therapy in recurrences. Since tumor recurrences are generally non-sensitive to ordinary therapy, it might be important in some cases that vaccination is done along with the checkpoint inhibitors to be able to attack the tumor cell recurrences that potentially have survived the previous therapy, in addition to providing Rock inhibitors or Wnt inhibitors that reduce excessive inflammatory disease and discourage tumor cell proliferation.

In one embodiment for use in larger tumors of a sufficient size for biopsy, an antibody directed to the tumor lysate (TL) is used as a source of tumor-associated antigens (TAAs), and is conjugated with the nanoparticles or solid lipid nanoparticles for generating therapeutic anti-tumor immune responses. One can generate in vivo immunity against multiple TAA simultaneously from the killed or damaged tumor cells during the thermotherapy. This embodiment broadens the repertoire of TAA-specific T-cell clones available for activation or therapy of these tumors.

In one embodiment, after an initial thermotherapy procedure, a blood sample is obtained from the patient. This blood sample contains released tumor antigens that are recoverable prior to treatment by the inventive method using various immunoassays or methods of searching for biomarkers. The tumor antigens are then used to generate, in vitro, additional T-cells that are sensitized to many TAA for future use in, along with VLP for vaccination, and are administered with checkpoint inhibitors, such as PD-1, PD-L1, CTLA-4, Jagged 1 inhibitor 15D11, etc., and Rock inhibitors, such as Fasudil, etc. or Wnt inhibitors, such as niclosamide, etc. to the same patient to enhance the immune response as a vaccine or to treat potential recurrences of the same tumor.

In one embodiment, immunostimulatory oligonucleotide-loaded cationic graphene oxide, carbon nanotube, gold/iron, iron/zinc oxide, or cadmium sulfate nanoparticles are combined with photothermally enhanced immunogenicity to achieve combined thermo-immune therapy. In one embodiment, RNA oligonucleotides/graphene or graphene oxide, or long double stranded RNA/graphene oxide induces a controlled immunostimulation in combination with oncogene silencing RNAi.

Nanoparticles, dendrimers, carbon nanotubes, lipid-based carriers, micelles, gold nanoshells/nanocages, PLGA, chitosan, PEI cationic lipid, and cationic polymers with cell penetrating peptides (CPP), activating CPP (ACPP), biotin, streptavidin or antibody coated nanoparticles conjugated with (alpha)-cyclodextrin, (beta)-cyclodextrin, (gamma)-cyclodextrin, hydroxypropyl-b-cyclodextrin (bHPCD) are useful for gene therapy, gene delivery, by using CRISPR-cas9 mediated Homology—Independent Targeted Integration (HITI) or Homology Directed Repair (HDR) and immunotherapy. These have the advantages of being easily prepared, biodegradable, non-immunogenic, non-toxic, and water soluble.

EXAMPLE 1

T cells and dendritic cells are obtained from a patient's blood, and grown in culture along with a tumor or other antigen, plus nanoparticles or solid lipid nanoparticles coated with thermosensitive polymers conjugated with antigen and VLP using culture methods known in the art.

The nanoparticle complex is injecting them along with checkpoint inhibitors and IL-2. The inventive method is applied, killing tumor cells, and increasing the response of T-cells and dendritic cell.

The patient's blood is assessed for new biomarkers from the dead cells.

The cultured T-cells and dendritic cells are harvested, along with the nanoparticle-coated antigen plus VLP or RNA or DNA phages. These are stored under appropriate conditions, and reinjected into the patient with low dose coated nanoparticles or systemic medicaments to be administered with checkpoint inhibitors such as PD-1, PD-L1, CTLA-4, Jagged 1 inhibitor 15D11, etc. and Rock inhibitors, such as Fasudil or Wnt inhibitors such as niclosamide as needed, e.g., semi-annually, annually, biannually, etc. as a vaccination or in tumor recurrences in metastatic disease, with repetition as needed. This is followed up with counting or quantifying circulating DNA, exosomes or circulating cells to recognize potential tumor recurrences.

EXAMPLE 2

A checkpoint inhibitors and rock inhibitors, e.g., Botox up to 50-100 picograms (pg), or 100 picograms (pg) to 1 nanogram (ng) or more or fasudil from 100 picograms (pg) to 10 nanograms (ng) or 50 nanograms (ng) to 1 milligrams (mg) or Wnt inhibitors, e.g., niclosamide is added to a thermosensitive polymer conjugated with antibody coated pluralities of nanoparticle for controlled release with the checkpoint inhibitor using the inventive controlled thermotherapy, NATTI, to release the medication locally at temperature of 41-43 C degrees along immune stimulators, such as VLP to treat a patient with breast, colorectal, glioblastoma, prostate, eye or skin melanomas, pancreatic, lung cancer, and/or ovarian cancer, etc. A checkpoint inhibitor, such as nivolumab or PD-L1, CTLA-4, Jagged 1 inhibitor 15D11, etc. and Rock inhibitors, such as Fasudil or botox, or Wnt inhibitors, such as niclosamide, ivermectin, and Selamectin, and alpha lipoidic acid (ALA) is combined with pluralities of antibody coated nanoparticle assisted targeted immunotherapy for adaptive T-cell transfer to overcome the limitations of standard immunotherapy and prevent a cytokine storm. In one embodiment the Rock inhibitor Fasudil can be taken orally at the dose of 40-80 mg as needed and niclosamide 1-2 gram once or repeated in a week, ivermectin and/or Selamectin also can be given orally at a dose of 1 gram orally for a period of time during and shortly after thermotherapy for a few days as needed.

EXAMPLE 3

Nanoparticles or solid lipid nanoparticles are conjugated with a chimeric receptor, a CD19 protein that is found only on B cells, along with the T-cells cultured in vitro that expresses a chimeric antigen receptor (chimeric antigen receptor T (CAR T)-cells) to target abnormal B cells seen in leukemia along with PD-L1, CTLA-4, Jagged 1 inhibitor 15D11, etc. and Rock inhibitors, such as Fasudil or botox, or Wnt inhibitors, such as niclosamide. The reappearance of new biomarkers as neoantigens in these patients can be also treated in the postoperative period using the inventive method repeated therapy as vaccination along with Rock inhibitor encourage the abnormal mature cells to undergo apoptotic degeneration rather cell proliferation with abnormal genetic changes which is characterized by the tumors occurring as a result of aging process and not a pre-existing genetic mutation by using CRISPR-cas9 mediated Homology—Independent Targeted Integration (HITI) or Homology Directed Repair (HDR).

Plasmaphoresis is simultaneously performed or performed after treatment.

This example treats acute and chronic hematologic malignancies such as acute lymphoblastic leukemia, non-Hodgkin lymphoma, chronic lymphocytic leukemia, chronic myelogenous leukemia, etc.

EXAMPLE 4

Pluralities of antibody coated nanoparticles or solid lipid nanoparticles are conjugated with all-trans retinoic acid (ATRA) and arsenic trioxide to target leukemia cells in acute promyelocytic leukemia and used in the inventive method. The all-trans retinoic acid is released at the site of the tumor without exposing the entire body to the toxic medication, simultaneously, plasmophoresis is performed to clear all toxin released in the blood, along with leukemic cells. It is appreciated that other blood cell cancers are removed in the same session.

EXAMPLE 5

In a patient with a hematologic malignancy that is resistant to chemotherapeutic agents or immune therapy, NATTI is performed with gene delivery by using CRISPR-cas9 mediated Homology—Independent Targeted Integration (HITI) or Homology Directed Repair (HDR), along with chemotherapeutic agents, to target all immune cells initially without subjecting the patient to systemic heavy chemotherapy, followed by bone marrow transplantation, without exposing the entire body to systemic chemotherapy.

EXAMPLE 6

Pluralities of antibody coated nanoparticles or solid lipid nanoparticles or antibody coated nanoparticles conjugated with (alpha)-cyclodextrin, (beta)-cyclodextrin, (gamma)-cyclodextrin, hydroxypropyl-b-cyclodextrin (bHPCD) are conjugated with RNA that contains an aptamer, ribosomes, and siRNA or RNAi, CRISPR to reduce the expression of checkpoint proteins by the tumor cells etc., in a thermosensitive polymer and administered to using NATTI to target specific tumor cells.

EXAMPLE 7

The microenvironment of the cancer cell is modified by delivering medicaments that block the uptake of exosomal signals and prevent the uptake of ECV. Such medications include choloroquine, heparin, cytochalasin D, and ethylisopropyl amiloride are conjugated with polymeric coating and conjugated with antibody coated nanoparticles or solid lipid nanoparticles administered to the patient and released with NATTI. These medications are approved for patient use. The medicaments are provided using NATTI in conjunction with chemotherapeutic agents and rock inhibitors.

EXAMPLE 8

The inventive method provides nanoparticle assisted localized immunothermotherapy and thermotherapy for delivery of customized vaccines with or without VLP to target core mutations in a patient. The immune cells or T-cells that can attack those core mutations are identified via a cancer biomarker. The immune cells or T-cells are then cultured with the nanoparticles or solid lipid nanoparticles coated with thermosensitive particles and VLP adjuvants and IL-2. The antibody coated nanoparticles or antibody coated nanoparticles conjugated with (alpha)-cyclodextrin, (beta)-cyclodextrin, (gamma)-cyclodextrin, hydroxypropyl-b-cyclodextrin (bHPCD) with checkpoint inhibitors, such as PD-1, PD-L1, CTLA-4, Jagged 1 inhibitor 15D11, etc., and Rock inhibitors, such as Fasudil or Botox etc., or Wnt inhibitors, such as niclosamide, etc., are injected into the patient, controllably heated using a thermal energy source, and imaged, for specific patient, or those with metastatic disease or recurrences as immunotherapy, such as in breast cancer, prostate cancer, glioblastoma, lung cancer, melanoma, ovarian cancer, pancreatic cancer, intestinal or colon cancer, etc.

EXAMPLE 9

Antibody coated nanoparticles or antibody coated nanoparticles conjugated with (alpha)-cyclodextrin, (beta)-cyclodextrin, (gamma)-cyclodextrin, hydroxypropyl-b-cyclodextrin (bHPCD) are conjugated with RNA phage VLP, adjuvants, which is generally stable up to about 50° C. VLPs or adjuvants of the related RNA phage PP7 are crosslinked with inter-subunit disulfide bonds, rendering them significantly more stable. They exhibit high immunogenicity. Such nanoparticles complement the inventive NATTI technology and can be employed in anti-cancer and antibacterial treatment. Lytic phages attach to receptors on the bacterial surface, inject their genetic material through the bacterial membrane, and overtake the bacterium's transcription and translation machinery to synthesize new phages. The application of thermotherapy damages all VLP, phages, virocides or foreign protein and eliminate their future growth and potential adverse reactions.

EXAMPLE 10

To prevent a severe autoimmune response after tumor immunotherapy, before extracorporeal plasmapheresis, one uses the nanoparticle assisted thermotherapy and imaging system to apply heavy thermal energy to a tube containing blood cells and to achieve a temperature as high as 60° C. to kill the sensitized immune cells containing nanoparticles or solid lipid nanoparticles. Blood is then passed through a dielectrophoresis system to characterize and remove dead or live T-cells, sensitized killer cells, and dead tumor cells prior to re-infusing blood in the patient while simultaneously administering immunosuppressive agents and Rock inhibitors, including biologics. This reduces the severe autoimmune response often seen after tumor immunotherapy.

In one embodiment, pain is one of the most common symptoms of inflammation in the patient; pain can be observed in viral or bacterial infections, surgery or trauma, an auto immune response, e.g., rheumatoid arthritis, affecting the joints, spondylitis of the vertebrae, after spinal cord injury, diabetic neuropathy, Fibromyalgia, after radiation or traumatic injuries, or radiation therapy and chemotherapy of the malignancies, the so called radiation or chemotherapy induced neuropathy. Fibromyalgia is a chronic undefined disorder with the symptoms of widespread pain, stiffness, fatigue, tenderness, anxiety and/or depression. It can be associated with, hypothyroidism, polymyalgia rheumatic, autoimmune rheumatoid arthritis, lupus erythematosus and other inflammatory disorders. There is no cure for fibromyalgia and treatment has been so far limited to analgesics antianxiety/hypnotic agents, skeletal muscle relaxants antidepressants. In nerve injury, the aberrant nerve regeneration produces abnormal excitability or sensitivity to various mechanical or thermal or chemical stimulation and produces central sensitization and chronic pain sensation. The peripheral nerve injury regardless of its origin such as radiation neuropathy or diabetic neuropathy affects the vascular supply of the nerves and their glial cells which produce proinflammatory cytokines worsening the condition. In addition, the radiation induces vascular occlusion in the tissue with subsequent ischemia, release of TGF beta, oxygen free radicals (reactive oxygen species), inducing fibrous tissue proliferation and ultimately tissue fibrosis increase nerve compression and pain sensation. These phenomenon are a common complication of external x-ray radiation, proton beam radiation or local radioactive cobalt plaque implantation etc. radiation. The higher the radiation dose, the more likelihood of developing radiation neuropathy. The changes, depending on the radiated area, are called radiation-induced brachial plexopathy (RIBP), lumbosacral radiculo-plexopathy, acute lumbosacral plexopathy, post hysterectomy and radiation side effects, brachial neuropathy, peripheral neuropathy/fibrosis or radiation-induced peripheral neuropathy (RIPN), lid and conjunctival fibrosis and corneal scarring and cataract formation, lumbosacral radiculoplexopathy, and nerve trunk damage. Additional risk factors are diabetes mellitus or co-existence of diabetic neuropathy, arteritis, and collagen vascular diseases and simultaneous chemotherapy administered for cancer therapy. Delayed effects of radiation are extensive fibrosis within and surrounding nerve trunks, and ischemia by injury to capillary networks supplying the nerves, compensated for by neovascularization and nerve demyelination. Depending on the area that has been radiated one can observe, cranial nerve damage predominantly involving the optic nerve associated with acute loss of visual acuity, trigeminal neuropathy develops after cavernous sinus tumor therapy, radiation injuries involving the glossopharyngeal nerve with swallowing impairment; vagus nerve after thoracic radiation therapy for breast, upper limb injury with classic progressive brachial plexopathy, axial neurological injury, delayed brachial plexopathy with comorbidity of lymphedema such as in radical mastectomy with extended lymph node dissection, and simultaneous chemotherapy with cisplatin or taxol the symptoms varies from decreases sensory perception, to loss of the function affecting both the sensory and motor nerves with various degree of paresthesia, debilitating pain and often limited motor function of the affected area because of tissue fibrosis and loss of the nerve function. The therapy of these serious complications are in general limited, and a prophylactic treatment has not been done. The therapy has been limited to symptomatic treatment including non-opioid analgesics, tricyclic antidepressants and anti-epileptics or benzodiazepines, restriction of aggravating factors, Carbamazepine, inhibiting voltage-gated sodium channels, reducing the excitability of neural membranes, serotonin—norepinephrine reuptake inhibitors, Clodronate, pregabalin, topical lidocaine, opioids, analgesics, Capsaicin, N-methyl-aspartate (DMDA) inhibitor. Other topical agents such as amitriptyline, nifepidine, pentoxifyline, neuromodulators include electrical or chemical implantable and non-implantable devices that can modulate the pain sensation or nerve electrical signals. These require surgical implantation of the device that generates an electrical pulse that interferes with disease induced abnormal pulses that transmit pain sensation as with deep brain stimulation. These devices require complex surgical procedures and with time, the contact electrodes need to be changed, while the disease process continues to worsen despite these interventions.

The canonical Wnt/β-catenin plays an important role in the expression of several inflammatory molecules during acute or chronic inflammatory diseases affecting skin, mucosal surfaces, subcutaneous tissue, muscle, interstitial tissue of the body including the brain, lung, liver, intestine, genitourinary system, the conjunctiva, nasal, oral, and throat including dry eye syndrome.

In one embodiment, for a patient suffering from pain after radiation or combined with chemotherapy, the antibody coated nanoparticles with Wnt inhibitors and/or Rock inhibitors are administered either locally, as an ointment, suspension or injected to the area of radiation and neuronal pain; compounds are used, such as: FH535, IWP-2, PNU-74654, IWR-1endo. IWR-exo, Demethoxy Curcumin, CCT036477, KY02111, WAY-316606, SFRP, IWP, LGK974, C59, Ant1.4Br/Ant 1.4C1, Ivermectin, Niclosamide, apicularen, and bafilomycin, XAV939, XAV939, G007-LK and G244-LM, NSC668036, SB-216763, gemtuzumab, etc., small molecule Wnt inhibitor PKF118-310, the Wnt/β-catenin pathway inhibitor and fasudil, a rock inhibitor Fasudil (HA-1077), a selective RhoA/Rho kinase (ROCK) inhibitor, or Y-27632, a small molecule inhibitor of ROCK1 and ROCK2, Fasudil1-(5-Isoquinolinesulfonyl)-2 Methylpiperazine Calcium Channel Blockers, Membrane Transport Modulators, etc., Canakinumab ivermectin, or niclosamide, Botulinum Botox, all having a good penetration into the skin or mucosa, subcutaneous tissue, muscle, interstitial tissue of the body including the brain lung, liver, intestine, genitourinary system, intravenously or intra-arterially, or can be delivered as s slow release compound implanted or injected inside the tissue with any polymeric compound, such as the polymers previously disclosed (e.g., polycaprolactone, poly(glycolic) acid, poly(lactic) acid, polyanhydride) or lipids that may be formulated as antibody coated microspheres or antibody coated dendrimers or antibody coated nanoparticles, including quantum dots, nanotubes, or nanowires. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be injected into body cavities, intravenously, intra-arterially as antibody-coated nanoparticles and/or microparticles with (alpha)-cyclodextrin, or (beta)-cyclodextrin, or (gamma)-cyclodextrin, hydroxypropyl-b-cyclodextrin (bHPCD). In a formulation for topical application, the drug is slowly released over time as the liposome capsule degrades due to wear and tear from the surface of the skin or mucosa or in the tumor or interstitial tissue. In a formulation for injection and nano solid lipids, or liposome capsule degrades due to cellular digestion, other slow release polymers such as PLA, PGA, Polycaprolactone, microsphere, dendrimers) or as nanoparticles and/or microparticles of porous silicon or with (alpha)-cyclodextrin, or (beta)-cyclodextrin, or (gamma)-cyclodextrin, hydroxypropyl-b-cyclodextrin (bHPCD) are also utilized, or some such as Fasudil orally at doses of 40-80 mg. This is equal to 1 microgram/ml to 40 microgram/ml or to 80 microgram/ml or more for topical application having ranges of 40 ng/ml to 4 micrograms/ml, or 0.1 microgram/ml to 40 microgram/ml or more for topical applications without having the side effects of steroid preparation, in addition the following compounds are readily available and some have been approved by the FDA: potent ROCK inhibitor; orally bioavailable Fasudil hydrochloride, Inhibitor of cyclic nucleotide dependent- and Rho-kinases GSK 269962, Potent and selective ROCK inhibitor GSK 429286, Selective Rho-kinase (ROCK) inhibitor H1152 dihydrochloride, Selective Rho-kinase (ROCK) inhibitor Glycyl H 1152 dihydrochloride, Selective Rho-kinase (ROCK) inhibitor; more selective analogue of H1152, Cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride, Botox or botulinum toxin as injectable preparation of topical ointment or with slow release polymers described above. Available Wnt inhibitors include small molecule Wnt inhibitor PKF118-310, the Wnt/β-catenin pathway inhibitor, niclosamide, ivermectin etc.

In one embodiment, the antibody coated nanoparticles containing a coated Wnt inhibitor or rock inhibitor are administered locally as an ointment, or injected subcutaneously or intra-arterially, intravenously, interstitially to multiple areas, intramuscularly, by injecting a solution of 0.01-0.5 ml or more in a physiologic PH adjusted to 7-7.5 PH and osmolarity of 280-300 mOsm close to the major neurons on a patient suffering from the symptom of inflammation. In the patient, pain can be observed, in viral or bacterial infections, surgery or trauma, an auto immune response, e.g., rheumatoid arthritis, affecting the joints, spondylitis of the vertebrae, after spinal cord injury, diabetic neuropathy, etc.

In one embodiment, the antibody coated nanoparticles containing a coated Wnt inhibitor or rock inhibitor are administered locally as ointment, or injected subcutaneously or intra-arterially, intravenously, interstitially to multiple areas, intramuscularly, by injecting a solution of 0.01-0.5 ml or more in a physiologic PH adjusted to 7-7.5 PH and osmolarity of 280-300 mOsm close to the major neurons in a patient suffering from the symptom of inflammation. In the patient, the inflammation and pain is occurring after radiation or traumatic injuries, or radiation therapy and chemotherapy of the malignancies, the so-called radiation or chemotherapy induced neuropathy.

In one embodiment, the antibody coated nanoparticles containing a coated Wnt inhibitor or rock inhibitor are administered locally as ointment, or injected subcutaneously or intra-arterially, interstitially to multiple areas, intramuscularly, using a fine needle, injecting a solution of 0.01-0.5 ml or more in a physiologic PH adjusted to 7-7.5 PH and osmolarity of 280-300 mOsm close to the major neurons as prophylactic for prevention of the radiation complications such as neuropathy and fibrosis in the areas to be irradiated or that will be in the path of the beam of radiation.

In one embodiment, the antibody coated nanoparticles containing a coated Wnt inhibitor or rock inhibitor are administered postoperatively locally as an ointment, or injected subcutaneously or intra-arterially, interstitially, using a fine 23-32 gauge needle, injecting a solution of 0.01-0.5 ml or more in a physiologic PH adjusted to 7-7.5 PH and osmolarity of 280-300 mOsm to multiple areas, intramuscularly, close to the major neurons treated, the higher the radiation dose increased the likelihood of developing radiation neuropathy at the radiated area to the brachial plexus.

In one embodiment, the antibody coated nanoparticles containing a coated Wnt inhibitor or rock inhibitor are administered postoperatively locally as an ointment, or injected subcutaneously or intra-arterially, interstitially to multiple areas, intramuscularly, using a fine 23-32 gauge needle injecting a solution of 0.01-0.5 ml or more in a physiologic PH adjusted to 7-7.5 PH and osmolarity of 280-300 mOsm close to the major neurons treated higher the radiation dose after developing radiation neuropathy at the radiated area, close or to brachial plexus area.

In one embodiment, the antibody coated nanoparticles containing a coated Wnt inhibitor or rock inhibitor are administered locally as an ointment, or injected subcutaneously or intra-arterially, interstitially to multiple areas, intramuscularly, using a fine 23-32 gauge needle injecting a solution of 0.01-0.5 ml or more in a physiologic PH adjusted to 7-7.5 PH and osmolarity of 280-300 mOsm close to the major neurons as prophylactic for prevention of the radiation complications, such as neuropathy and fibrosis in the areas to be irradiated or will be in path of the beam of radiation.

In one embodiment, the antibody coated nanoparticles containing a coated Wnt inhibitor or rock inhibitor are administered locally as an ointment, or injected subcutaneously or intra-arterially, interstitially to multiple areas, intramuscularly, using a fine 23-32 gauge needle injecting a solution of 0.01-0.5 ml or more in a physiologic PH adjusted to 7-7.5 PH and osmolarity of 280-300 mOsm close to the major neurons and the area of radiation induced vascular occlusion in the tissue with subsequent ischemia, release of TGF beta, oxygen free radicals (reactive oxygen species), inducing fibrous tissue proliferation and ultimately tissue fibrosis, increased nerve compression and pain sensation where the Rock inhibitors, such as botox, inhibits TGF beta and subsequent fibrosis.

In one embodiment, the antibody coated nanoparticles containing a coated Wnt inhibitor or Rock inhibitor are administered locally as an ointment, or injected subcutaneously or intra-arterially, interstitially to multiple areas, intramuscularly, using a fine 23-32 gauge needle injecting a solution of 0.01-0.5 ml or more in a physiologic PH adjusted to 7-7.5 PH and osmolarity of 280-300 mOsm close to the major neurons and the area of radiation at the lumbosacral radiculo-plexopathy, acute lumbosacral plexopathy, post hysterectomy and radiation side inflammation and fibrosis, brachial neuropathy, peripheral neuropathy/fibrosis or Radiation-induced peripheral neuropathy (RIPN).

In one embodiment, antibody coated nanoparticles containing a coated Wnt inhibitor or rock inhibitor are administered, using a fine 23-32 gauge needle injecting a solution of 0.01-0.5 ml or more in a physiologic PH adjusted to 7-7.5 PH and osmolarity of 280-300 mOsm to a patient who has developed radiation complications, such as neuropathy and fibrosis in the areas that have been irradiated, or have been in the path of the beam of radiation.

In one embodiment, antibody coated nanoparticles containing a coated Wnt inhibitor or rock inhibitor are administered to a patient who has developed complication of the radiation neuropathy or fibrosis in the areas that have been irradiated or have been in the path of the radiation producing symptoms of pain and neuropathy, using a fine 23-32 gauge needle and injecting a solution of 0.01-0.5 ml or more in a physiologic PH adjusted to 7-7.5 PH and osmolarity of 280-300 mOsm.

in one embodiment, Rock inhibitors are administered with antibody coated nanoparticles conjugated with thermosensitive nanoparticles and Adalimumab, a humanized antibody, administered topically or subcutaneously at a nontoxic dose.

In one embodiment, the Wnt inhibitors or Rock inhibitors are administered with nanoparticles or dendrimers coated with thermosensitive polymers and conjugated with lactic or glycolic acid or combinations thereof, or nanoparticles or microparticles of porous silicon, and administered as drops or by injecting a solution of 0.01-0.5 ml or more in a physiologic PH adjusted to 7-7.5 PH and osmolarity of 280-300 mOsm in a patient who has developed complication of the radiation neuropathy or fibrosis in the areas that have been irradiated or have been in the path of the radiation, producing symptoms of pain and neuropathy.

In one embodiment, Rock inhibitors are administered or injected using a solution of 0.01-0.5 ml or more in a physiologic PH adjusted to 7-7.5 PH and osmolarity of 280-300 mOsm with antibody coated nanoparticles, dendrimers, liposomes, solid lipid nanoparticles, micro- or nanoparticles of porous silicone, etc. to a patient who has developed complications of radiation neuropathy or fibrosis in the areas that have been irradiated or have been in the path of the radiation, producing symptoms of pain and neuropathy.

In one embodiment, a formulation of Wnt or Rock inhibitors used to treat skin, mucosal lichen planus, as well as other conditions, is disclosed. Rock inhibitors and Wnt inhibitors are used as topical drops, spray applications, or injections into the lesion or surrounding tissue, or an as implantation in or on the in the tissue. For example, a topical administration may contain between about 10 pg/ml drug to about 50 .mu.g/ml drug in a formulation which may be applied at bed time or throughout the day. For injection, a dose of about 50 pg/ml to about 200 .mu.g/ml may be used as a surgical implant, for example, in a diffusible walled reservoir close to the major nerve in the treated area, or may be contained within an inert carrier such as microspheres or liposomes, solid lipid nanoparticles of nanoparticles of porous silicon to provide a slow-release drug delivery system to the radiated areas.

In one embodiment, a formulation of nanoparticles coated with Wnt or Rock inhibitors is used from the group consisting of topical administration at a concentration of about 50 pg/ml to less than 1 .micrograms/ml, subcutaneous or submucosal injection or interstitial tissue at a dose in the range of about 1 picograms/ml to about 200 .mu.g/ml, local injection at a dose in the range of about picograms/0.1 ml to about 4 nanogram/ml to 20 .mu.g/ml, or injection close to major nerve plexus etc. at a dose in the range of about 2 nanograms to 200 nanograms/ml as a slow release medication, or injecting a solution of 0.01-0.5 ml or more in a physiologic PH adjusted to 7-7.5 PH and osmolarity of 280-300 mOsm.

In one embodiment, a formulation of Wnt or Rock inhibitors is used comprising local administering or injecting a solution of 0.01-0.5 ml or more in a physiologic PH adjusted to 7-7.5 PH and osmolarity of 280-300 mOsm to a patient after radiation with plaque therapy. In one embodiment, a formulation of Wnt or Rock inhibitors is used as a composition consisting essentially of Rock inhibitors, such as Botox, in a pharmaceutically acceptable formulation and in an amount effective to enhance post-surgical recovery to treat vascular occlusion in the area in the patient wherein the composition is administered at a concentration up to about 10 micrograms/ml by at least one of slow release polycaprolactone, polylactic or polyglycolic acid, microparticles of porous silicone, etc. at a concentration in the range between about 10 picograms/ml to less than 1 micrograms/ml to the radiated area or neuropathy injecting a solution of 0.01-0.5 ml or more in a physiologic PH adjusted to 7-7.5 PH and osmolarity of 280-300 mOsm.

In one embodiment, the composition is administered by injecting a solution of 0.01-0.5 ml or more in a physiologic PH adjusted to 7-7.5 PH and osmolarity of 280-300 mOsm subcutaneously or close to the major trunk of the irritated nerve or nerve plexus or injected at a dose in the range of about 1 picograms/ml to about 200 nanograms/ml, at a dose in the range of about 1 picograms/0.1 ml to about 20 nanograms/ml, or retrobulbar injection at a dose in the range of about 20 nanograms/ml to about 2 micrograms/ml at the site of radiation or chemotherapy induced neuropathy by injecting in a solution of 0.01-0.5 ml or more in a physiologic PH adjusted to 7-7.5 PH and osmolarity of 280-300 mOsm.

In one embodiment, the methodology involves administering or injecting a solution of 0.01-0.5 ml or more in a physiologic PH adjusted to 7-7.5 PH and osmolarity of 280-300 mOsm to a patient with a non-toxic dose of nanoparticle coated Wnt inhibitor and/or Rho Kinase inhibitor having diabetic neuropathy, induced neuropathy, and pain induced by ischemia and neuropathy of the affected area where the neuropathies occur in patients with long standing diabetes characterized by microvascular abnormalities of the nerve supply, leading to hyper- and hypoaesthesia, burning sensation in the affected area of the long or short nerve distribution, affecting worldwide more than 130 million people where the diagnosis is made by the history of long standing diabetes, poor sugar control, high glycation index, affecting the sensitivity of the skin of the foot, etc. is reduced to vibration and pressure and can lead to pins and needles sensation, or ultimately the vascular occlusion that causes ulceration and amputation of the toes or leg, etc., and when cranial nerves are affected it will lead to paresis or paralysis of the fourth, fifth, sixth, and seven nerves associated with diplopia, and the neuropathy can also affect the optic nerve and the sensation of the cornea, leading to dry eye formation and similarly the autonomous nervous system can be affected causing diarrhea, erectile dysfunction, and urinary incontinent, difficulty with swallowing dizzy and possible fainting.

In one embodiment, in patients with a neuropathy caused by any nerve injury, diabetes, radiation or chemotherapy or surgery or trauma, the standard therapy includes blood sugar control and exercise, and administration of medications, such as an ACE inhibitor to produce vasodilatation, antiepileptic medications, including tricyclic antidepressants or anticonvulsants such as pregabalin, valperoic acid, opioids, topical agents, such as Capsaicin, serotonin-neurepinephrine reuptake inhibitors, therapeutic ultrasound, or heating by laser.

In one embodiment one administers topically, or by local injection, a solution of 0.01-0.5 ml or more in a physiologic PH adjusted to 7-7.5 PH and osmolarity of 280-300 mOsm, or oral administration of Rock or Wnt inhibitors to prevent vascular damage to the nerve cells, prevent endothelial cell loss, provide oxygen to the constricted capillaries, and induce regeneration of the affected nerve axons, prevent secondary inflammatory processes in diabetes produced by diabetic vasculopathy along with glycemic control and exercise in patient with neuropathy caused by any nerve injury, diabetes, radiation or chemotherapy or surgery or trauma.

In one embodiment, in a diabetic patient with diabetic neuropathy, one administers topically as an ointment or other preparation or locally by injection or orally as a preparation of Rock or Wnt inhibitors.

In one embodiment, Wnt inhibitors at a non-toxic dose are used, by injecting a solution of 0.01-0.5 ml or more in a physiologic PH adjusted to 7-7.5 PH and osmolarity of 280-300 mOsm from the compound such as: FH535, IWP-2, PNU-74654, IWR-1endo. IWR-exo, Demethoxy Curcumin, CCT036477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab etc. small molecule Wnt inhibitor PKF118-310, the Wnt/β-catenin pathway inhibitor, and fasudil, a rock inhibitor, Fasudil (HA-1077), a selective RhoA/Rho kinase (ROCK) inhibitor, or Y-27632, small molecule inhibitor of ROCK1 and ROCK2, Fasudil1-(5-Isoquinolinesulfonyl)-2 Methylpiperazine Calcium Channel Blockers. Membrane Transport Modulators etc. Canakinumab ivermectin, or niclosamide, Botulinum toxine or Botax, all having a good penetration into the skin or mucosa or can be delivered as a slow release compound implanted or injected inside the affected tissue with any polymeric compound, such as the polymers previously disclosed (e.g., polycaprolactone, poly (glycolic) acid, poly(lactic) acid, polyanhydride) or lipids that may be formulated as microspheres or dendrimers. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be administered as an oral preparation or topically as an ointment or other preparation or locally by injection as nanoparticles and/or microparticles with (alpha)-cyclodextrin, or (beta)-cyclodextrin, or (gamma)-cyclodextrin, hydroxypropyl-b-cyclodextrin (bHPCD). In a formulation for topical application, the drug is slowly released over time as the liposome capsule degrades due to wear and tear from the surface of the skin or mucosa. In a formulation for intraocular injection, the liposome capsule degrades due to cellular digestion, other slow release polymers, such as PLA, PGA, Polycaprolactone, microsphere, dendrimers) or as nanoparticles and/or microparticles of porous silicon or with (alpha)-cyclodextrin, or (beta)-cyclodextrin, or (gamma)-cyclodextrin, hydroxypropyl-b-cyclodextrin (bHPCD) are also utilized or some such as Fasudil orally at doses of 40-80 mg. This is equal to 1 microgram/ml to 40 micrograms/ml or to 80 micrograms/ml or more for topical application having ranges of 40 nanograms/ml to 4 micrograms/ml, or 0.1 micrograms/ml to 40 micrograms/ml or more for topical applications without having the side effects of steroid preparation, in addition the following compounds are readily available and some have been approved by the FDA: potent ROCK inhibitor; orally bioavailable Fasudil hydrochloride, Inhibitor of cyclic nucleotide dependent- and Rho-kinases GSK 269962, Potent and selective ROCK inhibitor GSK 429286, Selective Rho-kinase (ROCK) inhibitor H1152 dihydrochloride, Selective Rho-kinase (ROCK) inhibitor Glycyl H 1152 dihydrochloride, Selective Rho-kinase (ROCK) inhibitor; more selective analogue of H1152, Cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride, Botox or botulinum toxin as injectable preparation of topical ointment or with slow release polymers described above. Available Wnt inhibitors include small molecule Wnt inhibitor PKF118-310, the Wnt/β-catenin pathway inhibitor, niclosamide, ivermectin, etc.

In one embodiment of a patient suffering from diabetic neuropathy or radiation neuropathy, one administers the Wnt and or Rho inhibitors orally, or injected at a non-toxic dose to the main trunk of the affected nerve to not only release medication locally, but also systemically slowly and be affected for weeks, months or possible years, enhance the circulation to the area, remove the stagnated cytokine released in hypoxic tissue and encourage nerve regeneration of the tissue.

In one embodiment, a patient with rheumatoid arthritis, spondylitis, disease affecting small or large joints such as knee or shoulder, wrist or fingers or toe, neck or spine vertebrae, nerve compressive effect or inflammatory, bursitis, tendinitis, osteoarthritis, etc., the Wnt inhibitors or Rock inhibitors are used by injecting outside or inside the joint a solution of 0.01-0.5 ml or more in a physiologic PH adjusted to 7-7.5 PH and osmolarity of 280-300 mOsm from the compounds such as: FH535, IWP-2, PNU-74654, IWR-1endo. IWR-exo, Demethoxy Curcumin, CCT036477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, etc. small molecule Wnt inhibitor PKF118-310, the Wnt/β-catenin pathway inhibitor and Fasudil, a rock inhibitor Fasudil (HA-1077), a selective RhoA/Rho kinase (ROCK) inhibitor, or Y-27632, small molecule inhibitor of ROCK1 and ROCK2, Fasudil1-(5-Isoquinolinesulfonyl)-2 Methylpiperazine Calcium Channel Blockers. Membrane Transport Modulators etc. Canakinumab ivermectin, or niclosamide, Botulinum toxin or Botox, all having a good penetration into the skin or mucosa or can be delivered as slow release compound implanted or injected inside the affected tissue with any polymeric compound, such as the polymers previously disclosed (e.g., polycaprolactone, poly(glycolic) acid, poly (lactic) acid, polyanhydride) or lipids that may be formulated as microspheres or dendrimers. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be administered as an oral preparation or topically as an ointment or other preparation or locally by injection as nanoparticles and/or microparticles with (alpha)-cyclodextrin, or (beta)-cyclodextrin, or (gamma)-cyclodextrin, hydroxypropyl-b-cyclodextrin (bHPCD). In a formulation for topical application, the drug is slowly released over time as the liposome capsule degrades due to wear and tear from the surface of the skin or mucosa. In a formulation for intraocular injection, the liposome capsule degrades due to cellular digestion, other slow release polymers such as PLA, PGA, Polycaprolactone, microsphere, dendrimers) or as nanoparticles and/or microparticles of porous silicon or with (alpha)-cyclodextrin, or (beta)-cyclodextrin, or (gamma)-cyclodextrin, hydroxypropyl-b-cyclodextrin (bHPCD) are also utilized or some such as Fasudil orally at doses of 40-80 mg. This is equal to 1 microgram/ml to 40 micrograms/ml or to 80 micrograms/ml or more for topical applications having ranges of 40 nanograms/ml to 4 micrograms/ml, or 0.1 micrograms/ml to 40 micrograms/ml or more for topical applications without having the side effects of steroid preparation, in addition the following compounds are readily available and some have been approved by the FDA: potent ROCK inhibitor; orally bioavailable Fasudil hydrochloride, Inhibitor of cyclic nucleotide dependent- and Rho-kinases GSK 269962, Potent and selective ROCK inhibitor GSK 429286, Selective Rho-kinase (ROCK) inhibitor H1152 dihydrochloride, Selective Rho-kinase (ROCK) inhibitor Glycyl H 1152 dihydrochloride, selective Rho-kinase (ROCK) inhibitor; more selective analogue of H1152, Cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride, Botox or botulinum toxin as injectable preparation of topical ointment or with slow release polymers described above. Available Wnt inhibitors include small molecule Wnt inhibitors PKF118-310, the Wnt/β-catenin pathway inhibitor, niclosamide, ivermectin, etc.

In one embodiment, the procedure can be repeated if pain returns.

In one embodiment, the person suffering from fibromyalgia is treated with injection of nanoparticles coated with polymeric slow release and thermosensitive compounds, such as chitosan, liposomes or solid lipid nanoparticles, nanoparticles and/or microparticles of porous silicon to release at a non-toxic dose, NSAIDs, steroid and Rock inhibitors, e.g., Fasudil, exoenzyme, Y27632, Botox, at picogram to nanogram concentrations, etc., Wnt inhibitor Niclosamide, etc. at pictogram concentrations, injected at the site of pain, subcutaneously, intramuscularly, in the neck muscles, back, leg, arm or fore arms' muscles, close to bursae, close to or in the tendon, close to the painful large or small joints, hips, knees, writs, fingers, toes, close to the vertebrae, jaw, elbows, etc. or in the joint, at the site of prior radiation or injury or trauma, while using thermal imaging with thermal energy such as laser, microwave, or preferably with focused ultrasound in a thermal or non-thermal mode at frequencies or 2 kilohertz to 1-3 megahertz, thus increasing the temperature of the functionalized nanoparticles by a thermal delivery source under the control of the photoacoustic/thermoacoustic imaging system connected to a processor. The energy delivery unit increases the temperature of the functionalized nanoparticles from 37° C. to 41° C.-43° C. to melt the temperature-sensitive coating polymers and release the medication combining the thermotherapy with long term release medications that inhibit inflammatory processes for a long time, and the process can be repeated as needed.

In another embodiment, ultrasound or focused ultrasound is applied with or without a thermal mode to convert the sound energy to electricity, from the injected piezoelectric nanoparticles and to generate an internal electrical current inducing internal polarization/depolarization of the cell membranes and induce muscle cell relaxation.

In another embodiment, after exposure to the focused or non-focused ultrasound waves, applied externally, to the injected antibody coated piezoelectric nanoparticles, such as, quartz or graphene, etc. conjugated with drug delivery, inside the tissue where application of focused ultrasound to the nanoparticles produces an electrical pulse that induces polarization and depolarization of the muscle cells, including the nerve cells for a short period of time at frequencies as low as 30 Hz-100 kHz for 5-15 second to relax the muscle cells by creating an internal electrical current from the piezoelectric nanoparticles under ultrasound application.

Any of the features or attributes of the above described embodiments and variations can be used in combination with any of the other features and attributes of the above described embodiments and variations as desired.

The embodiments shown and described in the specification are only specific embodiments of the inventor who is skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A cancer therapeutic method comprising administering to a patient having an early stage tumor a combination of thermotherapy and immunotherapy, where
    thermotherapy comprises locally administering a plurality of tumor-antibody-coated nanoparticles and/or microparticles at a site of a tumor, the thermotherapy further comprises heating the tumor-antibody-coated nanoparticles and/or microparticles using an energy source at the site of the tumor so as to damage one or more tumor cell membranes and release antigenic material in vivo that activates and stimulates an immunogenic response of the patient at the site of the tumor; and
    immunotherapy comprises administering immune stimulators locally together with the plurality of tumor-antibody-coated nanoparticles and/or microparticles at the site of the tumor;
    where the tumor-antibody-coated nanoparticles and/or microparticles are conjugated with (alpha)-cyclodextrin, (beta)-cyclodextrin, (gamma)-cyclodextrin, hydroxypropyl-b-cyclodextrin (bHPCD), and combinations thereof so as to inhibit an excessive innate immune response and to prevent excessive edema at the site of the tumor.

2. The method of claim 1 where locally administering a plurality of tumor-antibody-coated nanoparticles and/or microparticles at a site of a tumor comprises injecting the plurality of tumor-antibody-coated nanoparticles and/or microparticles intra-arterially into an organ containing the tumor so as to avoid the adverse effects of systemic intravenous administration.

3. The method of claim 1 where locally administering a plurality of tumor-antibody-coated nanoparticles and/or microparticles at a site of a tumor comprises delivering the plurality of tumor-antibody-coated nanoparticles and/or microparticles using a flexible tube and fiber optic device, the flexible tube and fiber optic device being inserted through a natural orifice of the body or through an artery or vein feeding the tissue at the site of the tumor; and
    where heating the tumor-antibody-coated nanoparticles and/or microparticles using an energy source comprises heating the tumor-antibody-coated nanoparticles and/or microparticles and the tumor using laser pulses emitted from the fiber optic device so as to damage the one or more tumor cell membranes located proximate to the fiber optic device.

4. The method of claim 1 where heating the tumor-antibody-coated nanoparticles and/or microparticles using an energy source comprises externally heating the tumor-antibody-coated nanoparticles and/or microparticles and the tumor locally using a device located outside of the body, the device emitting electromagnetic radiation, focused ultrasound, microwaves, radio frequency (RF) waves, an alternating magnetic field, or combinations thereof.

5. The method of claim 1 where the immune stimulators administered locally are selected from the group consisting of viral-like particles (VLP), adjuvants, interferon alpha, interleukin-2 (IL-2), interleukin-6 (IL-6), interleukin-17 (IL-17), toll-like receptors (TLR), tumor necrosis factor (TNF) alpha, and combinations thereof.

6. The method of claim 1 where the tumor-antibody-coated nanoparticles and/or microparticles are conjugated with a prothrombotic medication that creates a discrete blood clot or localized thrombus at the site of the heated tumor, thereby obstructing a blood supply to the tumor, and starving the tumor of the blood supply.

7. The method of claim 1 where the tumor-antibody-coated nanoparticles and/or microparticles are conjugated with a slow release polymer, the slow release polymer selected from the group consisting of chitosan, poly(lactic-co-glycolic acid), lactic acid, glycolic acid, and combinations thereof.

8. The method of claim 1 where the tumor-antibody-coated nanoparticles and/or microparticles comprise tumor-antibody-coated nanoparticles selected from the group consisting of porous silicon nanoparticles, solid lipid nanoparticles, liposomes, nanowires, nanotubes, nanoshells, nanocages, periodic mesoporous organosilica nanoparticles, and combinations thereof.

9. The method of claim 1 where the tumor-antibody-coated nanoparticles and/or microparticles are conjugated with sodium bicarbonate to modify the acidic tumor cell environment at the site of the tumor so as to inhibit the growth of the tumor.

10. The method of claim 1 where the tumor-antibody-coated nanoparticles and/or microparticles are conjugated with N-myristoyltransferase (NMT) inhibitors so as to inhibit tumor cellular proliferation at the site of the tumor.

11. The method of claim 1 where the tumor-antibody-coated nanoparticles and/or microparticles administered locally at the site of the tumor are conjugated with Rock inhibitors for treating neuropathy by enhancing neural regeneration and reducing inflammation, the Rock inhibitors being selected from the group consisting of Fasudil, exoenzyme, Y27632, Botox, and combinations thereof; and
    where the neuropathy is being prophylactically treated prior to radiation being applied at the site of the tumor so as to reduce the effects of radiation neuropathy following the application of the radiation, radiation neuropathy resulting from radiation previously applied at the site of the tumor is being treated, and/or neuropathy resulting from diabetes or another cause other than radiation is being treated.

12. The method of claim 1 where the tumor-antibody-coated nanoparticles and/or microparticles are conjugated with checkpoint inhibitors selected from the group consisting of PD-1, PD-L1, CTLA-4, jagged 1 inhibitor 15D11, and combinations thereof, the checkpoint inhibitors blocking checkpoint proteins on the tumor cells of the tumor and/or checkpoint proteins on immune cells.

13. The method of claim 1 where the tumor-antibody-coated nanoparticles are conjugated with Wnt inhibitors so as to inhibit Wnt activation in the tumor cells of the tumor and tumor cellular proliferation, the Wnt inhibitors selected from the group consisting of niclosamide, ivermectin, selamectin, alpha lipoidic acid, and combinations thereof.

14. The method of claim 1 where the tumor-antibody-coated nanoparticles and/or microparticles comprise tumor-antibody-coated nanoparticles in the form of tumor-antibody-coated piezoelectric nanoparticles, and where a focused compressive ultrasonic wave generated by an ultrasound source in a first compressive non-thermal mode is delivered in a pulsed manner so as to generate an electric pulse from the tumor-antibody-coated piezoelectric nanoparticles that depolarizes the one or more tumor cell membranes so as to increase a permeability of the one or more tumor cell membranes and damage the tumor cells of the tumor.

15. The method of claim 14 where at least some of the tumor-antibody-coated nanoparticles and/or microparticles are coated with a thermosensitive polymer that contains an anti-cancer therapeutic agent.

16. The method of claim 15 further comprises the steps of:
heating the tumor-antibody-coated piezoelectric nanoparticles in a second thermal mode using a ultrasound source that raises the temperature of the tumor cell/nanoparticle complex to a temperature of about 41° C. to about 43° C. or more so as to further damage one or more tumor cell membranes at the site of the tumor and melt the thermosensitive polymer coating of the tumor-antibody-coated piezoelectric nanoparticles to release the anti-cancer therapeutic agent so that the anti-cancer therapeutic agent is able to penetrate the one or more damaged tumor cell membranes and kill the tumor cells; and
alternating the heating of the nanoparticles in the second thermal mode with the focused compressive ultrasonic wave in the first compressive non-thermal mode under the control of a processor controlling the thermal energy intensity and duration of the ultrasound source.

17. The method of claim 15 where the thermosensitive polymer coating of the tumor-antibody-coated nanoparticles and/or microparticles further comprises one or more inhibitory genes and a CRISPR/cas9 complex to modify tumor genes at the site of the tumor upon release from the thermosensitive polymer coating of the tumor-antibody-coated nanoparticles and/or microparticles at a temperature of about 41° C. to about 43° C., the genetic modification of the tumor genes preventing the production of checkpoint proteins by the tumor cells of the tumor so that the tumor cells are attacked by the natural immune cells of the patient.

18. The method of claim 17, where gene modification is done using CRISPR/cas9 mediated homology-independent targeted integration (HITI) or homology directed repair (HDR).

19. The method of claim 17, where the tumor-antibody-coated nanoparticles and/or microparticles are conjugated with checkpoint inhibitors selected from the group consisting of PD-1, PD-L1, CTLA-4, jagged 1 inhibitor 15D11, and combinations thereof, the checkpoint inhibitors blocking checkpoint proteins on the tumor cells and/or checkpoint proteins on immune cells; and
where, due to the genetic modification of the tumor genes that prevents the production of checkpoint proteins by the tumor cells, the dosage of the checkpoint inhibitors administered via the tumor-antibody-coated nanoparticles and/or microparticles intra-arterially is substantially lower than a systemic non-toxic dosage of checkpoint inhibitors.

20. The method of claim 1 where the tumor-antibody-coated nanoparticles and/or microparticles are conjugated with an anti-VEGF medication that inhibits a vascular growth of the tumor.

21. A cancer therapeutic method comprising administering to a patient having an early stage tumor a combination of thermotherapy and immunotherapy, where
thermotherapy comprises locally administering a plurality of tumor-antibody-coated nanoparticles and/or microparticles at a site of a tumor, the thermotherapy further comprises heating the tumor-antibody-coated nanoparticles and/or microparticles using an energy source at the site of the tumor so as to damage one or more tumor cell membranes and release antigenic material in vivo that activates and stimulates an immunogenic response of the patient at the site of the tumor; and
immunotherapy comprises administering immune stimulators locally together with the plurality of tumor-antibody-coated nanoparticles and/or microparticles at the site of the tumor;
where locally administering a plurality of tumor-antibody-coated nanoparticles and/or microparticles at the site of the tumor comprises delivering the plurality of tumor-antibody-coated nanoparticles and/or microparticles using a flexible tube and fiber optic device, the flexible tube and fiber optic device being inserted through a natural orifice of the body or through an artery or vein feeding the tissue at the site of the tumor; and
where heating the tumor-antibody-coated nanoparticles and/or microparticles using an energy source comprises heating the tumor-antibody-coated nanoparticles and/or microparticles and the tumor using laser pulses emitted from the fiber optic device so as to damage the one or more tumor cell membranes located proximate to the fiber optic device.

22. A cancer therapeutic method comprising administering to a patient having an early stage tumor a combination of thermotherapy and immunotherapy, where
thermotherapy comprises locally administering a plurality of tumor-antibody-coated nanoparticles and/or microparticles at a site of a tumor, the thermotherapy further comprises heating the tumor-antibody-coated nanoparticles and/or microparticles using an energy source at the site of the tumor so as to damage one or more tumor cell membranes and release antigenic material in vivo that activates and stimulates an immunogenic response of the patient at the site of the tumor; and
immunotherapy comprises administering immune stimulators locally together with the plurality of tumor-antibody-coated nanoparticles and/or microparticles at the site of the tumor;
where the tumor-antibody-coated nanoparticles and/or microparticles are conjugated with at least one of: (i) sodium bicarbonate to modify the acidic tumor cell environment at the site of the tumor so as to inhibit the growth of the tumor, and (ii) N-myristoyltransferase (NMT) inhibitors so as to inhibit tumor cellular proliferation at the site of the tumor.

* * * * *